(12) United States Patent
Ron Edoute et al.

(10) Patent No.: US 10,463,869 B2
(45) Date of Patent: *Nov. 5, 2019

(54) ESTHETIC APPARATUS USEFUL FOR INCREASING SKIN REJUVENATION AND METHODS THEREOF

(71) Applicant: Venus Concept Ltd., Karmiel (IL)

(72) Inventors: Oded Ron Edoute, Tel Aviv (IL); Orit Ron Edoute, Tel Aviv (IL); Itzhak Kremin, Givatayim (IL); Vadim Polyakov, Petach Tikva (IL); Boris Vaynberg, Zichron Yakov (IL)

(73) Assignee: VENUS CONCEPT LTD., Karmiel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/647,211

(22) Filed: Jul. 11, 2017

(65) Prior Publication Data

US 2017/0304642 A1   Oct. 26, 2017

Related U.S. Application Data

(60) Continuation of application No. 15/204,158, filed on Jul. 7, 2016, which is a continuation-in-part of (Continued)

(51) Int. Cl.
*A61N 2/00* (2006.01)
*A61F 7/00* (2006.01)
(Continued)

(52) U.S. Cl.
CPC .............. *A61N 2/002* (2013.01); *A61F 7/00* (2013.01); *A61F 7/007* (2013.01); *A61N 1/328* (2013.01);
(Continued)

(58) Field of Classification Search
CPC ........ A61B 18/203; A61B 2018/00452; A61N 1/328; A61N 1/403; A61N 2/004;
(Continued)

(56) References Cited

U.S. PATENT DOCUMENTS

| 4,140,130 A | * | 2/1979 | Storm, III | .............. | A61N 1/403 |
| | | | | | 219/770 |
| 5,571,154 A | * | 11/1996 | Ren | .......................... | A61N 5/04 |
| | | | | | 219/690 |

(Continued)

*Primary Examiner* — Christine H Matthews
*Assistant Examiner* — Joshua Daryl D Lannu
(74) *Attorney, Agent, or Firm* — The Roy Gross Law Firm, LLC; Roy Gross

(57) ABSTRACT

The present invention provides a device for rejuvenating a region of skin or mucosal tissue, comprising: a pulsed electromagnetic frequency generator; a plurality of electrodes in communication with the pulsed electromagnetic frequency generator and an RF tissue diathermy device. The electrodes apply the pulsed electromagnetic power and the RF tissue diathermy to the tissue, heating it such that one portion of the region of mucosal tissue is maintained at a predetermined temperature range $T_1$ while another portion of the region of mucosal tissue is at least temporarily maintained at predetermined temperature range $T_2$.

20 Claims, 23 Drawing Sheets

Related U.S. Application Data application No. 14/845,315, filed on Sep. 4, 2015, now Pat. No. 9,814,897, which is a continuation of application No. 14/489,572, filed on Sep. 18, 2014, now Pat. No. 9,694,194, which is a division of application No. 13/954,320, filed on Jul. 30, 2013, now Pat. No. 8,979,727, which is a division of application No. 13/001,834, filed as application No. PCT/IL2009/000644 on Jun. 29, 2009, now Pat. No. 8,998,791.

(60) Provisional application No. 61/112,783, filed on Nov. 10, 2008, provisional application No. 61/076,652, filed on Jun. 29, 2008.

(51) Int. Cl.

| | |
|---|---|
| *A61N 1/32* | (2006.01) |
| *A61N 7/02* | (2006.01) |
| *A61N 5/00* | (2006.01) |
| *A61N 2/02* | (2006.01) |
| *A61N 1/40* | (2006.01) |
| *A61N 5/06* | (2006.01) |
| *A61N 7/00* | (2006.01) |
| *A61B 18/20* | (2006.01) |
| *A61B 18/00* | (2006.01) |
| *A61B 18/14* | (2006.01) |

(52) U.S. Cl.
CPC ............. *A61N 1/403* (2013.01); *A61N 2/004* (2013.01); *A61N 2/02* (2013.01); *A61N 5/00* (2013.01); *A61N 5/0625* (2013.01); *A61N 7/02* (2013.01); *A61B 18/14* (2013.01); *A61B 18/203* (2013.01); *A61B 2018/0047* (2013.01); *A61B 2018/00452* (2013.01); *A61B 2018/00559* (2013.01); *A61B 2018/1417* (2013.01); *A61B 2018/1467* (2013.01); *A61F 2007/0052* (2013.01); *A61F 2007/0086* (2013.01); *A61F 2007/0096* (2013.01); *A61N 5/0616* (2013.01); *A61N 2007/0034* (2013.01)

(58) Field of Classification Search
CPC . A61N 2/02; A61N 7/02; A61N 2/002; A61N 5/0625; A61N 2007/0034; A61N 5/00; A61F 7/00; A61F 2007/0052; A61F 7/007
See application file for complete search history.

(56) References Cited

U.S. PATENT DOCUMENTS

| | | | | |
|---|---|---|---|---|
| 2008/0008793 | A1* | 1/2008 | Forsyth | A23B 7/148 426/118 |
| 2008/0249350 | A1* | 10/2008 | Marchitto | A61B 18/14 600/10 |

* cited by examiner

ESTHETIC APPARATUS USEFUL FOR INCREASING SKIN REJUVENATION AND METHODS THEREOF

FIELD OF THE INVENTION

This invention generally relates to an esthetic device used to improve viability of skin or mucosal tissue and rejuvenation of skin or mucosal tissue, and a method of using the device.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

A few main approaches to tightening of the skin are common practice today. The surgical approach carries disadvantages related to the anesthesia, the surgical complications, and the healing process, which may cause scars. The chemical peel approach usually involves injury to the outermost layer of the skin—the epidermis—which may cause discoloration. Since collagen fibers are found in the dermis—the subcutaneous layer of the skin, and since heat was shown to contract these fibers and generate their production [Zelickson B D, Kist D, Bernstein E, Brown D B, Ksenzenko S, Burns J, Kilmer S, Mehregan D, Pope K. Histological and ultrastructural evaluation of the effects of a radiofrequency-based nonablative dermal remodeling device: a pilot study. Arch Dermatol. 2004 February; 140 (2):204-9], methods of differentially heating the dermis (deep tissue diathermy) have recently arisen.

A unique method of treating the dermis is called Pulsed Electromagnetic Fields (PEMF) therapy. This method usually employs electromagnetic radiation of different frequencies—ranging from static magnetic fields, through extremely low frequencies (ELF) to higher radiofrequencies (RF)—administered in pulses.

PEMF works in more than one way. The radiation absorbed by the tissue can heat the tissue to a desired temperature, depending on the power applied, the frequency transmitted, and, more importantly, the tissue characteristics. For example, the tissue can be heated to denaturation temperatures, which cause tissue damage and coagulation necrosis. Tissue can also be heated to lower temperatures, which can cause the afore-mentioned contraction of collagen fibers.

Another modus operandi involves non-thermal effects, which rely on the reaction of specific tissue components to characteristics of the applied radiation. These effects can be due to large charged molecules and their reaction to various frequencies and their harmonics, charged small ions in the cell membranes affecting cell function and reactions to hormones and chemical signals, charged small ions in the extracellular space and other poorly understood mechanisms.

Furthermore, applying the radiation in pulses was also found to have non-thermal effects. Yet more, specific combinations of frequency, duty cycle and transmitted power can cause specific tissue responses. Recent scientific research has determined PEMF characteristics which can cause desired biophysical responses.

It is now commonly accepted that weak electromagnetic fields (EMF) administered in pulses are capable of initiating various healing processes in fractures, multiple sclerosis and Parkinson's disease, and even delivering pain relief; however it seems that most of the conditions that seem most likely to respond to PEMF are musculoskeletal. Two decades ago, the FDA allowed the use of pulsed radiofrequency electromagnetic fields for treatment of pain and edema in superficial soft tissues. [Rosch, P. J., Markov, M. S., eds. Bioelectromagnetic Medicine, 2004; Marcel Dekker, NY, 251-264].

PEMF can also be used for cosmetic purposes as described above. Several studies have addressed the effect of PEMF on dermal components. For example, in vivo trials showed that pulsed electromagnetic fields of certain field intensities and frequencies increased epidermal collagen synthesis [Ahmadian S, Zarchi S R, Bolouri B. *Effects of extremely-low-frequency pulsed electromagnetic fields on collagen synthesis in rat skin*. Biotechnol Appl Biochem. 2006 February; 43(Pt 2):71-75]. This newly-formed collagen increases skin elasticity and rejuvenates the appearance of the skin.

In vitro trials showed that PEMF increased the degree of endothelial cell tubulization and proliferation, and augmented angiogenesis primarily by stimulating endothelial release of FGF-2, inducing paracrine and autocrine changes in the surrounding tissue [Tepper, O M et al. *Electromagnetic fields increase in vitro and in vivo angiogenesis through endothelial release of FGF-2*. FASEB J. 2004 August; 18(11):1231-3. Epub 2004 Jun. 18]. Angiogenesis, the generation of new blood vessels, increases blood flow to the tissue, which in turn increases delivery of oxygen and nutritional substances to the tissue. This effect is most beneficial for injured tissue, promoting rapid and improved healing. The growth factor which is released further enhances the healing process, both in quality and speed of improvement.

The scientific evidence of the effect of PEMF on tissues was utilized in various applications. For example, US20050182462A1 discloses healthy deep tissue heating using PEMF for the purpose of causing contraction and tightening of the skin.

PEMF has also been used to improve skin wound healing. For example, WO08064272 discloses a method of treating a severe diabetic ulcer using PEMF. The patent also discloses the addition of intermittent compression therapy (ICT) and the use of low intensity ultrasound (up to 50 $W/cm^2$), the latter aimed at inhibiting microbial growth.

Other methods of heating the dermis used non pulsating RF radiation, applied by antenna or electrodes. For example, WO98005380 discloses a method of tightening skin using an RF electromagnetic power delivery device.

Improving the results of skin tightening based on dermis diathermy is still a long felt need, both for esthetic and therapeutic purposes.

SUMMARY OF THE INVENTION

It is one object of the present invention to provide a device for rejuvenating at least one region of mucosal tissue, comprising:
 a pulsed electromagnetic frequency generator to apply pulsed electromagnetic field therapy to said region of mucosal tissue; and a plurality of electrodes in communication with an RF tissue diathermy device wherein said RF tissue diathermy device, via said electrodes, heats said at least one region of mucosal tissue.

It is another object of the present invention to provide the device as disclosed above, wherein at least a portion of said at least one region of mucosal tissue is at least temporarily maintainable at a predetermined temperature range $T_1$ while another at least a portion of said at least one region of said mucosal tissue is at least temporarily maintainable at predetermined temperature range $T_2$, where $T_1$ is equal to or different from $T_2$ It is another object of the present invention to provide the device as defined above, wherein at least one temperature sensor is adjacent to at least one of said plurality of electrodes.

It is another object of the present invention to provide the device as defined above, wherein said region of mucosal tissue is within a vagina.

It is another object of the present invention to provide the device as defined above, additionally comprising a database configured to store at least one temperature profile, said temperature profile comprising at least one temperature T and at least one portion of said region of mucosal tissue.

It is another object of the present invention to provide the device as defined above, additionally comprising a processor in communication with said at least one temperature sensor and with said database.

It is another object of the present invention to provide the device as defined above, wherein the at least one temperature sensor is selected from a group consisting of: a thermistor, a thermocouple and any combination thereof.

It is another object of the present invention to provide the device as defined above, wherein each said at least one temperature is measurable in said at least one portion of said region of mucosal tissue.

It is another object of the present invention to provide the device as defined above, wherein said electromagnetic pulse has a frequency between about 10 Hz and about 25 Hz and intensity of about 20 gauss.

It is another object of the present invention to provide the device as defined above, wherein said electromagnetic pulse is at a frequency of about 15 Hz, duration of about 5 ms and intensity of about 12 gauss.

It is another object of the present invention to provide the device as defined above, wherein said processor is configured to feedback control RF output to said pulsed electromagnetic frequency generator and said RF tissue diathermy device such that said temperature profile is maintainable in at least one predetermined region outside said device.

It is another object of the present invention to provide the device as defined above, wherein said RF tissue diathermy device (4) additionally comprises:
a. at least one electrical output device configured to generate RF power;
b. at least two electrodes electrically coupled to said electrical output device and placed on said region of mucosal tissue, wherein said electrodes are configured to apply said RF power to said region of mucosal tissue in a manner selected from a group consisting of: simultaneously, sequentially and any combination thereof.

It is another object of the present invention to provide the device as defined above, wherein said system reduces side effects and/or harmful effects of said electromagnetic pulses and/or said RF tissue diathermy such that said reduction of said side effects and/or said harmful effects is greater than the sum of said reduction of said electromagnetic pulses and/or said reduction of said RF tissue diathermy.

It is another object of the present invention to provide the device as defined above, wherein said system additionally comprising a control system (6) configured to regulate said electromagnetic pulses and/or said electromagnetic pulses.

It is another object of the present invention to provide the device as defined above, wherein said pulsed electromagnetic frequency generator is configured to provide a dynamic magnetic field such that said electromagnetic pulses vary with time.

It is another object of the present invention to provide the device as defined above, wherein the shape of said electromagnetic pulse is selected in a non-limiting manner from a group consisting of square wave, a sine wave, a triangular wave, sawtooth wave, ramp waves, spiked wave and any combination thereof.

It is another object of the present invention to provide the device as defined above, wherein the duration of each pulse applied by said pulsed electromagnetic frequency generator is in a range between about 3 ms and about 1000 ms.

It is another object of the present invention to provide the device as defined above, wherein the frequency F applied by the pulses of said pulsed electromagnetic frequency generator is in a range between about 1 Hz and about 1 MHz.

It is another object of the present invention to provide the device as defined above, wherein the power P applied by the pulses of said pulsed electromagnetic frequency generator is in a range between about 1 W and about 150 W of RMS average power.

It is another object of the present invention to provide the device as defined above, wherein said RF tissue diathermy device (4) is selected in a non-limiting manner from a group consisting of RF tissue diathermy, ultrasonic diathermy, an optical device, electromagnetic induction, sound wave emitting instrument, direct heat applying instrument, or from any other means of heating tissue to temperature T.

It is another object of the present invention to provide the device as defined above, wherein said optical device is configured to emit light in wavelengths absorbed by tissue such that said tissue is heated.

It is another object of the present invention to provide the device as defined above, wherein said sound wave emitting instrument is configured to emit sound waves absorbed by the tissue such that said tissue is heated.

It is another object of the present invention to provide the device as defined above, wherein a member of a group selected from: said temperature $T_1$, said temperature $T_2$ and any combination thereof is higher than about 30 degrees C. and lower than about 80 degrees C.

It is another object of the present invention to provide the device as defined above, wherein said temperature T is higher than about 30 degrees C. and lower than about 80 degrees C.

It is another object of the present invention to provide the device as defined above, wherein said power supply and control system (6) monitors physical tissue parameters and changes applied heat and electromagnetic pulses accordingly.

It is another object of the present invention to provide the device as defined above, wherein said power supply and control system (6) additionally comprise:
a. a processor configured to store in a communicable database predetermined parameters defining (i) safe treatment parameters and (ii) unsafe treatment parameters; said parameters are selected from a group consisting of time t of said treatment, temperature T of said tissue, duty cycle $t_p/t_r$, frequency F, power P applied by the pulses of said pulsed electromagnetic frequency generator, depth D of said treated tissue, magnetic field intensity B, tissue impedance, specific absorption rate (SAR), treatment depth, superficial muscle contractions and any combination thereof;
b. at least one sensor configured to sense electromagnetic radiation and heat radiation parameters selected from a group consisting of time t of time t of said treatment, temperature T of said tissue, duty cycle $t_p/t_r$, frequency F, power P applied by the pulses of said pulsed electromagnetic frequency generator, intensity I of said ultrasound irradiation, depth D of said treated tissue, magnetic field intensity B, tissue impedance, specific absorption rate (SAR), treatment depth, superficial muscle contractions and any combination thereof;
c. at least one regulating mechanism configured to allow said electromagnetic radiation and said heat radiation if said parameters are within said safe treatment parameters and to stop the electromagnetic radiation if the radiation parameters are in said unsafe treatment parameters.

It is another object of the present invention to provide the device as defined above, wherein said power supply and control system includes a mechanism for cooling the skin or mucosal tissue.

It is another object of the present invention to provide the device as defined above, wherein said system is encased in at least one platform.

It is another object of the present invention to provide the device as defined above, wherein said pulsed electromagnetic frequency generator and said RF tissue diathermy device have more than one applicator to treat more than one body part simultaneously.

It is another object of the present invention to provide the device as defined above, wherein said pulsed electromagnetic frequency generator has electrostatic shielding.

It is another object of the present invention to provide the device as defined above, especially configured to increase rejuvenation of the skin or mucosal tissue in a term less than about a week.

It is another object of the present invention to provide the device as defined above, especially configured to increase rejuvenation of the skin or mucosal tissue in a term between about two weeks and about three weeks.

It is another object of the present invention to provide the device as defined above, especially configured to increase rejuvenation of the skin or mucosal tissue in a term greater than about a month.

It is another object of the present invention to provide the device as defined above, wherein said system is especially configured to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 and any combination thereof.

It is another object of the present invention to provide a method (400) of increasing rejuvenation of a region of a patient's mucosa. The method comprises steps selected inter alia from:
 a. obtaining (i) pulsed electromagnetic frequency generator; and, (ii) an RF tissue diathermy device; and,
 b. applying either simultaneously or in batch like manner (a) heat to tissue within said region up to temperature T, (b) pulses of electromagnetic field to said region; and any combination thereof wherein said increase in said rejuvenation of said mucosal tissue is greater than the sum of increase in rejuvenation due to said applying heat to a tissue within said region of mucosal tissue and increase due to said applying pulses electromagnetic therapy to said region of mucosal tissue.

It is another object of the present invention to provide the method as defined above, additionally comprising step of at least temporarily maintaining at least one said region of mucosal tissue at a predetermined temperature range $T_1$ while at least one second mucosal tissue region is at least temporarily maintained at predetermined temperature range $T_2$, where $T_1$ is the same as or different from $T_2$.

It is another object of the present invention to provide the method as defined above, additionally comprising step of selecting said region of mucosal tissue to be within a vagina.

It is another object of the present invention to provide the method as defined above, additionally comprising steps of: (a) providing a database comprising a temperature profile, said temperature profile containing at least one temperature and at least one predetermined region; (b) measuring said at least one temperature at said at least one predetermined region; and (c) feedback controlling output to said pulsed electromagnetic frequency generator and said RF tissue diathermy device, thereby maintaining said temperature profile in said at least one predetermined region.

It is another object of the present invention to provide the method as defined above, additionally comprising steps of (a) providing a vaginal treatment device comprising a distal portion and a proximal portion, said distal portion and said proximal portion reversibly connectible; said proximal portion in communication with a member of a group consisting of said pulsed electromagnetic frequency generator, said RF tissue diathermy device and any combination thereof; said distal portion comprising at least two electrodes; (b) placing said distal portion at least partially within said vagina; (c) keeping at least a part of said distal portion substantially stationary within said vagina for a time period in a range between about 1 minute and about 20 minutes; (d) for at least a portion of said time period, activating a member of a group consisting of said pulsed electromagnetic frequency generator, said RF tissue diathermy device and any combination thereof, said activation applying a member of a group consisting of pulsed electromagnetic field, heat and any combination thereof to tissue in said vagina; and (e) for at least a portion of said time period, measuring temperature of said tissue in said vagina.

It is another object of the present invention to provide the method as defined above, additionally comprising steps of (a) providing said distal portion with at least two pairs of electrodes; and (b) controlling each pair separately, thereby maintaining said temperature profile within at least a portion of said vagina.

It is another object of the present invention to provide the method as defined above, additionally comprising step selected from a group consisting of: simultaneously applying said pulsed electromagnetic field and said heat, sequentially applying said pulsed electromagnetic field and said heat and any combination thereof.

It is another object of the present invention to provide the method as defined above, wherein said step of applying heat to a tissue additionally comprises steps of:
 a. obtaining at least one electrical output device configured to generate either RF electromagnetic power or electrical current;
 b. electrically coupling at least two electrodes to said electrical output device;

c. placing said at least two electrodes on said skin or mucosal tissue region; and, d. applying via at least one said electrodes a member of a group consisting of: said RF power, said electrical current and any combination thereof to said skin or mucosal tissue region.

It is another object of the present invention to provide the method as defined above, additionally comprising a step of selecting at least one parameter from a group consisting of (a) the duration of each pulse applied by said pulsed electromagnetic frequency generator (2) to be greater than about 3 ms and lower than about 1000 ms; (b) the magnetic field intensity B of each pulse applied by said step of applying pulsed electromagnetic therapy to said region (c) the frequency F applied by the pulses applied by said step of applying pulsed electromagnetic therapy to said region to be higher than about 1 Hz and lower than about 1 MHz; (d) the power P applied by said step of applying pulsed electromagnetic therapy to said region to be greater than about 1 W and lower than about 150 W of RMS average power.

It is another object of the present invention to provide the method as defined above, wherein step of applying heat is applied for about 0.01 minutes to about 60 minutes.

It is another object of the present invention to provide the method as defined above, wherein the heat and the pulsed electromagnetic therapy are applied simultaneously, sequentially or separately.

It is another object of the present invention to provide a method (410) of increasing rejuvenation of a region of a patient's skin or mucosal tissue. The method comprises steps selected inter alia from:
a. obtaining (i) pulsed electromagnetic frequency generator; and, (ii) an RF tissue diathermy device;
b. applying pulses of electromagnetic field to said region; and,
c. applying heat to a tissue within said region up to temperature T;
wherein said skin rejuvenation increase is greater than the sum of the rejuvenation due to said applying heat to a tissue within said region and the rejuvenation due to said applying pulsed electromagnetic therapy to said region.

It is another object of the present invention to provide a method (420) of increasing rejuvenation of a region of a patient's skin or mucosal tissue. The method comprises steps selected inter alia from:
a. obtaining (i) pulsed electromagnetic frequency generator; and, (ii) an RF tissue diathermy device;
b. applying heat to a tissue within said region up to temperature T; whilst simultaneously applying pulses of electromagnetic field to said region;
wherein said skin rejuvenation increase is greater than the sum of the increase due to said applying heat to a tissue within said region and the increase due to said applying pulsed electromagnetic therapy to said region.

It is another object of the present invention to provide the method as defined above, additionally comprising a step of selecting said region of mucosal tissue to be within a vagina.

It is another object of the present invention to provide the methods as defined above, wherein said system reduces side effects and/or harmful effects of said electromagnetic pulses and/or said tissue diathermy such that said reduction of said side effects and/or said harmful effects is greater than the sum of said reduction due to said electromagnetic pulses and said reduction due to said tissue diathermy.

It is another object of the present invention to provide the methods as defined above, additionally comprising step of monitoring and/or controlling said steps of applying heat to a tissue within said region and/or said step of applying pulsed electromagnetic therapy to said region.

It is another object of the present invention to provide the methods as defined above, additionally comprising step of applying a dynamic magnetic field onto said region.

It is another object of the present invention to provide the methods as defined above, additionally comprising steps of
a. storing in a communicable database predetermined parameters defining (i) safe treatment parameters and (ii) unsafe treatment parameters; said parameters are selected from a group consisting of time t of said treatment, temperature T of said tissue, duty cycle $t_p/t_r$, frequency F, power P applied by the pulses of said pulsed electromagnetic frequency generator, depth D of said treated tissue, magnetic field intensity B, tissue impedance, specific absorption rate (SAR), treatment depth, superficial muscle contractions and any combination thereof;
b. sensing electromagnetic radiation and heat radiation parameters selected from a group consisting of time t of said treatment, temperature T of said tissue, duty cycle $t_p/t_r$, frequency F, power P applied by the pulses of said pulsed electromagnetic frequency generator, intensity I of said ultrasound irradiation, depth D of said treated tissue, magnetic field intensity B, tissue impedance, specific absorption rate (SAR), treatment depth, superficial muscle contractions and any combination thereof;
c. allowing said electromagnetic radiation and said heat radiation if parameters are within said safe treatment parameters and stopping the electromagnetic radiation if the radiation parameters are in said unsafe treatment parameters.

It is another object of the present invention to provide the methods as defined above, additionally comprising step of selecting the shape of said electromagnetic pulse is selected in a non-limiting manner from a group consisting of square wave, a sine wave, a triangular wave, sawtooth wave, ramp waves, spiked wave and any combination thereof.

It is another object of the present invention to provide the methods as defined above, additionally comprising step of applying an electromagnetic pulse at a frequency between about 10 Hz and about 25 Hz and intensity of about 20 gauss.

It is another object of the present invention to provide the methods as defined above, additionally comprising step of applying an electromagnetic pulse at a frequency of about 15 Hz, duration of about 5 ms and intensity of about 12 gauss.

It is another object of the present invention to provide the methods as defined above, additionally comprising step of selecting said RF tissue diathermy device (4) from any device emitting RF radiation or any means configured for producing electrical current absorbed by tissue.

It is another object of the present invention to provide the methods as defined above, wherein said step of applying heat to a tissue additionally comprises steps of
a. obtaining at least one electrical output device configured to generate RF electromagnetic power;
b. electrically coupling at least two electrodes to said electrical output device;
c. placing said at least two electrodes on a surface of said tissue; and,
d. applying said pulses from said pulsed electromagnetic frequency generator and said RF power to said tissue in a manner selected from a group consisting of: simultaneously, sequentially, separately and any combination thereof.

It is another object of the present invention to provide the methods as defined above, wherein said step of applying heat to a tissue additionally comprises steps of
  a. obtaining at least one at least one electrical output device configured to generate electrical current;
  a. electrically coupling at least two electrodes to said electrical output device;
  b. placing said at least two electrodes on said skin or mucosal tissue region; and,
  c. applying said electrical current to said tissue in a manner selected from a group consisting of: simultaneously, sequentially, separately and any combination thereof.

It is another object of the present invention to provide the methods as defined above, additionally comprising step of selecting said temperature T from a region of about 30 degrees C. to about 80 degrees C.

It is another object of the present invention to provide the methods as defined above, additionally comprising step of selecting the duration of each pulse applied by said pulsed electromagnetic frequency generator (2) to be higher than about 3 ms and lower than about 1000 ms.

It is another object of the present invention to provide the methods as defined above, additionally comprising step of selecting the frequency F applied by the pulses applied by said step of applying pulsed electromagnetic therapy to be in a range between about 1 Hz and about 1 MHz.

It is another object of the present invention to provide the methods as defined above, additionally comprising step of selecting the power P applied by said step of applying pulsed electromagnetic therapy to said region to be in a range between about 1 W and about 150 W of RMS average power.

It is another object of the present invention to provide the methods as defined above, additionally comprising step of applying said heat for a time in a range between about 0.01 minutes and about 60 minutes.

It is another object of the present invention to provide the methods as defined above, wherein the heat and the pulsed electromagnetic therapy are applied simultaneously, sequentially or separately.

It is another object of the present invention to provide the methods as defined above, wherein said method is repeated 1 to about 100 times in each treatment.

It is another object of the present invention to provide the methods as defined above, wherein said treatment is repeated more than once.

It is another object of the present invention to provide the methods as defined above, wherein said step of applying heat is performed by devices selected from a group consisting of: RF tissue diathermy, electromagnetic induction, and any other means of heating tissue to temperature T.

It is another object of the present invention to provide the methods as defined above, especially configured to increase skin or mucosal tissue rejuvenation in a term less than about a week.

It is another object of the present invention to provide the methods as defined above, especially configured to increase skin or mucosal tissue rejuvenation in a term between about two weeks and about three weeks.

It is another object of the present invention to provide the methods as defined above, especially configured to increase skin or mucosal tissue rejuvenation in a term greater than about a month.

It is another object of the present invention to provide the methods as defined above, wherein said method is especially configured to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 and any combination thereof.

It is another object of the present invention to provide an integrated system (20) configured to increase rejuvenation of a region of a patient's skin or mucosal tissue, said system comprising at least two electrodes (41) configured to be placed on said region of a patient's mucosal tissue; an electromagnetic field generator configured to generate electromagnetic field pulses; and a control system; none of said electrodes is configured to penetrate said skin or mucosal tissue; each of said electrodes is configured to conduct RF and thereby to provide RF pulses to said region of said patient's mucosal tissue, each of said electrodes is configured to apply heat up to a temperature T in a range of 30 degrees Celsius to 80 degrees Celsius; said control system is configured to control said electromagnetic field generator and application of said heat by said electrodes; and, each said electrode is configured to provide said RF pulses to said region of a patient's mucosal tissue thereby applying said heat to said region of a patient's mucosal tissue, said providing of said electromagnetic pulses and said application of heat occurring in a manner selected from a group consisting of simultaneously, sequentially and any combination thereof.

It is another object of the present invention to provide the integrated system as defined above, wherein at least one region of said mucosal tissue is at least temporarily maintained at a predetermined temperature range $T_1$ while at least one second region of said mucosal tissue is at least temporarily maintained at predetermined temperature range $T_2$, where $T_1$ is different from or the same as $T_2$.

It is another object of the present invention to provide the integrated system as defined above, wherein said mucosal tissue region is within a vagina.

It is another object of the present invention to provide the integrated system as defined above, additionally comprising a database configured to store at least one temperature profile, said temperature profile comprising at least one temperature and at least one portion of said mucosal tissue region.

It is another object of the present invention to provide the integrated system as defined above, additionally comprising a processor in communication with said database and with at least one temperature sensor.

It is another object of the present invention to provide the integrated system as defined above, wherein each said at least one temperature sensor is adjacent to at least one said electrode, said at least one temperature sensor configured to measure at least one temperature in said at least one region of said patient.

It is another object of the present invention to provide the integrated system as defined above, wherein the at least one temperature sensor is selected from a group consisting of: a thermistor, a thermocouple and any combination thereof. It is another object of the present invention to provide the integrated system as defined above, wherein said heat applied to said region of a patient's skin or mucosal tissue is obtained by emitting RF radiation or via producing electrical current absorbed by tissue.

It is another object of the present invention to provide the integrated system as defined above, wherein application of said system increases said rejuvenation of said skin or mucosal tissue such that said skin or mucosal tissue rejuvenation increase (MRI) is greater than the sum of said MRI due to increase in electromagnetic pulses and said MM due to increase in said tissue diathermy.

It is another object of the present invention to provide the integrated system as defined above, wherein said electromagnetic pulse has a frequency between about 10 Hz and about 25 Hz and intensity of about 20 gauss.

It is another object of the present invention to provide the integrated system as defined above, wherein said electromagnetic pulse is at a frequency of about 15 Hz, duration of about 5 ms and intensity of about 12 gauss.

It is another object of the present invention to provide the integrated system as defined above, wherein said system reduces side effects and/or harmful effects of said electromagnetic pulses and/or said tissue diathermy such that said reduction of said side effects and/or said harmful effects is greater than the sum of said reduction of said electromagnetic pulses and/or said reduction of said tissue diathermy.

It is another object of the present invention to provide the integrated system as defined above, wherein said system additionally comprises a control system (6) configured to regulate a member of a group consisting of said electromagnetic pulses, said tissue diathermy and any combination thereof.

It is another object of the present invention to provide the integrated system as defined above, wherein said system is configured to provide a dynamic magnetic field such that an RMS average magnitude of said electromagnetic pulses varies with time.

It is another object of the present invention to provide the integrated system as defined above, wherein a shape of said electromagnetic pulse is selected in a non-limiting manner from a group consisting of square wave, sine wave, triangular wave, sawtooth wave, ramp wave, spiked wave and any combination thereof.

It is another object of the present invention to provide the integrated system as defined above, wherein a duration of each pulse applied by said system is in a range between about 3 ms and about 1000 ms.

It is another object of the present invention to provide the integrated system as defined above, wherein a frequency F of said pulses of said system is in a range between about 1 Hz and about 1 MHz.

It is another object of the present invention to provide the integrated system as defined above, wherein the power P applied by the pulses of said system is in a range between about 1 W and about 150 W of RMS average power.

It is another object of the present invention to provide the integrated system as defined above, wherein said temperature T is in a range between about 30 degrees C. and about 80 degrees C.

It is another object of the present invention to provide the integrated system as defined above, wherein said control system (6) monitors physical tissue parameters and changes applied heat and electromagnetic pulses accordingly.

It is another object of the present invention to provide the integrated system as defined above, wherein said power supply and control system (6) additionally comprises:

a processor, configured to store in a communicable database predetermined parameters defining (i) safe treatment parameters and (ii) unsafe treatment parameters; said parameters are selected from a group consisting of: total duration of a treatment $t_t$, time $t_p$ during which PEW is applied, temperature T of the treated tissue, duty cycle $t_p/t_t$, frequency F, power P applied by the pulses of said pulsed electromagnetic frequency generator, intensity I of said ultrasound irradiation, depth D of said treated tissue, magnetic field intensity B, tissue impedance, specific absorption rate (SAR), superficial muscle contractions and any combination thereof;

at least one sensor configured to sense electromagnetic radiation and heat radiation parameters selected from a group consisting of: total duration of a treatment $t_t$, time $t_p$ during which PEW is applied, temperature T of the treated tissue, duty cycle $t_p/t_t$, frequency F, power P applied by the pulses of said pulsed electromagnetic frequency generator, intensity I of said RF tissue diathermy, depth D of said treated tissue, magnetic field intensity B, tissue impedance, specific absorption rate (SAR), superficial muscle contractions and any combination thereof;

at least one regulating mechanism, configured to allow said electromagnetic radiation and said heat radiation if said parameters are within said safe treatment parameters and to stop the electromagnetic radiation if the radiation parameters are in said unsafe treatment parameters.

It is another object of the present invention to provide the integrated system as defined above, wherein said control system (6) includes a mechanism for cooling the skin or mucosal tissue.

It is another object of the present invention to provide the integrated system as defined above, configured to increase rejuvenation of the skin or mucosal tissue in a term of less than about a week.

It is another object of the present invention to provide the integrated system as defined above, configured to increase rejuvenation of the skin or mucosal tissue in a term of about two weeks to about three weeks.

It is another object of the present invention to provide the integrated system as defined above, especially configured to increase rejuvenation of the skin or mucosal tissue in a term greater than about a month.

It is another object of the present invention to provide the integrated system as defined above, wherein said system is especially configured to operate according to IEC selected from a group consisting of IEC 60601-2-35, IEC 60601-2-33, IEC 60601-2-29, IEC 60601-2-9, IEC 60601-2-5, IEC 60601-2-3, IEC60601-1-8, IEC 60601-1-6, IEC 60601-1-4, IEC 60601-1-3, IEC 60601-1-2, IEC 60601-1-1 and any combination thereof.

It is another object of the present invention to provide a method of increasing rejuvenation of a region of a patient's skin or mucosal tissue. The method comprises steps selected inter alia from:

a. obtaining an integrated system (20) configured to increase rejuvenation of a patient's skin or mucosal tissue; said integrated system (20) comprises: at least two electrodes (41) configured to be placed on said region of a patient's skin or mucosal tissue;
  b. applying heat to a tissue within said region up to temperature T whilst simultaneously applying pulses of electromagnetic field to said region;

wherein said increase in said rejuvenation of said skin or mucosal tissue is greater than the sum of the increase due to said applying heat to a tissue within said region and the increase due to said applying pulsed electromagnetic therapy to said region.

It is another object of the present invention to provide the method as defined above, wherein said step of applying heat to a tissue within said region up to temperature T additionally comprising step of applying electrical current absorbed by tissue.

It is another object of the present invention to provide the method as defined above, wherein said system reduces side effects and/or harmful effects of said electromagnetic pulses and/or said tissue diathermy such that said reduction of said side effects and/or said harmful effects is greater than the sum of said reduction due to said electromagnetic pulses and said reduction due to said tissue diathermy.

It is another object of the present invention to provide the method as defined above, additionally comprising step of monitoring and/or controlling said steps of applying heat to a tissue within said region and/or said step of applying pulsed electromagnetic therapy to said region.

It is another object of the present invention to provide the method as defined above, additionally comprising step of applying a dynamic magnetic field onto said region.

It is another object of the present invention to provide the method as defined above, additionally comprising step of applying electromagnetic pulses at a frequency between about 10 Hz and about 25 Hz and intensity of about 20 gauss.

It is another object of the present invention to provide the method as defined above, additionally comprising step of applying an electromagnetic pulse at a frequency of about 15 Hz, duration of about 5 ms and intensity of about 12 gauss.

It is another object of the present invention to provide the method as defined above, additionally comprising steps of
a storing in a communicable database predetermined parameters defining (i) safe treatment parameters and (ii) unsafe treatment parameters; said parameters are selected from a group consisting of: total duration of a treatment $t_t$, time $t_p$ during which PEMF is applied, temperature T of the treated tissue, duty cycle $t_p/t_t$, frequency F, power P applied by the pulses of said pulsed electromagnetic frequency generator, depth D of said treated tissue, magnetic field intensity B, tissue impedance, specific absorption rate (SAR), treatment depth, superficial muscle contractions and any combination thereof;
b. sensing electromagnetic radiation and heat radiation parameters selected from a group consisting of: total duration of a treatment $t_t$, time $t_p$ during which PEMF is applied, temperature T of the treated tissue, duty cycle $t_p/t_t$, frequency F, power P applied by the pulses of said pulsed electromagnetic frequency generator, intensity I of said ultrasound irradiation, depth D of said treated tissue, magnetic field intensity B, tissue impedance, specific absorption rate (SAR), treatment depth, superficial muscle contractions and any combination thereof;
c. allowing said electromagnetic radiation and said heat radiation if said parameters are within said safe treatment parameters and stopping the electromagnetic radiation if the radiation parameters are in said unsafe treatment parameters.

It is another object of the present invention to provide the method as defined above, additionally comprising step of selecting the shape of said electromagnetic pulse is selected in a non-limiting manner from a group consisting of a square wave, a sine wave, a triangular wave, a sawtooth wave, a ramp wave, a spiked wave and any combination thereof.

It is another object of the present invention to provide the method as defined above, additionally comprising step of selecting said temperature T to be in a range from about 30 degrees C. to about 80 degrees C.

It is another object of the present invention to provide the method as defined above, additionally comprising step of selecting the duration of each pulse applied by said pulsed electromagnetic frequency generator (2) to be higher than about 3 ms and lower than about 1000 ms.

It is another object of the present invention to provide the method as defined above, additionally comprising step of selecting the frequency F applied by the pulses applied by said step of applying pulsed electromagnetic therapy to said region to be higher than about 1 Hz and lower than about 1 MHz.

It is another object of the present invention to provide the method as defined above, additionally comprising step of selecting the power P applied by said step of applying pulsed electromagnetic therapy to said region to be in a range between about 1 W and about 150 W of RMS average power.

It is another object of the present invention to provide the method as defined above, wherein step of applying heat is applied for about 0.01 minutes to about 60 minutes.

It is another object of the present invention to provide the method as defined above, wherein the heat and the pulsed electromagnetic therapy are applied simultaneously, sequentially or separately.

It is another object of the present invention to provide the method as defined above, wherein said method is repeated about 1 to about 100 times in each treatment.

It is another object of the present invention to provide the method as defined above, wherein said treatment is repeated more than once.

It is another object of the present invention to provide the method as defined above, wherein said step of applying heat is performed by devices selected from a group consisting of: RF tissue diathermy, electromagnetic induction, direct heat applying instrument, and any other means of heating tissue to temperature T.

It is another object of the present invention to provide the method as defined above, especially configured to increase skin or mucosal tissue rejuvenation in a term less than about a week.

It is another object of the present invention to provide the method as defined above, especially configured to increase skin or mucosal tissue rejuvenation in a term from about two weeks to about three weeks.

It is still an object of the present invention to provide the method as defined above, especially configured to increase skin or mucosal tissue rejuvenation in a term greater than about a month.

It is lastly an object of the present invention to provide the method as defined above, wherein said method is especially configured to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 and any combination thereof.

It is another object of the present invention to provide a device for rejuvenating a mucosal region, comprising:
a pulsed electromagnetic frequency generator configured to apply pulsed electromagnetic field to at least a portion of said mucosal region; and
a plurality of pairs of electrodes in communication with an RF tissue diathermy device;
wherein at least one temperature sensor is adjacent to at least a portion of at least one electrode in said plurality of pairs of electrodes
further wherein a region of tissue in proximity to at least one electrode of a pair of electrodes is at least temporarily maintained at a predetermined temperature range $T_1$ while another region of tissue in proximity to at least one electrode of another pair of electrodes is at least temporarily maintained at predetermined temperature range $T_2$, where $T_1$ is equal to or different from $T_2$.

It is another object of the present invention to provide the device, wherein said mucosal region is within a vagina.

It is another object of the present invention to provide the device as defined above, wherein the at least one temperature sensor is selected from a group consisting of: a thermistor, a thermocouple and any combination thereof.

It is another object of the present invention to provide the device, additionally comprising a database configured to store at least one temperature profile, said temperature profile comprising at least one temperature and at least one portion of said mucosal region.

It is another object of the present invention to provide the device, additionally comprising a processor in communication with said at least one temperature sensor and with said database.

It is another object of the present invention to provide the device, wherein said processor is configured to feedback control output to said pulsed electromagnetic frequency generator and said RF tissue diathermy device such that said temperature profile is maintainable in at least one predetermined region outside said device.

It is another object of the present invention to provide the device, wherein each said at least one temperature is measurable in said at least one portion of said mucosal region.

It is another object of the present invention to provide the device, wherein said heating mechanism is selected from a group consisting of: tissue diathermy, sound waves absorbable by tissue, heated fluid, optical radiation at wavelengths absorbable by tissue, electric current, an inductive electromagnetic field and any combination thereof.

It is another object of the present invention to provide the device, wherein a pulse shape of said pulsed electromagnetic power is selected from a group consisting of: square wave, triangular wave, sawtooth wave, ramp wave, spiked wave and any combination thereof.

It is another object of the present invention to provide the device, wherein a duration of a pulse of said pulsed electromagnetic power is in a range between about 3 ms and about 1000 ms.

It is another object of the present invention to provide the device, wherein a frequency F of said pulses of said pulsed electromagnetic power is in a range between about 1 Hz and about 1 MHz.

It is another object of the present invention to provide the device, wherein said pulsed electromagnetic power is configured to induce angiogenesis.

It is another object of the present invention to provide the device, wherein said pulsed electromagnetic power is configured to stimulate collagen production.

It is another object of the present invention to provide the device, wherein said pulsed electromagnetic power comprises pulses at a frequency F between about 10 Hz and about 25 Hz and intensity I of about 20 gauss.

It is another object of the present invention to provide the device, wherein said at least one temperature in said temperature profile is in a range from about 30 degrees C. to about 80 degrees C.

It is another object of the present invention to provide the device, wherein said at least one temperature in said temperature profile is in a range from about 40 degrees C. to about 50 degrees C.

It is another object of the present invention to provide an integrated system for increasing rejuvenation of a region of a patient's mucosa, said system comprising:

at least two electrodes configured to be placed on said region of said patient's mucosa;

an electromagnetic field generator configured to generate electromagnetic field pulses; and, a control system;

wherein:

none of said at least two electrodes is configured to penetrate said mucosa;

each of said at least two electrodes is configured to conduct RF to said region of a patient's mucosa;

each of said at least two electrodes is configured to apply heat to heat tissue up to a temperature T in a range of 30 degrees Celsius to 80 degrees Celsius;

said control system is configured to control said electromagnetic field generator and application of said heat by said electrodes; and, all of said at least two electrodes are configured to simultaneously provide said electromagnetic pulses to said region of a patient's mucosa and to apply said heat to said region of a patient's mucosa further wherein at least one tissue region is at least temporarily maintained at a predetermined temperature range $T_1$ while at least one other tissue region is at least temporarily maintained at predetermined temperature range $T_2$, where $T_1$ is either equal to or different from $T_2$.

It is another object of the present invention to provide the integrated system, wherein said mucosal region is within a vagina.

It is another object of the present invention to provide an integrated system, additionally comprising a database configured to store at least one temperature profile, said temperature profile comprising at least one temperature and at least one portion of said mucosal region.

It is another object of the present invention to provide an integrated system, additionally comprising a processor in communication with said at least one temperature sensor and with said database, said at least one temperature sensor being adjacent to at least a portion of at least one electrode in said at least two electrodes.

It is another object of the present invention to provide the device as defined above, wherein the at least one temperature sensor is selected from a group consisting of: a thermistor, a thermocouple and any combination thereof.

It is another object of the present invention to provide an integrated system, wherein said processor is configured to feedback control output to said pulsed electromagnetic frequency generator and said RF tissue diathermy device such that said temperature profile is maintainable in at least one predetermined region outside said device.

It is another object of the present invention to provide an integrated system, wherein each said at least one temperature is measurable in said at least one portion of said mucosal region.

It is another object of the present invention to provide an integrated system, wherein said heat applied to said region of a patient's mucosa is obtained by a member of a group consisting of: RF tissue diathermy, emitting RF radiation, via producing electrical current absorbed by tissue and any combination thereof.

It is another object of the present invention to provide an integrated system, wherein said electromagnetic pulses are selected from a waveform with a frequency between about 10 Hz and about 25 Hz and intensity of 20 gauss or a waveform with a frequency of 15 Hz, duration of about 5 ms and intensity of 12 gauss.

It is another object of the present invention to provide an integrated system, wherein said system is configured to provide a dynamic magnetic field such that said electromagnetic pulses vary with time.

It is another object of the present invention to provide an integrated system, wherein each of said electromagnetic pulses has a shape selected from the group consisting of a square wave, a sine wave, a triangular wave, a sawtooth wave, a ramp wave, a spiked wave and any combination thereof.

It is another object of the present invention to provide an integrated system, wherein said control system (6) monitors physical tissue parameters and changes said applied heat and said electromagnetic pulses accordingly.

It is another object of the present invention to provide an integrated system, wherein a duration of each pulse applied by said system ranges between about 3 ms and about 1000 ms.

It is another object of the present invention to provide an integrated system, wherein a frequency F applied by the pulses of said system ranges between about 1 Hz and about 1 MHz.

It is another object of the present invention to provide an integrated system, wherein a power P applied by the pulses of said system ranges between about 1 W and about 150 W of RMS average power.

It is another object of the present invention to provide a system (10) configured to increase rejuvenation of a region of a patient's mucosa by synergistic application of heat and a pulsed electromagnetic field (PEMF) to a region of a patient's mucosa, said system comprising:
   a. a pulsed electromagnetic field generator for generating a pulsed electromagnetic field (PEMF) (2) for providing electromagnetic pulses to said region of said patient's mucosa according to a predetermined protocol chosen from a group consisting of:
      i. a series of pulses with a frequency between about 10 Hz and about 25 Hz and an intensity of about 20 gauss;
      ii. a series of pulses of duration of about 5 ms and intensity of about 12 gauss, repeated at a frequency of about 15 Hz; and
      iii. any combination thereof;
   b. an RF tissue diathermy device (4) configured to apply heat to said region of said patient's mucosa up to a temperature of 80 degrees Celsius; and
   c. an electromagnetic pulse regulator (6) configured to regulate said electromagnetic pulses, said control system comprising:
      i. processing parameter storage means for storing in a communicable database predetermined parameters defining (i) safe treatment parameters and (ii) unsafe treatment parameters; said communicable database predetermined parameters are selected from the group consisting of time of said treatment, temperature of said tissue, duty cycle of time on/total time, frequency, power applied by the pulses of said pulsed electromagnetic frequency generator, depth of said treated tissue, magnetic field intensity, tissue impedance, specific absorption rate (SAR), treatment depth, superficial muscle contractions or a combination thereof;
      ii. electromagnetic and heat radiation sensing means for sensing electromagnetic radiation and heat radiation parameters selected from the group consisting of a time of said treatment, temperature of said tissue, duty cycle of time on/total time, frequency, intensity of said ultrasound irradiation, power applied by the pulses of said pulsed electromagnetic frequency generator, depth of said treated tissue, magnetic field intensity, tissue impedance, specific absorption rate (SAR), treatment depth, superficial muscle contractions or a combination thereof; and
      iii. regulating electromagnetic and heat radiation regulation means for allowing said electromagnetic radiation and heat radiation if said electromagnetic radiation and heat radiation parameters are within said safe treatment parameters and to stop the electromagnetic radiation if the radiation parameters are in said unsafe treatment parameters;
wherein said system is configured to provide mucosal rejuvenation via a synergistic combination of PEMF and RF tissue diathermy,
wherein said system further comprises at least two electrodes (41) configured to be placed on said region of a patient's mucosa,
wherein each of said electrodes is configured for both (i) providing electromagnetic pulses to said region of said patient's mucosa; and, (ii) applying heat up to temperature 80 degrees Celsius to said region of a patient's mucosa, and wherein all of said electrodes are configured to simultaneously provide said electromagnetic pulses to said region of said patient's mucosa and to apply heat to said region of said patient's mucosa.

It is another object of the present invention to provide the system, wherein said mucosal region is within a vagina.

It is another object of the present invention to provide the system, wherein a tissue region in proximity to at least one said electrode is at least temporarily maintained at a predetermined temperature range $T_1$ while another tissue region in proximity to another at least one said electrode is at least temporarily maintained at predetermined temperature range $T_2$, where $T_1$ is equal to or different from $T_2$.

It is another object of the present invention to provide the system, wherein said mucosal region is within a vagina.

It is another object of the present invention to provide the system, additionally comprising a database configured to store at least one temperature profile, said temperature profile comprising at least one temperature and at least one portion of said mucosal region.

It is another object of the present invention to provide the system, additionally comprising a processor in communication with said at least one temperature sensor and with said database.

It is another object of the present invention to provide the system, wherein said processor is configured to feedback control output to said pulsed electromagnetic frequency generator and said RF tissue diathermy device such that said temperature profile is maintainable in at least one predetermined region outside said device.

It is another object of the present invention to provide the system, wherein each said at least one temperature is measurable in said at least one portion of said mucosal region.

It is another object of the present invention to provide the system, wherein said RF tissue diathermy device (4) is selected from any device emitting RF radiation or an electrical current producing means configured for producing electrical current absorbed by tissue, RF tissue diathermy, electromagnetic induction, and direct heat applying instrument.

It is another object of the present invention to provide the system, wherein said RF tissue diathermy device (4) additionally comprises:
   a. at least one electrical output device configured to generate either RF electromagnetic power or electrical current; and
   b. at least two electrodes electrically coupled to said electrical output device and placed on said mucosal region, wherein all said electrodes are configured to simultaneously apply said RF power or said electrical current to said mucosal region.

It is another object of the present invention to provide the system, wherein said pulsed electromagnetic frequency generator is configured to provide a dynamic magnetic field such that said electromagnetic pulses vary with time.

It is another object of the present invention to provide the system, wherein at least one condition is being held true (a) the shape of said electromagnetic pulse is selected from the group consisting of square wave, a sine wave, a triangular wave, sawtooth wave, ramp waves, spiked wave or any combination thereof; (b) the duration of each pulse applied by said pulsed electromagnetic frequency generator (2) ranges between about 3 ms and about 1000 ms; (c) the frequency applied by the pulses of said pulsed electromagnetic frequency generator (2) ranges between about 1 Hz and about 1 MHz; (d) the power applied by the pulses of said pulsed electromagnetic frequency generator (2) ranges between about 1 W and about 150 W of RMS average power or any combination thereof.

It is another object of the present invention to provide the system, wherein at least one condition is being held true: an optical device is configured to emit light in wavelengths absorbed by tissue such that said tissue is heated; a sound waves emitting instrument is configured to emit sound waves absorbed by the tissue such that said tissue is heated, RF tissue diathermy is applied such that said tissue is heated, and any combination thereof.

It is another object of the present invention to provide the system, wherein said temperature is higher than about 30 degrees Celsius and lower than about 80 degrees Celsius.

It is another object of the present invention to provide the system, wherein a power supply and control system (6) includes a mucosa cooling means for cooling the mucosa.

It is another object of the present invention to provide the system, wherein said system (10) is encased in at least one platform.

It is another object of the present invention to provide the system, wherein said pulsed electromagnetic frequency generator (2) and said RF tissue diathermy device (4) have more than one applicator to treat more than one body part simultaneously; further wherein said pulsed electromagnetic frequency generator (2) has electrostatic shielding.

It is another object of the present invention to provide the system, wherein said system is configured to operate according to an IEC protocol selected from the group consisting of IEC 60601-2-33, IEC 60601-2-5, IEC 60601-2-3, IEC 60601-1-8, IEC 60601-1-6, IEC 60601-1-4, IEC 60601-1-2, IEC 60601-1-1, and any combination thereof.

It is another object of the present invention to provide a method (400) of increasing mucosal rejuvenation of at least one region of a patient's mucosal tissue, comprising steps of:
 a. obtaining (i) pulsed electromagnetic frequency generator; and (ii) an tissue diathermy device; and,
 b. applying either simultaneously or in batch like manner
  (a) heat to a tissue within said region up to temperature T; or (b) pulses of electromagnetic field to said region; and any combination thereof wherein said increasing of said mucosal rejuvenation is greater than the sum of rejuvenation due to said applying heat to a tissue within said region and rejuvenation due to said applying pulses electromagnetic therapy to said region further wherein at least one said region of a patient's mucosal tissue is at least temporarily maintained at a predetermined temperature range $T_1$ while at least one other region of a patient's mucosal tissue is at least temporarily maintained at predetermined temperature range $T_2$, where $T_1$ is equal to or different from $T_2$.

It is another object of the present invention to provide the method, additionally comprising step of selecting said at least one region of mucosal region to be within a vagina.

It is another object of the present invention to provide the method, additionally comprising steps of: (a) providing a database comprising a temperature profile, said temperature profile containing at least one temperature and at least one predetermined region; (b) measuring said at least one temperature at said at least one predetermined region; and (c) feedback controlling output to said pulsed electromagnetic frequency generator and said tissue diathermy device, thereby maintaining said temperature profile in said at least one predetermined region.

It is another object of the present invention to provide the method, additionally comprising steps of (a) providing a vaginal treatment device comprising a distal portion and a proximal portion, said distal portion and said proximal portion reversibly connectible; said proximal portion in communication with a member of a group consisting of said pulsed electromagnetic frequency generator, said tissue diathermy device and any combination thereof; said distal portion comprising at least two electrodes; (b) placing said distal portion at least partially within said vagina; (c) keeping at least a part of said distal portion substantially stationary within said vagina for a time period in a range between about 1 minute and about 20 minutes; (d) for at least a portion of said time period, activating a member of a group consisting of said pulsed electromagnetic frequency generator, said tissue diathermy device and any combination thereof, said activation applying a member of a group consisting of pulsed electromagnetic field, heat and any combination thereof to tissue in said vagina; and (e) for at least a portion of said time period, measuring temperature of said tissue in said vagina.

It is another object of the present invention to provide the method, additionally comprising steps of (a) providing said distal portion with at least two pairs of electrodes; and (b) controlling each pair separately, thereby maintaining said temperature profile within at least a portion of said vagina.

It is another object of the present invention to provide the method, additionally comprising step selected from a group consisting of: simultaneously applying said pulsed electromagnetic field and said heat, sequentially applying said pulsed electromagnetic field and said heat and any combination thereof.

It is another object of the present invention to provide the method, wherein said step of applying heat to a tissue additionally comprises steps of:
 a. obtaining at least one electrical output device configured to generate either RF electromagnetic power or electrical current;
 b. electrically coupling at least two electrodes to said electrical output device;
 c. placing said at least two electrodes on said skin or mucosal tissue region; and,
 d. applying via at least one said electrode a member of a group consisting of said RF power, said electrical current and any combination thereof to said skin or mucosal tissue region.

It is another object of the present invention to provide the method, wherein said system reduces side effects and/or harmful effects of said electromagnetic pulses and/or said tissue diathermy such that said reduction of said side effects and/or said harmful effects is greater than the sum of said reduction due to said electromagnetic pulses and said reduction due to said tissue diathermy.

It is another object of the present invention to provide the method, additionally comprising a step of monitoring and/or controlling said steps of applying heat to a tissue within said region and/or said step of applying pulsed electromagnetic therapy to said region.

It is another object of the present invention to provide the method, additionally comprising a step of applying a dynamic magnetic field onto said region.

It is another object of the present invention to provide the method, additionally comprising steps of:
 a. storing in a communicable database predetermined parameters defining (i) safe treatment parameters and (ii) unsafe treatment parameters; said parameters are selected from a group consisting of: total duration time $t_t$ of said treatment, time during which pulses of electromagnetic field are applied $t_p$, temperature T of said tissue, duty cycle $t_p/t_t$, frequency F, power P applied by the pulses of said pulsed electromagnetic frequency generator, depth D of said treated tissue, magnetic field intensity B, tissue impedance, specific absorption rate (SAR), treatment depth, superficial muscle contractions and any combination thereof;
 b. sensing electromagnetic radiation and heat radiation parameters selected from a group consisting of total duration time $t_t$ of said treatment, time during which pulses of electromagnetic field are applied $t_p$, temperature T of said tissue, duty cycle $t_p/t_t$, frequency F, power P applied by the pulses of said pulsed electromagnetic frequency generator, intensity I of said ultrasound irradiation, depth D of said treated tissue, magnetic field intensity B, tissue impedance, specific absorption rate (SAR), treatment depth, superficial muscle contractions and any combination thereof;
 c. allowing said electromagnetic radiation and said heat radiation if said parameters are within said safe treatment parameters and stopping said electromagnetic radiation and said heat radiation if said radiation parameters are in said unsafe treatment parameters.

It is another object of the present invention to provide the method, additionally comprising a step of selecting a shape of said electromagnetic pulse from a group consisting of: square wave, sine wave, triangular wave, sawtooth wave, ramp wave, spiked wave and any combination thereof.

It is another object of the present invention to provide the method, additionally comprising a step of applying at least one selected from a group consisting of (a) an electromagnetic pulse at frequency of about 10-25 Hz and intensity of about 20 gauss; (b) an electromagnetic pulse at a frequency of about 15 Hz, duration of about 5 ms and intensity of about 12 gauss.

It is another object of the present invention to provide the method, additionally comprising a step of applying a series of electromagnetic pulses, said series of electromagnetic pulses comprising recurring applications of a pattern comprising a preset number of square wave pulses of duration of about 1 μs with a duty cycle of about 50% followed by a pause of not more than about 250 μs. In other variants of this step, the pulses have a shape selected from any disclosed herein and a duration of about 1 μs with a duty cycle of about 50% followed by a pause of not more than about 250 μs.

It is another object of the present invention to provide the method, additionally comprising a step of applying a series of electromagnetic pulses, said series of electromagnetic pulses comprising recurring applications of a pattern comprising about 10 square pulses of duration of about 1 μs with a duty cycle of about 50% followed by a pause of not more than about 512 μs. In other variants of this step, the series of electromagnetic pulses comprises recurring applications of a pattern comprising about 10 pulses of duration of about 1 μs with a duty cycle of about 50% followed by a pause of not more than about 512 μs, where the pulses the pulses have a shape selected from any disclosed herein.

It is another object of the present invention to provide the method, additionally comprising a step of selecting said tissue diathermy device from a group consisting of: a device emitting RF radiation, a device inducing electromagnetic field within tissue and any combination thereof.

It is another object of the present invention to provide the method, wherein said step of applying heat to a tissue additionally comprises steps of:
 a. obtaining at least one electrical output device configured to generate either RF electromagnetic power or electrical current;
 b. electrically coupling at least two electrodes to said electrical output device;
 c. placing said at least two electrodes on said mucosal region; and,
 d. applying via at least one said electrode at least one of said RF power and said electrical current to said mucosal region.

It is another object of the present invention to provide the method, additionally comprising a step of selecting at least one parameter from a group consisting of (a) the duration of each pulse applied by said pulsed electromagnetic frequency generator (2) to be greater than about 3 ms and lower than about 1000 ms; (b) the frequency F applied by the pulses applied by said step of applying pulsed electromagnetic therapy to said region to be higher than about 1 Hz and lower than about 1 MHz; (c) the power P applied by said step of applying pulsed electromagnetic therapy to said region to be greater than about 1 W and lower than about 150 W of RMS average power.

It is another object of the present invention to provide the method, wherein step of applying heat is applied for about 0.01 minutes to about 60 minutes.

It is another object of the present invention to provide the method, wherein the heat and the pulsed electromagnetic therapy are applied simultaneously, sequentially or separately.

It is another object of the present invention to provide the method, wherein said step of applying heat is performed by devices selected from a group consisting of: RF tissue diathermy, ultrasonic diathermy, an optical device, electromagnetic induction, sound wave emitting instrument, direct heat applying instrument, and any other means of heating tissue to temperature T.

It is another object of the present invention to provide an integrated system for increasing rejuvenation of at least one region of a patient, said region selected from a group consisting of said patient's skin, said patient's mucosal tissue and any combination thereof, said system comprising:
 at least two electrodes configured to be placed on said at least one region;
 an electromagnetic field generator configured to generate electromagnetic field pulses; and
 a control system;
wherein:
 none of said at least two electrodes is configured to penetrate said region of said patient;
 each of said at least two electrodes is configured to provide electromagnetic pulses to said region of said patient, each of said at least two electrodes is configured to heat at least one said region up to a temperature T in a range of about 30 degrees C. to about 80 degrees C.;

said control system is configured to control a member of a group consisting of: said electromagnetic field generator, application of heat by said electrodes and any combination thereof; and, each of said at least two electrodes is configured to provide said electromagnetic pulses to at least one said region and to apply said heat to at least one said region in a manner selected from a group consisting of: simultaneously, sequentially and any combination thereof.

It is another object of the present invention to provide the integrated system, wherein at least one said region in proximity to at least one of said at least two electrodes is at least temporarily maintained at a predetermined temperature range $T_1$ while another at least one said region in proximity to at least one other of said at least two electrodes is at least temporarily maintained at predetermined temperature range $T_2$, where $T_1$ is equal to or different from $T_2$.

It is another object of the present invention to provide the integrated system, wherein said at least one region is within a vagina.

It is another object of the present invention to provide the integrated system, additionally comprising a database configured to store at least one temperature profile, said temperature profile comprising at least one temperature and at least one portion of said at least one region.

It is another object of the present invention to provide the integrated system, additionally comprising a processor in communication with at least one temperature sensor and with said database.

It is another object of the present invention to provide the integrated system, wherein said processor is configured to feedback control output to said pulsed electromagnetic frequency generator and said tissue diathermy device such that said temperature profile is maintainable in at least one predetermined region outside said device.

It is another object of the present invention to provide the integrated system, wherein each said at least one temperature is measurable in said at least one portion of said region of said patient.

It is another object of the present invention to provide the integrated system, wherein said heat applied to said region of said patient is obtained by a member of a group consisting of: RF tissue diathermy, emitting RF radiation, via producing electrical current absorbed by tissue and any combination thereof.

It is another object of the present invention to provide the integrated system, wherein said electromagnetic pulses are selected from a waveform with a frequency of about 10-25 Hz and intensity of 20 gauss or a waveform with a frequency of 15 Hz, duration of about 5 ms and intensity of 12 gauss.

It is another object of the present invention to provide the integrated system, wherein said system is configured to provide a dynamic magnetic field such that said electromagnetic pulses vary with time.

It is another object of the present invention to provide the integrated system, wherein each of said electromagnetic pulses has a shape selected from the group consisting of: a square wave, a sine wave, a triangular wave, a sawtooth wave, a ramp wave, a spiked wave and any combination thereof.

It is another object of the present invention to provide the integrated system, wherein said control system (6) monitors physical tissue parameters and changes said applied heat and said electromagnetic pulses accordingly.

It is another object of the present invention to provide the integrated system, wherein a duration of each pulse applied by said system ranges between about 3 ms and about 1000 ms.

It is another object of the present invention to provide the integrated system, wherein a frequency F applied by the pulses of said system ranges between about 1 Hz and about 1 MHz.

It is another object of the present invention to provide the integrated system, wherein a power P applied by the pulses of said system ranges between about 1 W and about 150 W of RMS average power.

BRIEF DESCRIPTION OF THE DRAWINGS

In order to understand the invention and to see how it may be implemented in practice, a few preferred embodiments will now be described, by way of non-limiting example only, with reference to the accompanying drawings, in which.

DETAILED DESCRIPTION

Figure 1A:
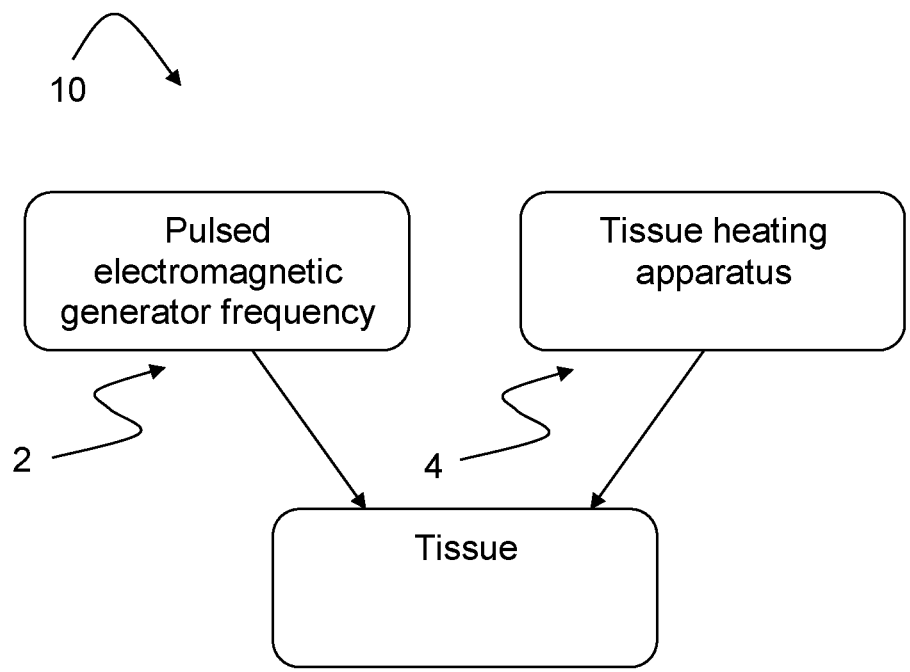
FIGS. 1A-1D schematically present a mucosa viability improving system, comprising a pulsed electromagnetic frequency generator and a tissue diathermy device.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and method for increasing the viability of the mucosa and for treating tissue lesions. Yet more the present invention provides means and system for mucosal tightening and rejuvenation.

It is one object of the present invention to disclose a device used to improve mucosal viability, by a synergistic approach of tissue diathermy combined with application of PEMF, wherein at least two devices of tissue diathermy are incorporated, one of them based on PEMF therapy. The latter improves the healing process initiated by the at least one other device of tissue diathermy.

The term "Pulsed Electromagnetic Fields (PEMF)" refers hereinafter in a non-limiting manner to electromagnetic radiation of different frequencies—ranging from static magnetic fields, through extremely low frequencies (ELF) to radiofrequencies (RF)—administered in pulses.

The term "Radio Frequency (RF)" refers hereinafter in a non-limiting manner to part of the electromagnetic spectrum with frequency range of about 3 Hz to 300 GHz.

The term "Extremely Low Frequencies (ELF)" refers hereinafter in a non-limiting manner to part of the RF electromagnetic spectrum with frequency range of about 3 Hz to 30 GHz.

The term "collagen" refers hereinafter in a non-limiting manner to a long, fibrous structural protein which is a major component of the extracellular matrix that supports most tissues and gives cells structure. It is responsible for mucosal strength and elasticity, and its degradation leads to wrinkles that accompany aging.

The term "epidermis" refers hereinafter in a non-limiting manner to the outermost layer of the mucosa.

The term "dermis" refers hereinafter in a non-limiting manner to a layer of tissue beneath the epidermis that consists of connective tissue, and cushions the body from stress and strain.

The term "tissue diathermy" or "deep tissue diathermy" refers hereinafter in a non-limiting manner to a device which heats tissues beneath the epidermis.

The term "electric diathermy" refers hereinafter in a non-limiting manner to a device which uses high frequency alternating electric or magnetic fields, sometimes with no electrode or device contact to the mucosa, to induce gentle deep tissue heating by induction. For collagen fiber stimulation, typical electrical parameters may include, in a non-limiting manner, frequency of about 1 MHz, energy of about 80 J per square cm tissue volume, applied for about 6 s.

The term "ultrasonic diathermy" refers hereinafter in a non-limiting manner to heating of tissues by ultrasound.

The term "about" refers hereinafter to a range of 25% below or above the referred value.

The term "physical tissue parameters" refers hereinafter to parameters such as tissue temperature, electric current, tissue impedance, specific absorption rate (SAR), treatment depth and superficial muscle contractions.

The term "angiogenesis" refers hereinafter to the generation of new blood vessels.

The term "square wave" refers hereinafter to a non-sinusoidal waveform named for its square shape.

The term "triangular wave" refers hereinafter to a non-sinusoidal waveform named for its triangular shape.

The term "International Electrotechnical Commission Standards (IEC) 60601-1" refers hereinafter to a medical electrical equipment standard. More specifically it refers to general requirements for basic safety and essential performance.

The term "IEC 60601-1-1" refers hereinafter to medical electrical equipment standard. More specifically it refers to general requirements for safety—Collateral standard: Safety requirements for medical electrical systems. The IEC 60601-1 set of standards are divided into three distinct areas. The first area is the basic standard IEC 60601-1. This is the general requirement for all electrical medical based products. The second area is the collateral standards, which cover across the board issues such as combining into a system with other devices, EMC, radiation protection, and programmable electronic medical systems (software, firmware, etc.). The standard numbers are IEC 60601-1-1, -1-2, -1-3, and -1-4 respectively. The third area is the particular standards that deal with a specific type of medical device. The particular standards are identified as IEC 60601-2-XX where XX identifies the particular standard number for the particular type of medical equipment. An example would be IEC 60601-2-3 which is the particular standard for short-wave therapy equipment.

The term "IEC 60601-1-2" refers hereinafter to medical electrical equipment standard. More specifically it refers to general requirements for basic safety and essential performance—Collateral standard: Electromagnetic compatibility—Requirements and tests.

The term "IEC 60601-1-3" refers hereinafter to medical electrical equipment standard. More specifically it refers to general requirements for basic safety and essential performance—Collateral Standard: Radiation protection in diagnostic X-ray equipment.

The term "IEC 60601-1-4" refers hereinafter to medical electrical equipment standard. More specifically it refers to general requirements for safety—Collateral Standard: Programmable electrical medical systems.

The term "IEC 60601-1-6" refers hereinafter to medical electrical equipment standard. More specifically it refers to general requirements for basic safety and essential performance—Collateral standard: Usability.

The term "IEC 60601-1-8" refers hereinafter to medical electrical equipment standard. More specifically it refers to general requirements for basic safety and essential performance—Collateral Standard: General requirements, tests and guidance for alarm systems in medical electrical equipment and medical electrical systems.

The term "IEC 60601-2-3" refers hereinafter to medical electrical equipment standard. More specifically it refers to particular requirements for the safety of short-wave therapy equipment.

The term "IEC 60601-2-5" refers hereinafter to medical electrical equipment standard. More specifically it refers to particular requirements for the safety of ultrasonic physiotherapy equipment.

The term "IEC 60601-2-9" refers hereinafter to medical electrical equipment. More specifically it refers to particular requirements for the safety of patient contact dosimeters used in radiotherapy with electrically connected radiation detectors.

The term "IEC 60601-2-29" refers hereinafter to medical electrical equipment standard. More specifically it refers to particular requirements for the basic safety and essential performance of radiotherapy simulators.

The term "IEC 60601-2-33" refers hereinafter to medical electrical equipment standard. More specifically it refers to particular requirements for the safety of magnetic resonance equipment for medical diagnosis.

The term "IEC 60601-2-35" refers hereinafter to medical electrical equipment standard. More specifically it refers to particular requirements for the safety of blankets, pads and mattresses intended for heating in medical use.

The present invention relates to a physical therapeutic methods and systems. In such systems, a dynamic electromagnetic pulse and electromagnetic heating systems are incorporated together to accomplish physical therapy, especially mucosal tightening and rejuvenation.

The present invention provides a system configured to increase rejuvenation of a region of a patient's skin or mucosa. The system comprising in a non-limiting manner the following:
  a. a pulsed electromagnetic field (PEMF) frequency generator (2) for constantly providing electromagnetic pulses to the region of the patient's skin or mucosa or a combination thereof; and,
  b. a tissue diathermy device (4), preferably an RF tissue diathermy device, applying heat to the region of the patient's skin or mucosa or a combination thereof, thereby heating the patient's tissue to a temperature T.

The system (10) is configured for simultaneously application of heat and PEMF to said region of a patient's skin or mucosa or a combination thereof. Furthermore, the system increases the tissue rejuvenation such that the increase is greater than the sum of the increase due to the electromagnetic pulses increase and the increase due to the tissue diathermy.

Furthermore the system reduces side effects and/or harmful effects of the electromagnetic pulses and/or said tissue diathermy such that the reduction of side effects and/or harmful effects is greater than the sum of the reduction due to the electromagnetic pulses and the reduction due to the tissue diathermy.

It is another object of the present invention to provide an integrated system (20) configured to increase rejuvenation of a region of a patient's dermal tissue, in a skin region, in a mucosal region and any combination thereof. The system comprising at least two electrodes configured to be placed on or adjacent to, preferably immediately adjacent to, a region of a patient's tissue; each of the electrodes is at least partially coiled into a coil. It is emphasized that each of the electrodes is configured for both (i) providing electromagnetic pulses to the region of a patient's tissue; and, (ii) applying heat up to temperature T to the region of the patient's tissue. Furthermore, it is emphasized that all of the electrodes are configured to simultaneously conduct RF and thereby provide electromagnetic pulses to the region of a patient's tissue; and, apply heat up to temperature T to said region of a patient's tissue.

The decrease in the side effects of the tissue diathermy is at least partially a result of the healing effect of the pulsed electromagnetic frequency therapy.

Reference is now made to FIGS. 1A-1D, illustrating the system (10) for increasing mucosal rejuvenation. As described above, the system comprising a pulsed electromagnetic frequency generator (2) for providing electromagnetic pulses to the region of a patient's mucosa; and, a tissue diathermy device (4) configured to apply heat to the region of a patient's skin or mucosa up to temperature T.

It is emphasized that the system increases the rejuvenation of a patient's skin or mucosal tissue such that the increase is greater than the sum of the increase due to the electromagnetic pulses and the increase due to tissue diathermy.

By exposing the tissue (a region of a patient's skin or mucosa) to the combination of regulated heat and a pulsed electromagnetic field a synergistic effect is produced, whereby the rejuvenation in the tissue from the combination of regulated heat and a pulsed electromagnetic field is greater than would be expected from the sum of the improvements due to each treatment alone.

The present invention relies on 2 effects, the thermal effect and the electromagnetic pulse effect:

The thermal effects include heating the tissue to a temperature sufficiently high to produce tissue injury. Furthermore, when heat is generated within the dermis, it typically causes contraction and thickening of collagen fibers. Each of these will result in an overall tightened and rejuvenated mucosa.

Heat within the dermis creates a limited thermal injury. The body's natural response to this injury is to produce collagen at the site of the wound. This results in firmer, thicker, more youthful dermis. Usually the dermisis heated to temperatures below about 60 degrees C. for short periods of time. The thermal effects can be produced by:
  1. RF tissue diathermy;
  2. Optical means—by emitting light in wavelengths absorbed by tissue such as, but not limited to, subcutaneous tissue, such that the tissue is heated;
  3. Electrical means—by passing electrical current;
  4. Electromagnetic means, preferably in RF electromagnetic means—by transmitting electromagnetic fields to the dermal tissue, by inducing (by means of electromagnetic induction) electromagnetic fields in the tissue, or a combination of these mechanisms;
  5. Sound waves—specifically in the ultrasound frequencies;
  6. Physical means—such as massage or applying a warm substance adjacent to the surface of the tissue to be treated; and
  7. any combination thereof.

The electromagnetic pulses (either dynamic or static) can start the natural healing processes which occur in response to an injury (especially angiogenesis and generation of new collagen fibers via the release of tissue growth factors).

The electromagnetic field generates movements of charged molecules (ions) within the intercellular fluids. This movement generates heat which can enhance the thermal effects discussed earlier.

It is acknowledged that healing is the process by which cells in the body regenerate and repair to reduce the size of a damaged area. Healing incorporates both the removal of necrotic tissue (demolition), and the replacement of this tissue.

The replacement can happen in two ways:
  1. by regeneration: the necrotic cells are replaced by the same tissue as was originally there.
  2. by repair: injured tissue is replaced with scar tissue.

The Pulsed Electromagnetic Fields (PEMF) applied by the system (10), as described above, have no thermal effects and rely on tissue components and their reactions to the applied radiation. These reactions to the applied radiation can be due to a response of large charged molecules to specific frequencies and harmonics of those frequencies, charged small ions in the cell membranes affecting cell function and affecting cell reactions to hormones and chemical signals, charged small ions in the extracellular space and other, poorly understood, mechanisms.

Furthermore, applying the radiation in pulses was also found to have non-thermal effects. Yet more, only specific combinations of frequency, duty cycle and transmitted power achieve a specific tissue response.

It is now commonly accepted that electromagnetic fields (EMF) or PEMF are capable of initiating various healing processes and for treatment of pain and edema in superficial soft tissues; two decades ago, the FDA allowed the use of pulsed radiofrequency electromagnetic fields for treatment of pain and edema in [Rosch, P. J., Markov, M. S., eds. Bioelectromagnetic Medicine, Marcel Dekker, 2004; NY, 251-264].

The present invention utilizes PEMF combined with heating from a heat source which can be separate or can be integral to a device for cosmetic purposes as described above. The PEMF, as described above, when used at specific field intensities, duty cycles and frequencies, increases epidermal collagen synthesis. This newly formed collagen increases mucosal elasticity and rejuvenates the treated tissue. Furthermore, PEMF increases the degree of endothelial cell tubulization and proliferation, and augments angiogenesis primarily by stimulating endothelial release of FGF-2, inducing paracrine and autocrine changes in the surrounding tissue. Angiogenesis, the generation of new blood vessels, increases blood flow to the tissue, which in turn increases oxygen and nutritional substances delivery to the tissue. This effect is most beneficial for injured tissue, promoting rapid and improved healing. The growth factor released further enhances the healing process, both in quality and in speed of improvement.

The following provides a more detailed description of the two combined effects.

As disclosed earlier, the present invention discloses a system (10) which incorporates both regulated heating and electromagnetic pulses.

As described above, the heating can be produced by:
1. RF tissue diathermy;
2. Optical means—by emitting light in different wavelengths absorbed by tissue such as, but not limited to, subcutaneous tissue such that said tissue is heated.
3. Electrical means—by passing electrical current.
4. Electromagnetic means, preferably RF electromagnetic means—by transmitting or inducing (electromagnetic induction) an electromagnetic field on or in the treated tissue.
5. Sound waves—specifically in the ultrasound frequencies.
6. Physical means—such as massage, applying a warm substance to the surface of the treated tissue or placing a warm substance adjacent to the surface of the treated tissue, which can be skin or mucosa or a combination of both.

Figure 1B:
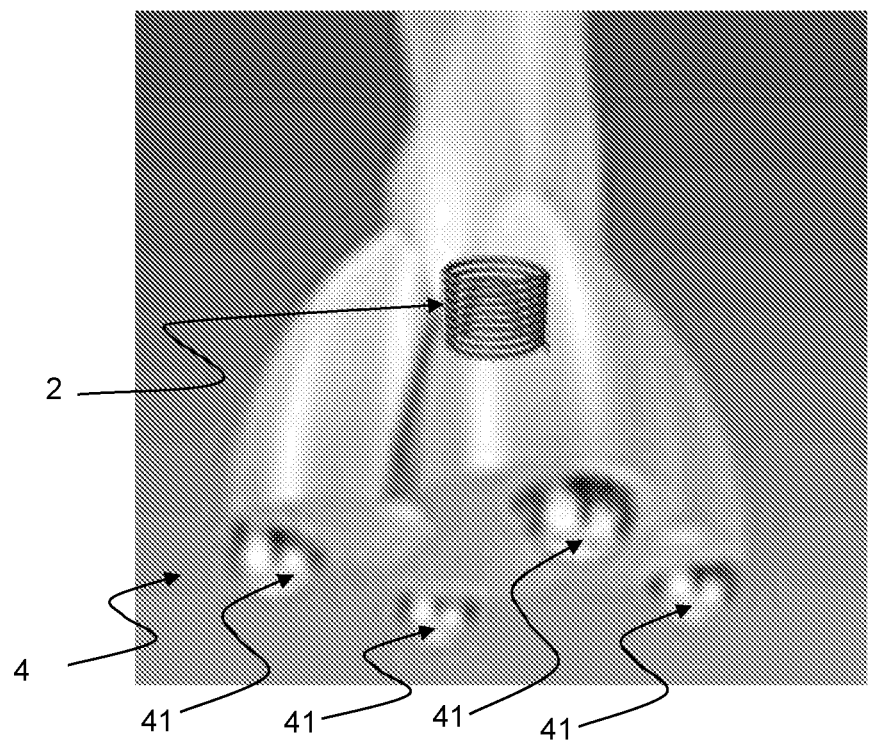
Figure 1C:
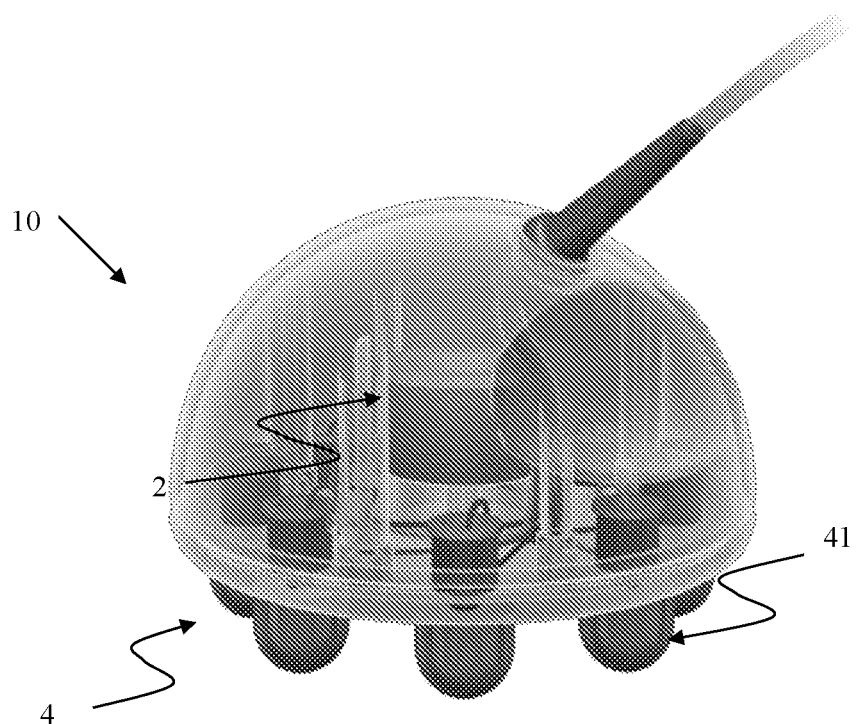
Figure 1D:
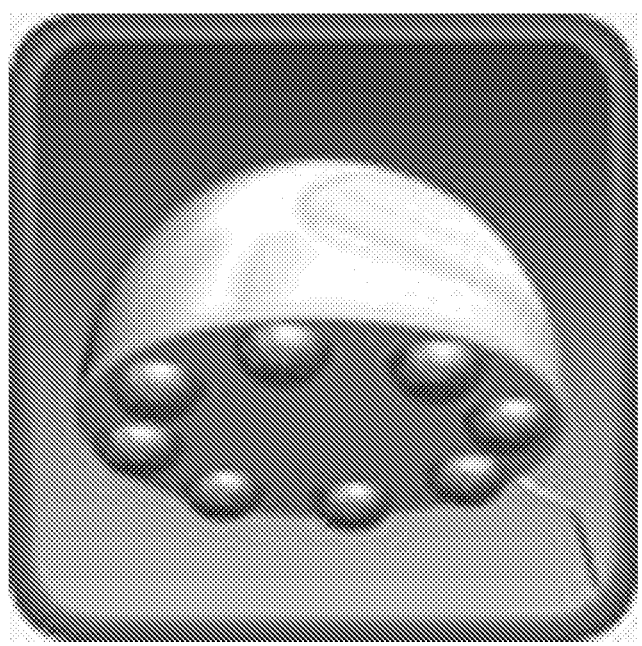

Reference is now made to FIGS. 1B-1D, illustrating the system (10) according to some embodiments of the present invention. These embodiments are intended to treat external skin.

According to these embodiments, the tissue diathermy device (4) comprises:
a. at least one electrical output device configured to generate electrical current; and,
b. at least two electrodes (41) electrically coupled to the electrical output device and placed on a skin region.

According to these embodiments all of the electrodes are configured to simultaneously apply electrical current to the skin region.

FIG. 1B illustrates a system (10) in which the tissue diathermy device (4) comprises 4 electrodes (41) and a coil for generating electromagnetic pulses (2). In other embodiments, no coil is used.

FIGS. 1C-1D illustrate a system (10) in which the tissue diathermy device (4) comprises 8 electrodes (41).

Figure 1E:
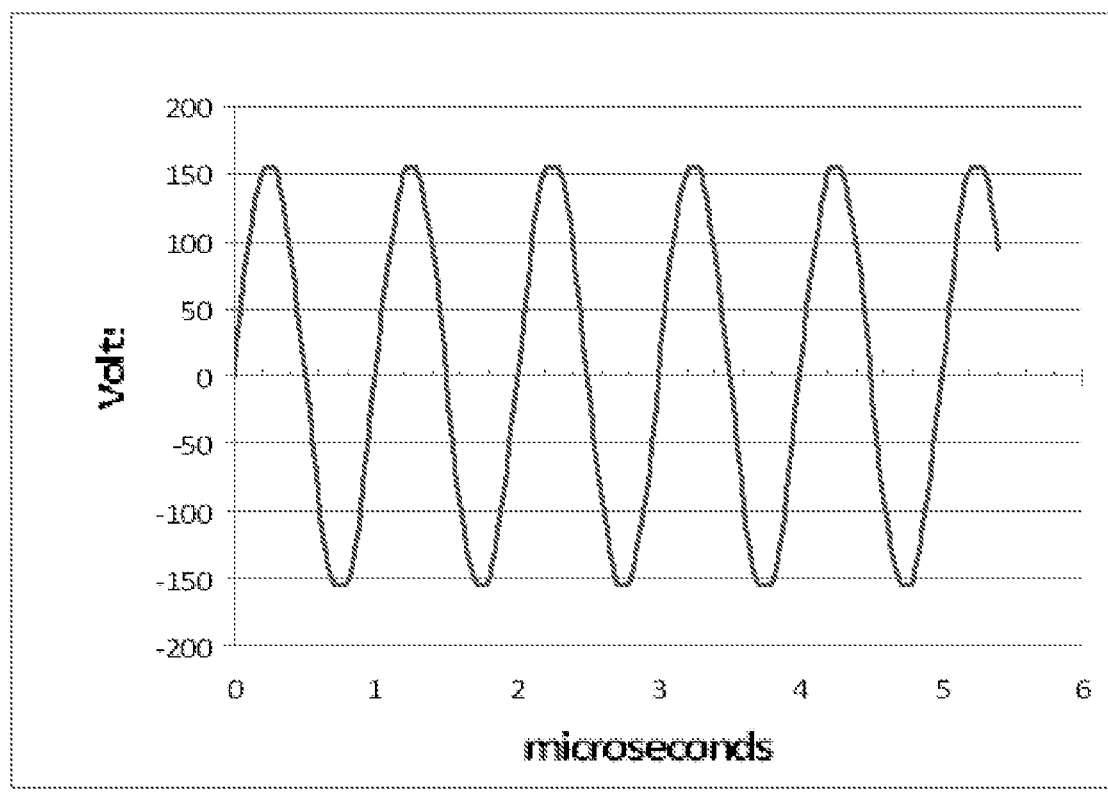
FIG. 1E is a diagram illustrating an example of electrical current applied by the tissue diathermy device.

Reference is now made to FIG. 1E, illustrating an example of electrical current applied by the tissue diathermy device (4). The current has a maximum amplitude of 160 volts, and a frequency close to 1 Hz.

In some embodiments of the present invention, the pulsed electromagnetic frequency generator is configured to provide an electromagnetic field where at least one of the frequency, the RMS average amplitude, the pulse width, and the duty cycle vary with time (dynamic electromagnetic field).

In some embodiments of the present invention, the pulsed electromagnetic frequency generator (2) which provides electromagnetic pulses to the patient's skin, mucosa and any combination thereof is positioned near the treated tissue and emits a dynamic magnetic field which varies with time. The dynamic magnetic field can vary according to any specific treatments. For example, to stimulate angiogenesis, pulses at a frequency of about 15 Hz, intensity of about 12 gauss and duration of about 5 ms are generated. Alternatively, to stimulate collagen production, pulses at a frequency of about 10-25 Hz and intensity of about 20 gauss are generated.

The tissue diathermy device (4) is configured to apply heat to the region of a patient's skin, mucosa and any combination thereof up to temperature T. According to some embodiments of the present invention, the heat is applied by passing RF electrical current through the tissue. The electrical current can be applied by any combination of the following:
1. through at least one electrode which is in direct physical contact with the skin, mucosa and any combination thereof;
2. through at least one electrode which is not in physical contact with the skin, mucosa and any combination thereof, and the electrical current is transferred by induction.
3. through at least one antenna which passes the electrical current to the skin, mucosa and any combination thereof via electromagnetic induction.

Figure 2:
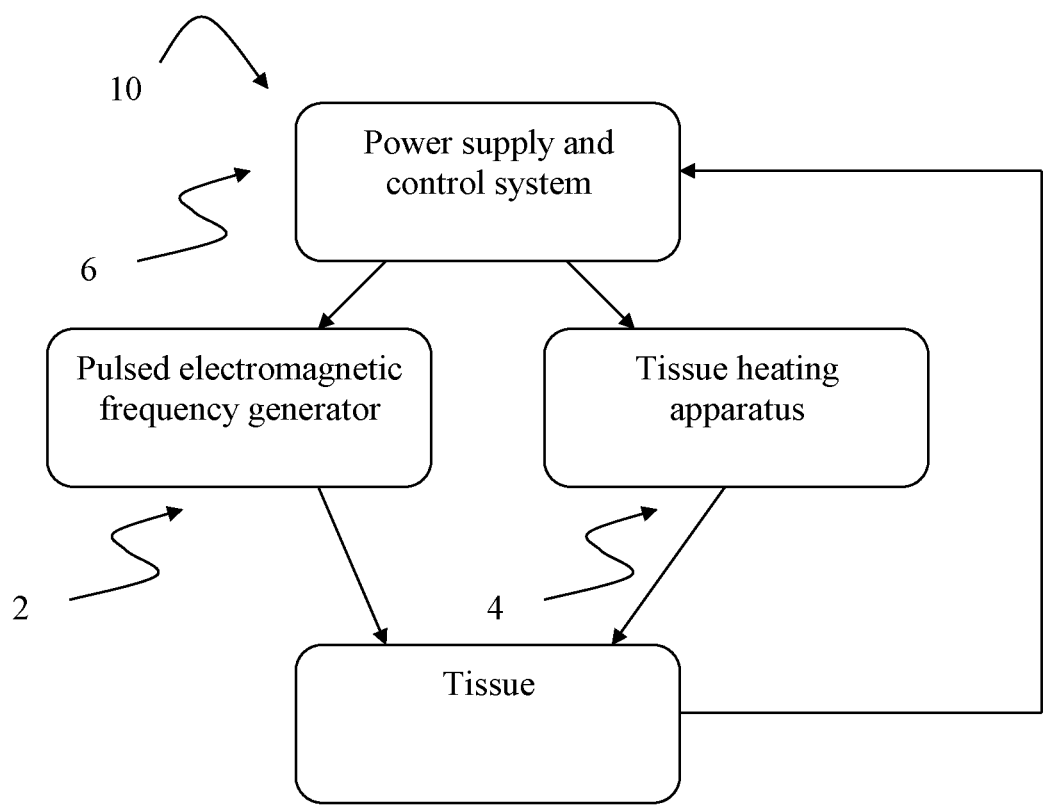
FIG. 2 schematically presents a mucosa viability improving system, comprising a pulsed electromagnetic frequency generator, a tissue diathermy device and a power supply and control system.

Reference is now made to FIG. 2, which illustrates an embodiment of the present invention, additionally comprising a control system (6) configured to regulate a member of a group consisting of: electromagnetic pulses, tissue diathermy and any combination thereof. In some embodiments of the present invention, treatment is provided only within safe treatment parameters.

Safe treatment parameters are defined by the parameters in table 1:

TABLE 1 safe treatment parameters

| Parameter | Value |
| --- | --- |
| Time, $t_o$ | 0-600 minutes |
| Temperature, T | 25-80 degrees C. |
| Duty cycle $t_p/t_t$ | 0-100% |
| PEMF frequency | DC-50 Hz |
| RF frequency | 200 kHz-10 MHz |
| Power P | 0-100 W |
| Energy E | 0-200 J |
| Magnetic field intensity B | 0-20 Gauss |
| Depth D of treated tissue | ≤30 mm |

Unsafe safe treatment parameters are defined by the parameters in table 2:

TABLE 2 unsafe treatment parameters

| Parameter | Value |
|---|---|
| Time, $t_t$ | >10 hours (nonstop) |
| Temperature, T | >80 degrees C. |
| Duty cycle $t_p/t_t$ | N/A |
| PEMF frequency | >10 MHz |
| RF frequency | >50 Hz |
| Power P | >100 W |
| Energy E | >200 J |
| magnetic field intensity B | >10 Gauss |
| Depth D of treated tissue | >30 millimeter |

In some embodiments, the control system (6) additionally comprises:
 a. a processor configured to store in a communicable database predetermined parameters defining (i) safe treatment parameters and (ii) unsafe treatment parameters, with the parameters selected from a group consisting of: total duration of a treatment $t_t$, time $t_p$ during which PEMF is applied, temperature T of the treated tissue, duty cycle $t_p/t_t$, frequency F, power P applied by the pulses from a pulsed electromagnetic frequency generator, intensity I of ultrasound diathermy, energy E applied by the pulses from a pulsed electromagnetic frequency generator, depth D of the treated tissue, magnetic field intensity B, tissue impedance, specific absorption rate (SAR), superficial muscle contractions and any combination thereof;
 b. a sensing mechanism configured to sense electromagnetic radiation and heating parameters selected from a group consisting of: time (duration) $t_t$ of a treatment, time $t_p$ during which electromagnetic radiation and/or heating is applied, temperature T of the treated tissue, duty cycle $t_p/t_t$, frequency F of the applied electromagnetic or heat radiation, power P applied by the pulses from a pulsed electromagnetic frequency generator, intensity I of RF tissue diathermy or other heating mechanism, energy E applied by the pulses from a pulsed electromagnetic frequency generator, depth D of the treated tissue, magnetic field intensity B, tissue impedance, specific absorption rate (SAR), superficial muscle contractions and any combination thereof;
 c. a regulation mechanism configured to allow pulsed electromagnetic radiation and the heating mechanism if parameters are within a range of safe treatment parameters and to stop at least one of the pulsed electromagnetic radiation and the heating mechanism if the parameters are within a range of unsafe treatment parameters.

In some embodiments, the system additionally comprises at least one sensor configured to monitor physical parameters selected from a group consisting of total duration of a treatment $t_t$, time $t_p$ during which PEMF is applied, temperature T of the treated tissue, duty cycle $t_p/t_t$, frequency F of the PEMF, power P applied by the pulses of the pulsed electromagnetic frequency generator, depth D of the treated tissue, magnetic field intensity B, tissue impedance, specific absorption rate (SAR), superficial muscle contractions and any combination thereof.

The at least one sensor receives at least one parameter from the treated tissue and changes at least one parameter of a member of a group consisting of: the pulsed electromagnetic frequency generator (2) and the tissue diathermy device (4) and any combination thereof, in order to optimize the effect of each component, to augment the synergistic effect of both components and any combination thereof, whilst avoiding harm to the tissue.

In some embodiments of the present invention, the shape of the electromagnetic pulse is selected in a non-limiting manner from a group consisting of: a square wave, a sine wave, a triangular wave, a sawtooth wave, a ramp wave, a spiked wave and any combination thereof.

In some embodiments, the system as defined above is configured to provide electromagnetic pulses at a frequency of about 15-16 Hz, with the pulse RMS average intensity varying over time between about 0 gauss and about 12 gauss. In some embodiments, the pulse RMS average intensity increases over time from about 0 gauss to about 12 gauss, then decreases over time to about 0, whereupon the cycle repeats. For non-limiting example, the rate of decrease of RMS amplitude can be approximately the same as the rate of increase, so that the time taken to decrease to 0 is approximately the same as the time taken to increase to maximum RMS average intensity. In some embodiments, the pulse RMS average intensity increases over time from about 0 gauss to about 12 gauss, then drops quickly, over no more than a few pulses, to about zero, whereupon the cycle repeats. In some variants of these embodiments, the intensity drops to zero over less than one pulse.

In some embodiments, the system as defined above is configured to provide electromagnetic pulses at a frequency of about 15-16 Hz, with the RMS average magnitude of the pulses repeatedly increasing from about 0 gauss to about 12 gauss.

Figure 3:
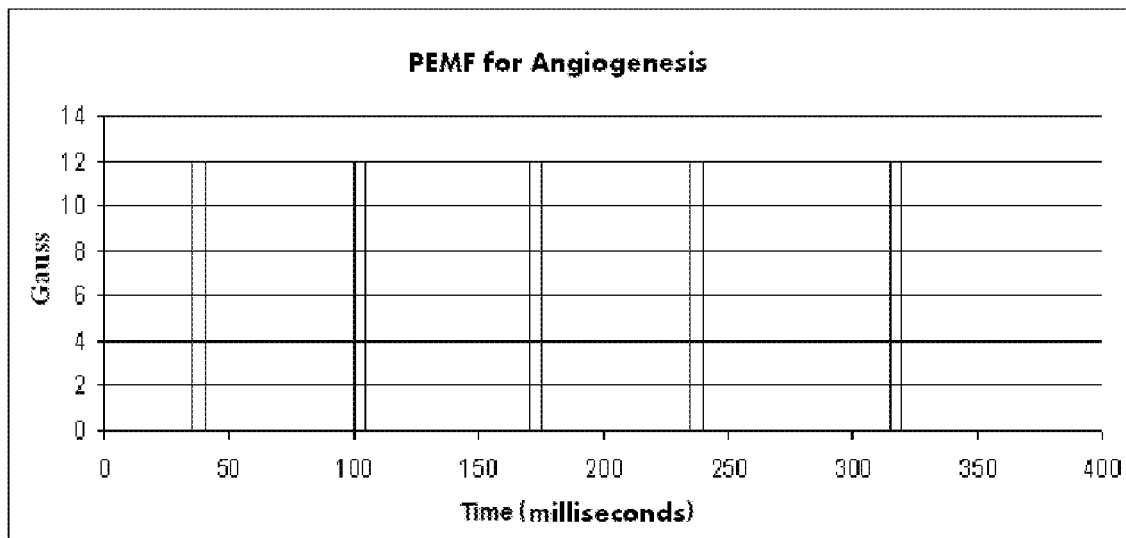
FIG. 3 schematically presents square waves which stimulate angiogenesis.

Reference is now made to FIG. 3, which illustrates an exemplary embodiment of square wave pulses configured to stimulate angiogenesis. In some embodiments configured to stimulate angiogenesis, the system as defined above is configured to provide pulses at a rate of about 15 Hz, with each pulse having a duration of about 5 ms, with an intensity of about 12 gauss. In some of these embodiments, the pulses are square waves. In other embodiments, the pulses can be of any pulse shape disclosed herein.

Figure 4:
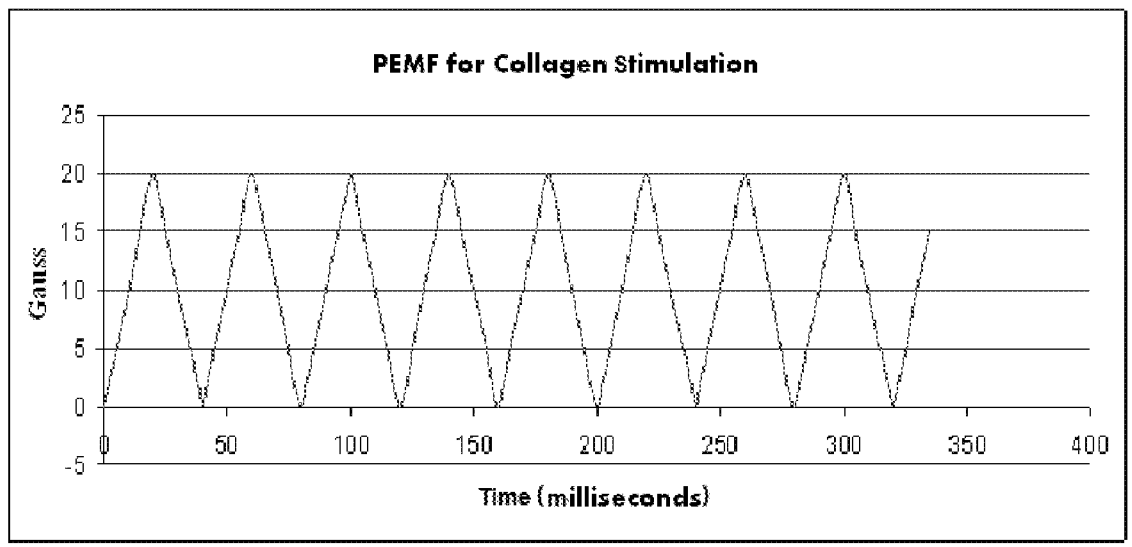
FIG. 4 schematically presents triangular wave pulses which can stimulate collagen production.

Reference is now made to FIG. 4, which illustrates an exemplary embodiment of triangular wave pulses configured to stimulate collagen production.

In embodiments to stimulate collagen production, the system as defined above is configured to provide wave pulses at a frequency between about 10 Hz and about 25 Hz and intensity of about 20 gauss. In some embodiments, the pulses are triangular, as shown. In other embodiments, wave pulses of any shape disclosed herein can be used.

In some embodiments, the system as defined above is configured to provide alternating current (AC) at a frequency of about 1 MHz.

In some embodiments, the system as defined above is configured to provide intensity of about 80 J/cm2 sec.

In some embodiments of the present invention, the duration of each pulse applied by the pulsed electromagnetic frequency generator is in a range between about 3 ms and about 1000 ms.

In some embodiments of the present invention, the frequency F of the pulses of the pulsed electromagnetic frequency generator is in a range between about 1 Hz and about MHz.

In some embodiments of the present invention, the power P applied by the pulses of the pulsed electromagnetic frequency generator is in a range between about 1 W and about 150 W of RMS average power.

In some embodiments of the present invention, the tissue diathermy device (4) is selected in a non-limiting manner from a group consisting of electric diathermy or any device emitting RF radiation absorbed by tissue.

In some embodiments of the present invention, the tissue diathermy device (4) is selected in a non-limiting manner from a group consisting of RF tissue diathermy, an optical device, an electromagnetic induction device, preferably an RF electromagnetic device, a device emitting sound waves such as, but not limited to, an ultrasonic diathermy device, a device configured to apply direct heat, or from any other means of controllably heating tissue to a temperature T.

In some embodiments of the present invention, the optical device is configured to emit light at wavelengths absorbed by tissue, thereby heating the tissue.

In some embodiments of the present invention, a sound wave emitting device is configured to emit sound waves absorbed by the tissue, thereby heating the tissue.

In some embodiments of the present invention, the temperature T to which the tissue is heated is in a range from about 30 degrees C. to about 80 degrees C.

In some embodiments of the present invention, the power supply and control system (6) includes a mechanism for cooling the skin.

In some embodiments of the present invention, the pulsed electromagnetic frequency generator (2) and the tissue diathermy device (4) have more than one applicator to treat more than one body part simultaneously.

In some embodiments of the present invention, the pulsed electromagnetic frequency generator (2) has electrostatic shielding.

Is should be emphasized that the system as defined in any of the embodiments produces synergistic outcomes in the in each of the following time scales: In the short-term (less than about a week), in the intermediate term (about two to three weeks) and in the long term (about a month or longer).

In the short term, contraction and thickening of collagen fibers occurs, which in turn results in an overall tightened and rejuvenated appearance of the skin, or a tightened and rejuvenated feel to mucosal tissues.

In the intermediate term, new epidermal cells and new collagen fibers are produced.

In the long term, cellulite is dispersed.

In yet other embodiments of the invention disclosed herein, at least one of the electrodes additionally comprises a hypodermic syringe for penetrating into subcutaneous tissue. By means of such a syringe, a substance with appropriate activity may be injected into the tissue during treatment. Non-limiting examples of such substances include a dye to absorb light in embodiments that use optical means for effecting tissue diathermy, a muscle relaxant, a local anesthetic, etc.

It is also within the scope of the invention to disclose a method for providing cosmetic improvement to the skin, comprising (a) generating N independent signals, where N is either the number of electrodes or the number of pairs of electrodes, of predetermined waveforms, frequencies, amplitudes, and relative phases to control at least one of pulsed electromagnetic frequency generation or tissue diathermy; (b) transmitting each of the N independent signals to at least one electrode; (c) placing at least one of the electrodes at least adjacent to the tissue to be treated; and (d) transmitting power carried by the signals to the tissue. In preferred embodiments, the N independent signals are phase-shifted relative to one another. The method can performed by using a device according to any of the embodiments described herein, or in any variant of a device described herein.

It is also within the scope of the invention wherein the step of generating N independent signals further comprises generating N independent pulsed electromagnetic fields such that the time-dependent amplitude At,m of the mth of the N independent signals is given by the relationship $A_{t,m} = A_{0,m} \cdot F_m(\omega_m t + \varphi_m)$ where A0,m is a predetermined constant which greater than or equal to 1, Fm is a predetermined periodic function of time, ωm is the angular frequency of the mth signal, and φm is a predetermined phase shift of the mth signal. While in preferred embodiments of the method, the step of generating N independent signals comprises a step in which $A_{0,m}$, $F_m$, and $\omega_m$ are substantially the same for all N signals, and $\varphi_m$ is substantially the same for any two pairs of signals m and m+1, this restriction is by no means required, and it is within the scope of the invention to disclose a method in which any or all of them are not identical for all N signals or for any two pairs of signals m and m+1. In preferred embodiments of the method in which $\varphi_m$ is substantially the same for all pairs of signals m and m+1, the method further includes a step of providing a phase shift $\varphi_m$ for each of the N independent signals according to the relationship $\varphi_m = \pi k(j-1)/N$, where $0 \leq k \leq 1$, m =1, 2, 3 ... N and j=1, 2, 3 ... N, where N is the number of electrodes. For example, for one electrode in a set of four (N=4), k=1 and the phase is 135 degrees, while, for another electrode in the set of four, the phase will be 45 degrees, and so on.

In some embodiments of the method, it further includes a step of choosing $F_m$ from the group consisting of sine, cosine, tan, cotangent (cot), sawtooth wave, triangular wave, square wave, rectangular wave, trapezoidal wave, spiked wave, and any combination thereof.

Reference is now made to FIG. 5A-D, which presents graphical representations of non-limiting examples of RF signals that may be applied to a set of four electrodes. In these graphs, the normalized amplitude of the signal is given as a function of ωt. In each graph, the curve corresponding to the signal transmitted to a particular pair of electrodes is labeled with the same letter as the corresponding pair of electrodes.

Figure 5A:
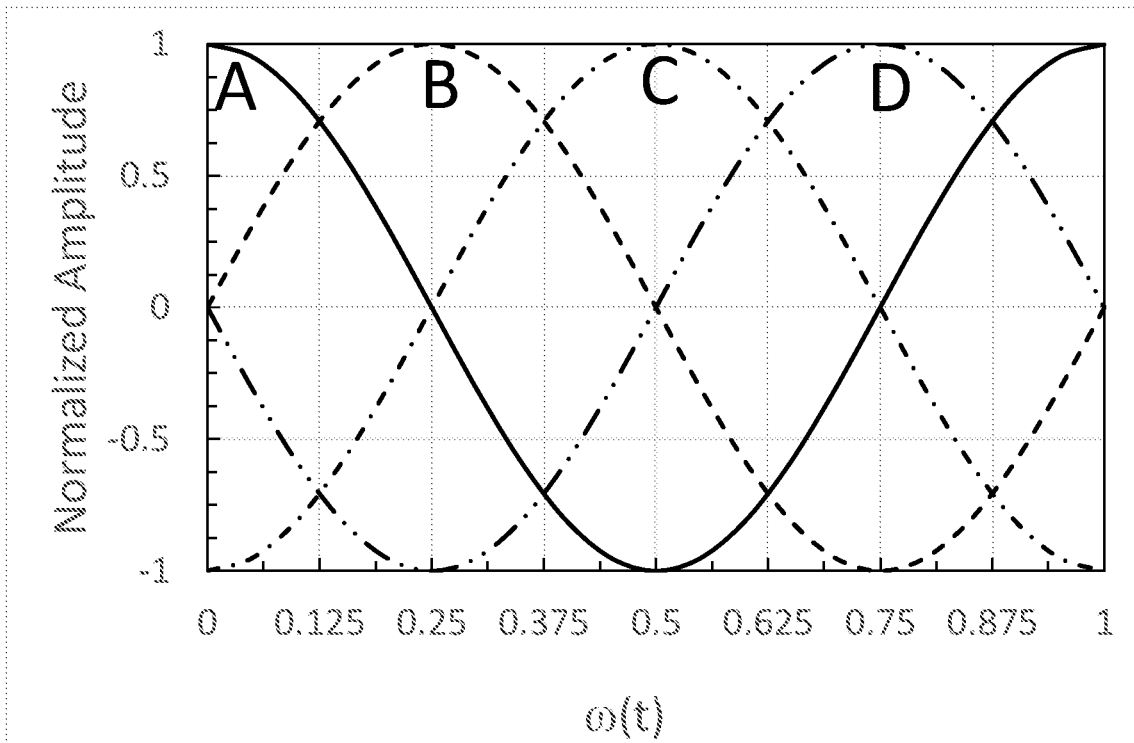
FIG. 5A-D schematically illustrates electromagnetic pulses with a phase shift between different electrodes.

FIG. 5A presents an embodiment in which N is 4, $F_m$ is a sine function, $\varphi_m = \pi k(j-1)/N$ where k=1 and N=4; and $A_{0,m}$ is 1.

Figure 5B:
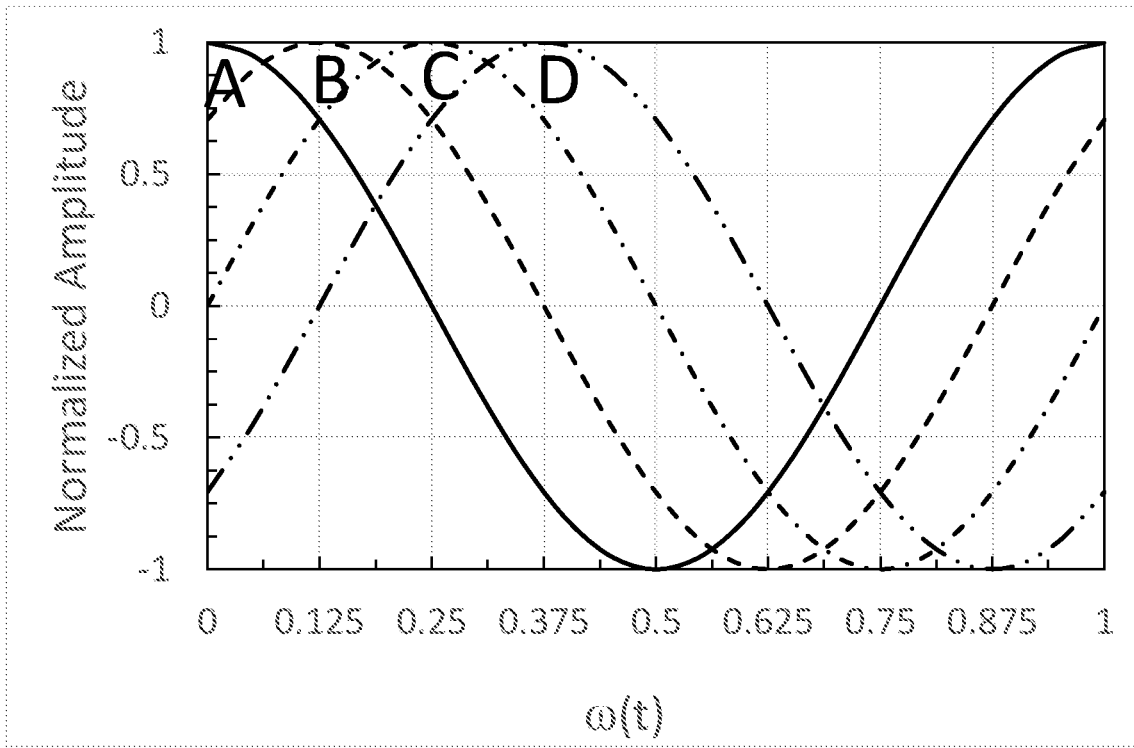

FIG. 5B presents an embodiment in which N is 4, $F_m$ is a sine function, $\varphi_m = \pi k(j-1)/N$ where k=1 and N=4, and $A_{0,m}$ is 1.

Figure 5C:
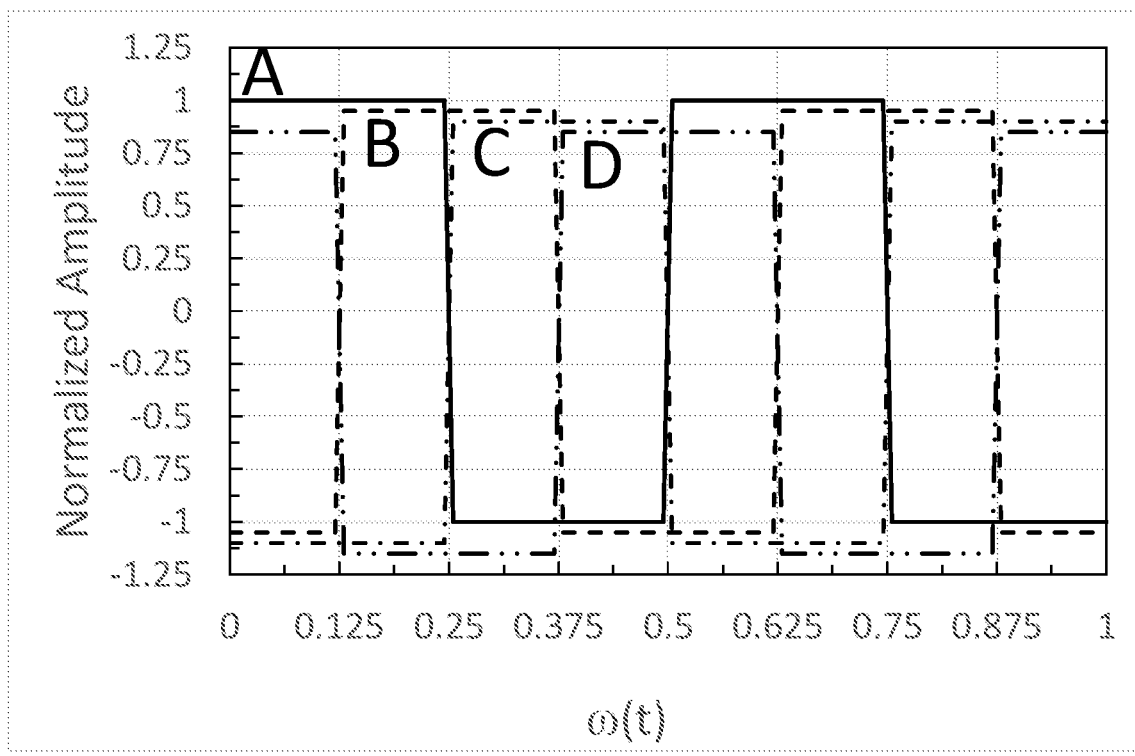

FIG. 5C presents an embodiment in which N is 4, $F_m$ is a square wave function, $\varphi_m$ is $\varphi_m = \pi k(j-1)/N$ where k=1 and N=4; in this case, for clarity of presentation, two cycles are shown (i.e. the x-axis is actually 2ωt), and the amplitudes of curves B, C, and D have been offset from 1. Thus, $A_{0,m}$ for A is 1; $A_{0,m}$ for B is 0.95, $A_{0,m}$ for C is 0.9; and, $A_{0,m}$ for D is 0.85.

Figure 5D:
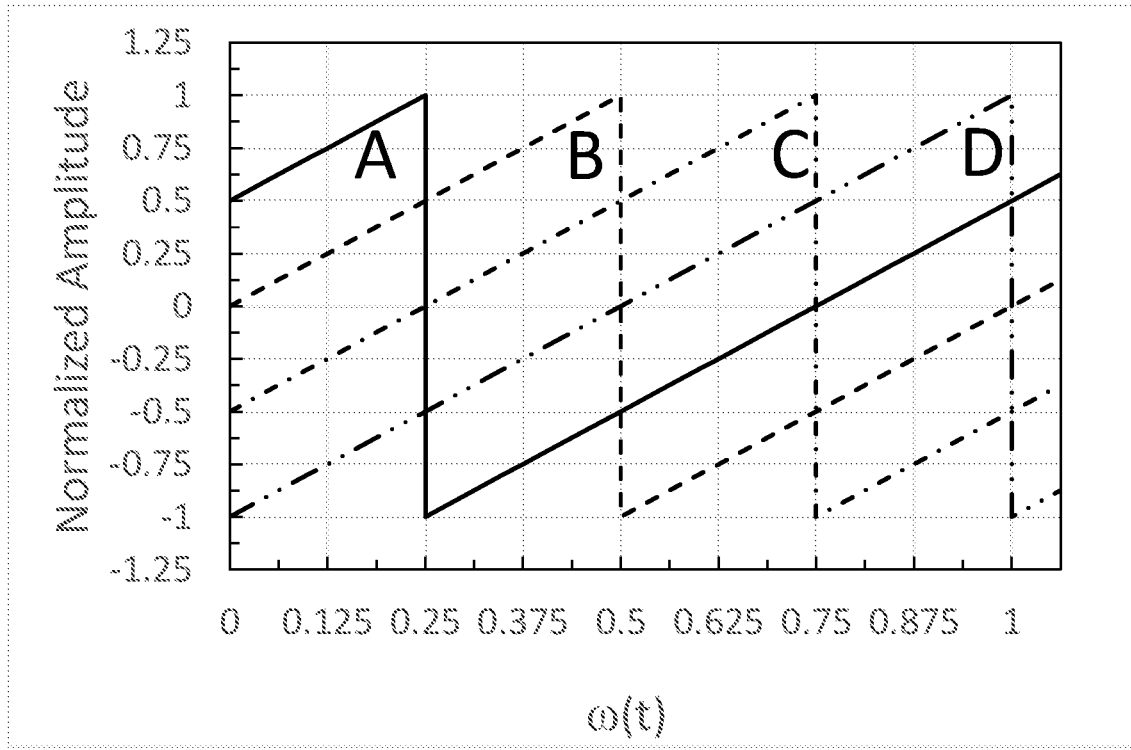

FIG. 5D presents an embodiment in which the waveform is a sawtooth function and $\varphi_m = \pi k(j-1)/N$ where k=1 and N=4, and $A_{0,m}$ is 1.

In yet other embodiments of the invention disclosed herein, at least one of the electrodes additionally comprises a hypodermic syringe for penetrating into subcutaneous tissue. By means of such a syringe, a substance with appropriate activity may be injected into the tissue during treatment. Non-limiting examples of such substances include a dye to absorb light in embodiments that use optical means for effecting tissue diathermy, a muscle relaxant, a local anesthetic, etc.

It is also within the scope of the invention to disclose a method for providing cosmetic improvement to the skin, comprising (a) generating N independent signals, where N is either the number of electrodes or the number of pairs of electrodes, of predetermined waveforms, frequencies, amplitudes, and relative phases to control at least one of pulsed electromagnetic frequency generation or tissue diathermy; (b) transmitting each of the N independent signals to at least one electrode; (c) placing at least one of the electrodes at least adjacent to the tissue to be treated; and (d) transmitting power carried by the signals to the tissue. In preferred embodiments, the N independent signals are phase-shifted relative to one another. The method can performed by using a device according to any of the embodiments described herein, or in any variant of a device described herein.

It is also within the scope of the invention wherein the step of generating N independent signals further comprises generating N independent pulsed electromagnetic fields such that the time-dependent amplitude $A_{t,m}$ of the mth of the N independent signals is given by the relationship $A_{t,m}=A_{0,m} \cdot F_m(\omega_m t+\varphi_m)$, where $A_{0,m}$ is a predetermined constant which greater than or equal to 1, $F_m$ is a predetermined periodic function of time, $\omega_m$ is the angular frequency of the mth signal, and $\omega_m$ is a predetermined phase shift of the mth signal. While in preferred embodiments of the method, the step of generating N independent signals comprises a step in which $A_{0,m}$, $F_m$, and $\omega_m$ are substantially the same for all N signals, and $\varphi_m$ is substantially the same for any two pairs of signals m and m+1, this restriction is by no means required, and it is within the scope of the invention to disclose a method in which any or all of them are not identical for all N signals. In preferred embodiments of the method in which $\varphi_m$ is substantially the same for all pairs of signals m and m+1, the method further includes a step of providing a phase shift $\varphi_m$ for each of the N independent signals according to the relationship $\varphi_m=\pi k(j-1)/N$, where $0 \leq k \leq 1$, m=1, 2, 3 . . . N and j=1, 2, 3 . . . N, where N is the number of electrodes. For example, for one electrode in a set of four (N=4), k=1 and the phase is 135 degrees, while, for another electrode in the set of four, the phase will be 45 degrees, and so on.

In preferred embodiments of the method, it further includes a step of choosing $F_m$ from the group consisting of sine, cosine, tan, cotangent (cot), sawtooth wave, triangular wave, square wave, rectangular wave, trapezoidal wave, spiked wave, and any combination thereof.

Figure 6:
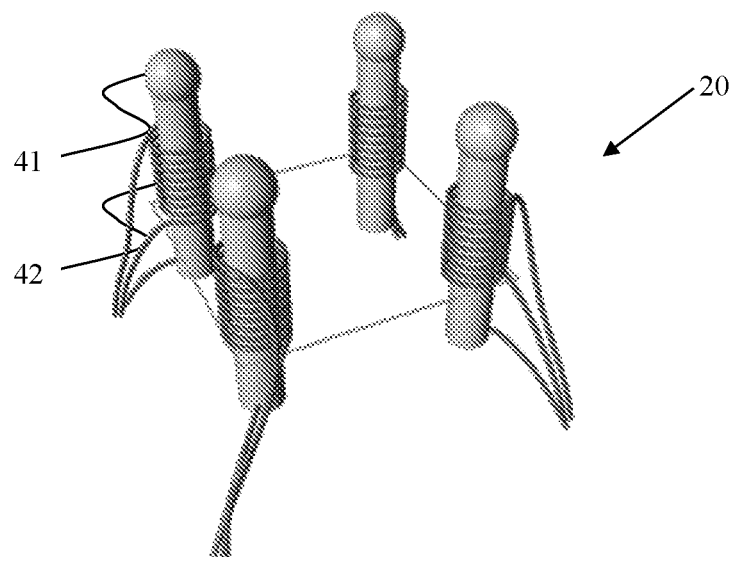
FIGS. 6-7 illustrate an embodiment of a mucosa viability improving system.
Figure 7:
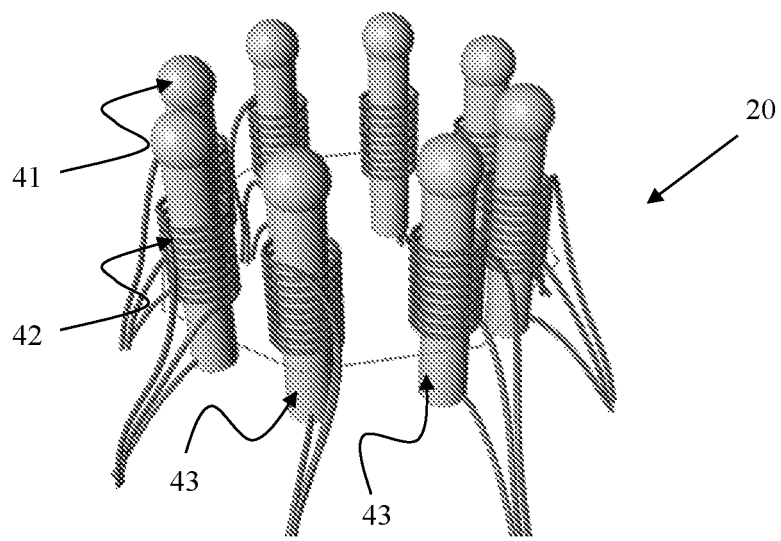

Reference is now made to FIGS. 6-7 illustrating a preferred embodiments of an integrated system (20) of the present invention, configured to increase skin or mucosal rejuvenation of a region of a patient's skin.

The system (20) comprises at least two electrodes (41) configured to be placed on a region of a patient's skin, mucosa and any combination thereof; each of the electrodes comprises a coil (42), and a contactor (43), with the contactor (43) configured to contact the patient's skin, mucosa and any combination thereof and the coil (42) at least partially looped around at least a portion of the contactor (43).

It should be emphasized that each of the electrodes is configured for both (i) providing electromagnetic pulses to a region of a patient's skin, mucosa and any combination thereof (via the coil); and, (ii) applying heat up to temperature T to the region of the patient's skin, mucosa and any combination thereof.

Furthermore, it should be emphasized that all of the electrodes simultaneously provide electromagnetic pulses to the region of the patient's skin, mucosa and any combination thereof as well as applying heat to the region of a patient's skin, mucosa and any combination thereof, thereby heating the region of the patient's skin, mucosa and any combination thereof to a temperature T.

The heat is provided to the skin, mucosa and any combination thereof by applying an electrical current through the electrodes which is absorbed by the tissue.

FIG. 6 illustrates a variant of the embodiment of the system (20) comprising 4 electrodes (41) and FIG. 7 illustrates a variant of the embodiment of the system (20) comprising 8 electrodes (41). These embodiments are configured for treating skin. Other variants can be used for treating internal mucosa, such as the vagina.

It should be emphasized that the application of the system (20) increases tissue rejuvenation such that the rejuvenation increase (SRI) due to the present treatment is greater than the sum of the SRI provided by increasing the electromagnetic pulse and the SRI provided by increasing the tissue diathermy.

According to some variants of these embodiments of the present invention, the electromagnetic pulses have a frequency between about 10 Hz and about 25 Hz and an intensity of about 20 gauss.

According to some variants of these embodiments of the present invention, the electromagnetic pulse is at a frequency of about 15 Hz, with a pulse width of about 5 ms and an intensity of about 12 gauss.

According to some variants of these embodiments of the present invention, the system reduces side effects and/or harmful effects of the electromagnetic pulses and/or tissue diathermy such that the reduction of the side effects and/or harmful effects is greater than the sum of the reduction due to the reduction in electromagnetic pulses and the reduction due to the reduction in tissue diathermy.

According to some variants of these embodiments of the present invention, the system (20) additionally comprises a control system (6) configured to regulate at least one of the electromagnetic pulses and the tissue diathermy.

In some variants of these embodiments of the present invention, the system is configured to provide a dynamic magnetic field such that the intensity of the electromagnetic pulses varies with time.

In some variants of these embodiments of the present invention, the shape of the electromagnetic pulse is selected in a non-limiting manner from a group consisting of: a square wave, a sine wave, a triangular wave, a sawtooth wave, a ramp wave, a spiked wave and any combination thereof.

In some variants of these embodiments of the present invention, the duration of each pulse is in a range between about 3 ms and about 1000 ms.

In some variants of these embodiments of the present invention, the frequency F of the pulses is in a range between about 1 Hz and about 1 MHz.

In some variants of these embodiments of the present invention, the power P applied by the system is in a range between about 1 W and about 150 W of RMS average power.

In some variants of these embodiments of the present invention, the temperature T of the heated tissue is in a range from about 30 degrees C. to about 80 degrees C. In some variants of these embodiments of the present invention, the control system (6) monitors the physical tissue parameters and changes the applied heat and the electromagnetic pulses so as to maintain the treatment within safe treatment parameters.

In some variants of these embodiments of the present invention, the power supply and control system (6) additionally comprises:

a. at least one processor configured to store in a communicable database predetermined parameters defining (i) safe treatment parameters and (ii) unsafe treatment parameters; the parameters selected from a group consisting of: total duration of a treatment $t_t$, time $t_p$ during which PEMF is applied, temperature T of the treated tissue, duty cycle $t_p/t_r$, frequency F, power P applied by the pulses from a pulsed electromagnetic frequency generator, intensity I of said ultrasound irradiation, depth D of said treated tissue, magnetic field intensity B, tissue impedance, specific absorption rate (SAR), superficial muscle contractions and any combination thereof b. at least one sensor configured to sense electromagnetic radiation and heat radiation parameters selected from a group consisting of: total duration of a treatment $t_t$, time $t_p$ during which PEMF is applied, temperature T of the treated tissue, duty cycle $t_p/t_r$, frequency F, power P applied by the pulses from a pulsed electromagnetic frequency generator, intensity I of said ultrasound irradiation, depth D of said treated tissue, magnetic field intensity B, tissue impedance, specific absorption rate (SAR), superficial muscle contractions and any combination thereof;

c. at least one regulating mechanism configured to allow electromagnetic radiation and heating if the parameters are within safe treatment parameters and to stop the electromagnetic radiation and the heating if the parameters are within unsafe treatment parameters.

In some embodiments of the present invention, the system (6) includes a mechanism for cooling the skin.

In some embodiments of the present invention, the system (20) is especially configured to increase rejuvenation of treated skin, mucosa and any combination thereof in the immediate (short) term (less than about a week).

In some embodiments of the present invention, the system (20) is especially configured to increase rejuvenation of treated skin, mucosa and any combination thereof in the intermediate term (about 2 weeks to about 3 weeks).

In some embodiments of the present invention, the system (20) is especially configured to increase rejuvenation of treated skin, mucosa and any combination thereof in the long term (more than about a month).

Figure 8:
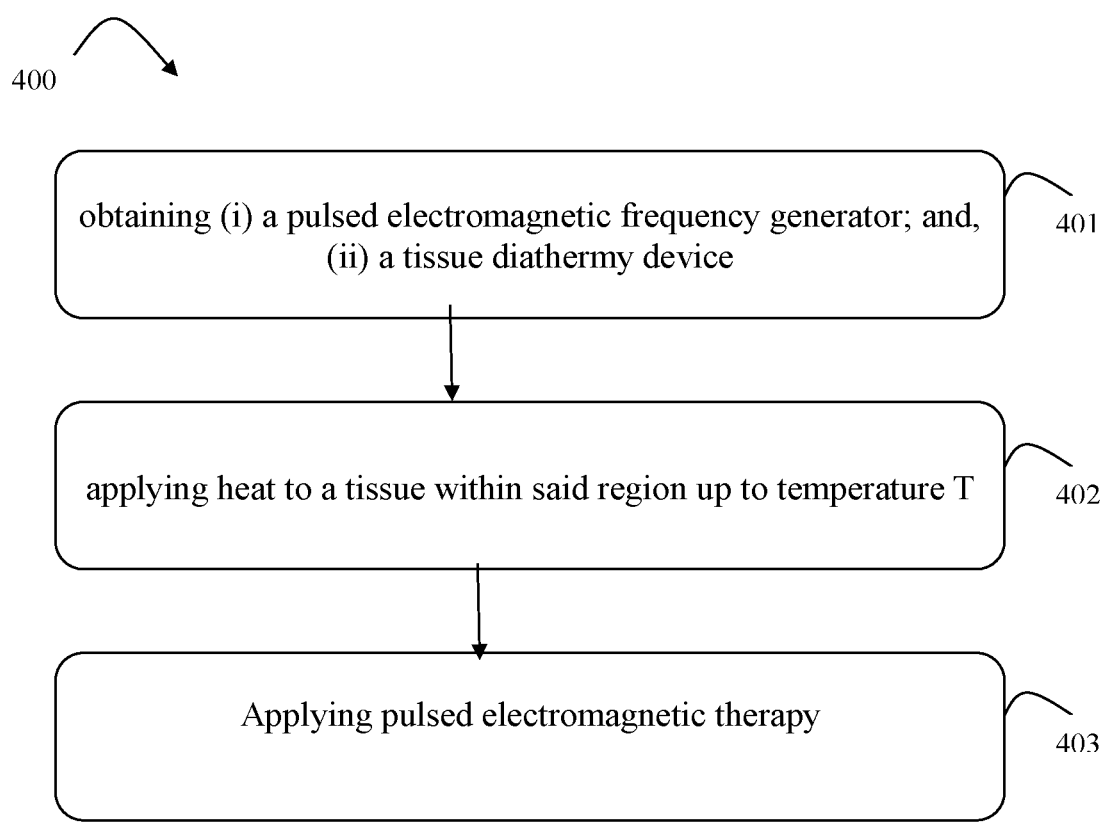
FIGS. 8-13 schematically present methods of improving mucosal viability.

Reference is now made to FIG. 8, schematically illustrating an embodiment of a method (400) of increasing rejuvenation of a region of a patient's skin, mucosa and any combination thereof. The method comprises steps selected inter alia from obtaining (i) a pulsed electromagnetic frequency generator; and, (ii) a tissue diathermy device (401); applying heat to tissue within the region, heating the region up to a temperature T (402); the temperature T being optimized for producing new collagen and causing dermal proliferation, and contracting existing collagen. While the collagen contraction tightens the tissue and, for treated skin, conceals wrinkles immediately, the dermal proliferation and new collagen production have a later effect. The next step is applying additional pulsed electromagnetic fields (403) which generate a healing mechanism in the heated tissue which includes growth factor production and cytokine release and eventually angiogenesis.

Figure 9:
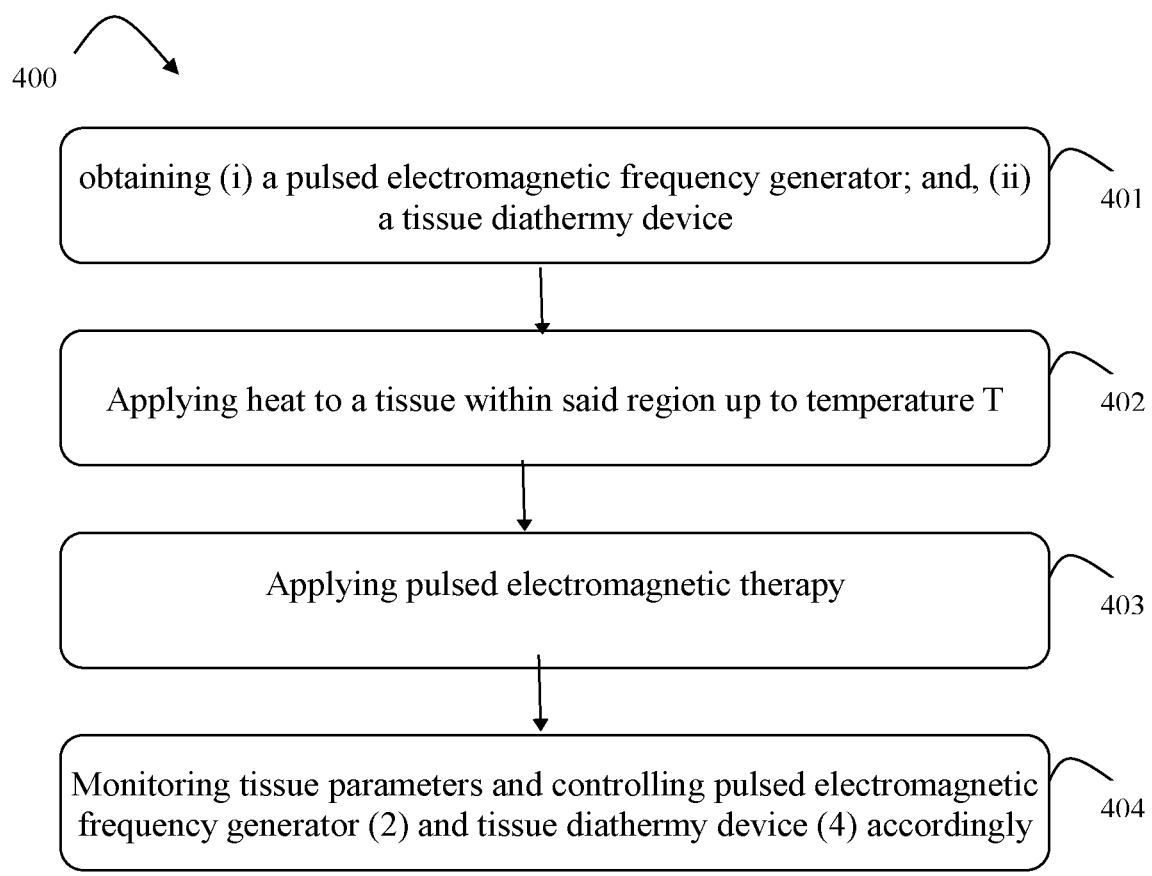

Reference is now made to FIG. 9, which illustrates an embodiment of a preferred method of the present invention. According to this embodiment, the method (400) additionally comprises a step of: monitoring and/or controlling the steps of applying heat to tissue within the region and of applying pulsed electromagnetic therapy to the region (404).

Figure 10:
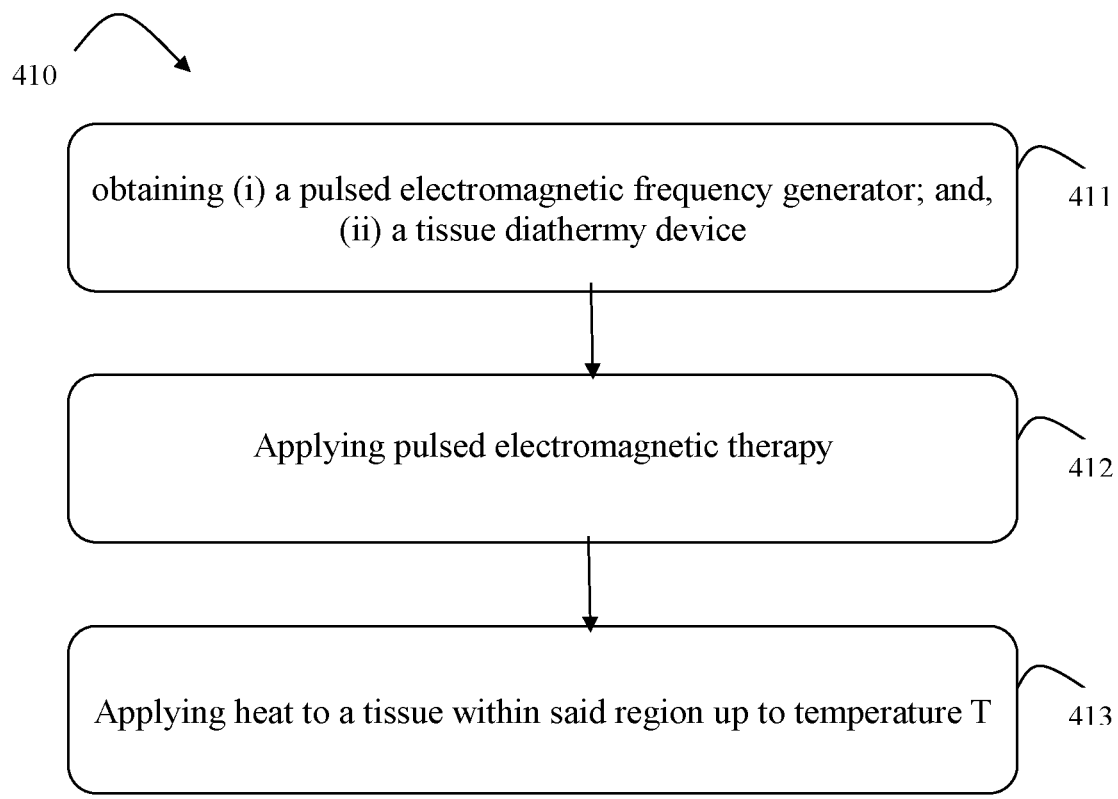

Reference is now made to FIG. 10, schematically illustrating an embodiment of a method (410) of increasing rejuvenation in a region of a patient's skin, mucosa and any combination thereof. The method comprises steps selected inter alia from obtaining (i) a pulsed electromagnetic frequency generator; and (ii) a tissue diathermy device (411). The next step is applying an additional pulsed electromagnetic field (412) which generates a healing mechanism in the heated tissue, which includes release of growth factors and cytokines and eventually angiogenesis. The final step is applying heat to the tissue within the region, thereby heating the tissue to temperature T (413); the temperature T is optimized for producing new collagen and causing dermal proliferation and contracting collagen. While the collagen contraction tightens the tissue and, for skin, conceals wrinkles immediately, the dermal proliferation and new collagen production have a later effect.

Figure 11:
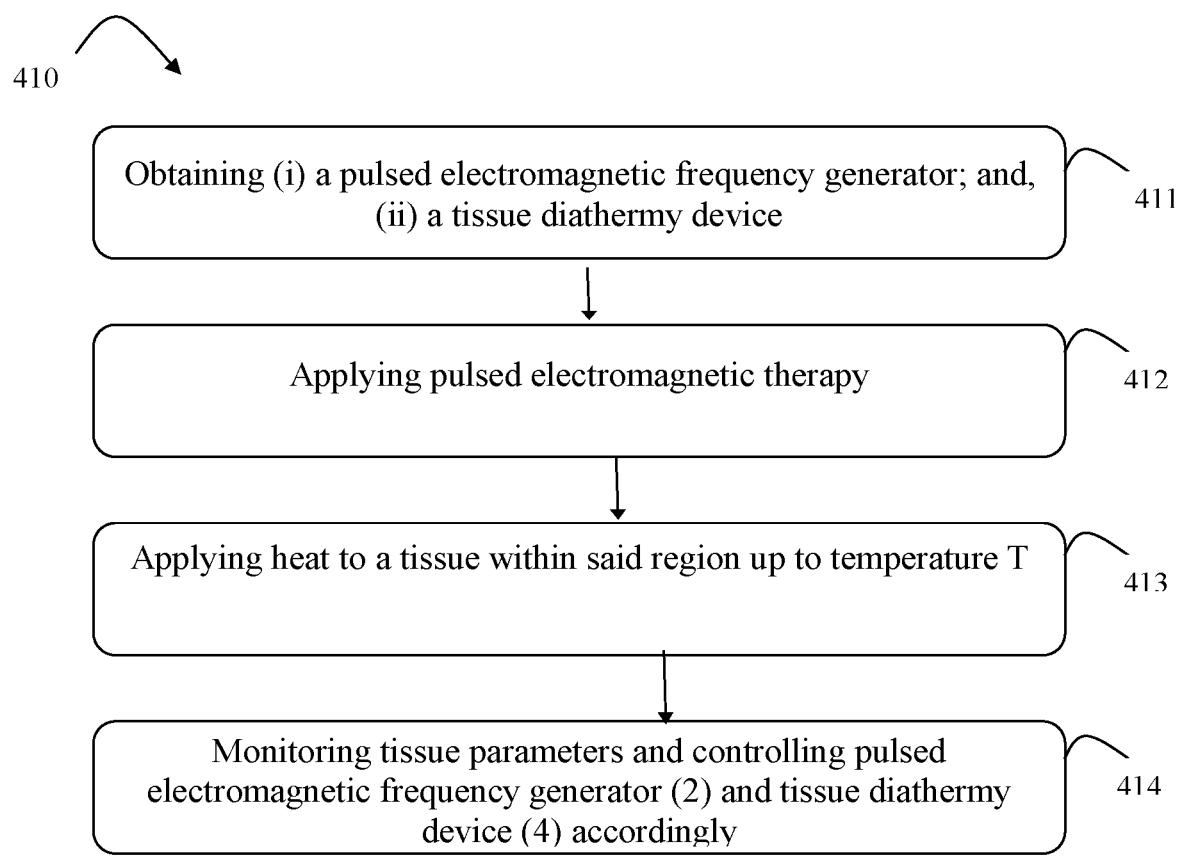

Reference is now made to FIG. 11, which illustrates another embodiment of a method of the present invention. According to this embodiment, the method (410) additionally comprises a step of: monitoring and/or controlling the steps of applying heat to tissue within the region and/or a step of applying pulsed electromagnetic therapy to the region (414).

Figure 12:
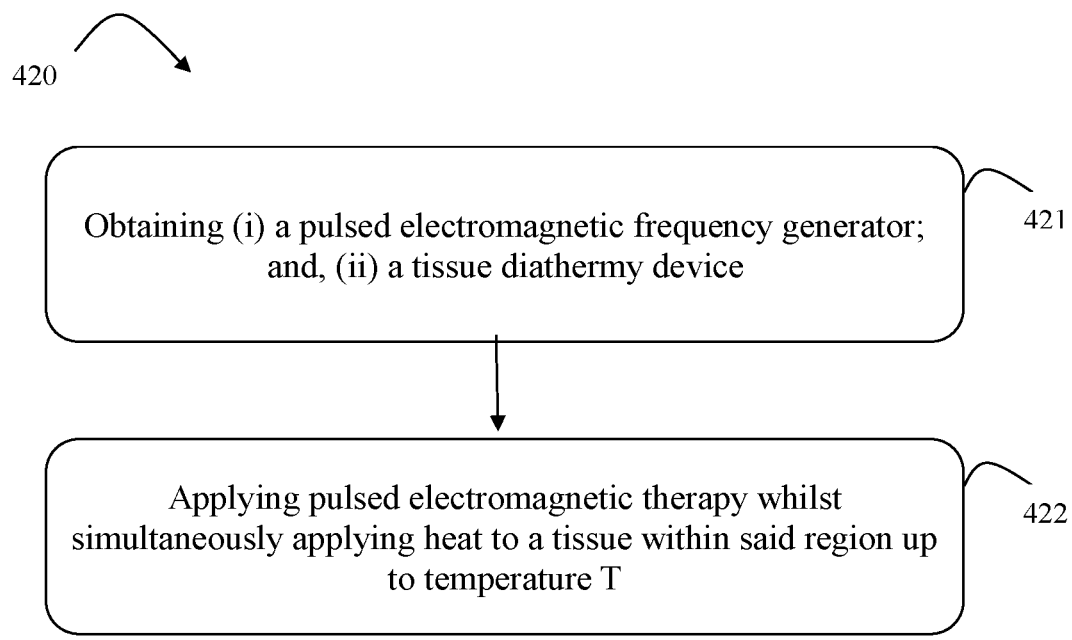

Reference is now made to FIG. 12, schematically illustrating an embodiment of a method (420) of increasing skin rejuvenation of a region of a patient's skin, mucosa and any combination thereof. The method comprises steps selected inter alia from: obtaining (i) a pulsed electromagnetic frequency generator; and, (ii) a tissue diathermy device (421). The next step is applying an additional pulsed electromagnetic field (422) whilst simultaneously applying heat to tissue within the region, heating the tissue to a temperature T. The electromagnetic pulses generate a healing mechanism in the heated tissue, which includes growth factor and cytokine release and eventually angiogenesis. The temperature T is optimized for producing new collagen and causing dermal proliferation and contracting collagen. While the collagen contraction tightens the tissue and, for skin, conceals wrinkles immediately, the dermal proliferation and new collagen production have a later effect.

Figure 13:
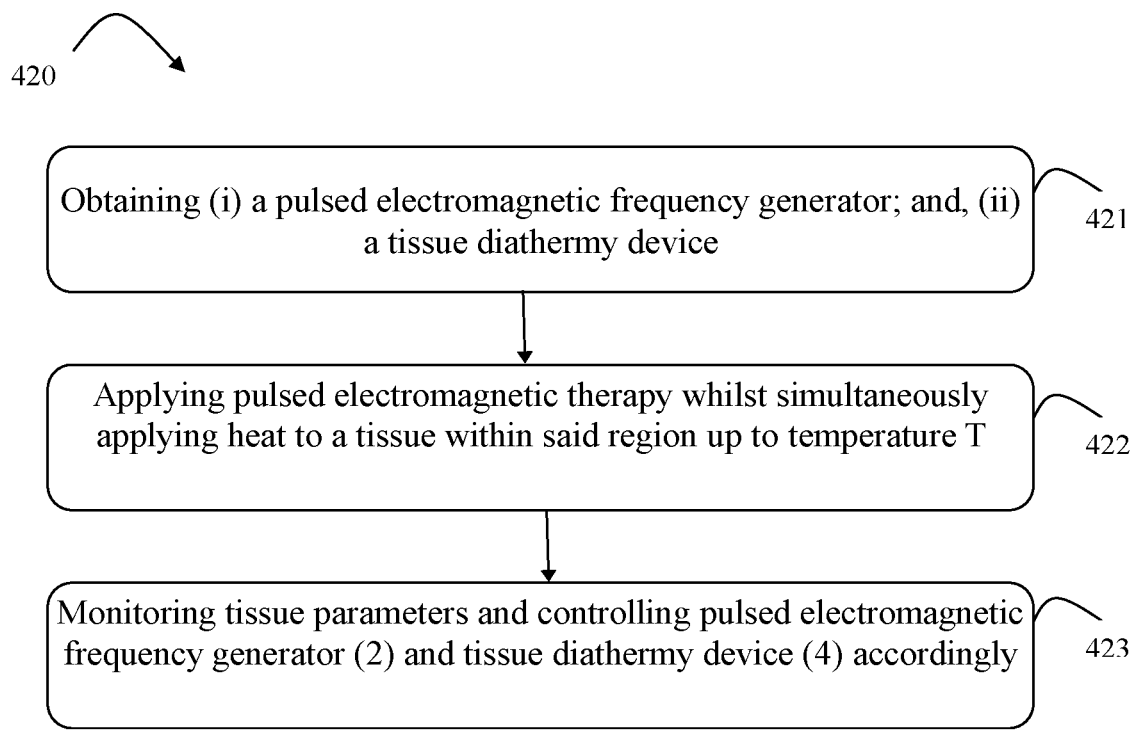

Reference is now made to FIG. 13, which illustrates method preferred embodiment of the present invention. According to this embodiment, the method (420) additionally comprises a step of: monitoring and/or controlling the steps of applying heat to tissue within the region and/or the step of applying pulsed electromagnetic therapy to the region (424).

In some embodiments of the present invention, each of the methods as defined above additionally comprises a step of selecting the temperature T to be in a range of about 30 degrees C. to about 80 degrees C.

In some embodiments of the present invention, each of the methods as defined above additionally comprises a step of applying a dynamic electromagnetic field in said region, where the peak intensity of the electromagnetic field varies with time.

In some embodiments of the present invention, each of the methods as defined above additionally comprises steps of:

a. storing in a communicable database predetermined parameters defining (i) safe treatment parameters and (ii) unsafe treatment parameters; the parameters are selected from a group consisting of: total duration of a treatment $t_t$, time $t_p$ during which PEMF is applied, temperature T of the treated tissue, duty cycle $t_p/t_r$, frequency F, power P applied by the pulses from a pulsed electromagnetic frequency generator, intensity I of said ultrasound diathermy, depth D of said treated tissue, magnetic field intensity B, tissue impedance, specific absorption rate (SAR), superficial muscle contractions and any combination thereof;
b. sensing electromagnetic radiation and heating parameters selected from a group consisting of: total duration of a treatment $t_t$, time $t_p$ during which PEMF is applied, temperature T of the treated tissue, duty cycle $t_p/t_t$, frequency F of the applied radiation, power P applied by the pulses from a pulsed electromagnetic frequency generator, intensity I of the heating, depth D of treated tissue, magnetic field intensity B, tissue impedance, specific absorption rate (SAR), superficial muscle contractions and any combination thereof;
c. allowing the electromagnetic radiation and the heating if the parameters are within said safe treatment parameters and stopping the electromagnetic radiation and the heating if the parameters are in the unsafe treatment parameters.

In preferred embodiments of the present invention, the step of applying heat is performed by RF electromagnetic fields. Devices which can be used to induce heating in the tissue can be selected from a group consisting of: RF tissue diathermy, an ultrasonic diathermy device, an optical device, an electromagnetic induction device, preferably an RF electromagnetic induction device, a device emitting sound waves, a device configured to apply direct heat, or from any other means of heating tissue to a temperature T.

In some embodiments of the present invention, each of the methods as defined above additionally comprises a step of selecting the frequency F of the pulses applied during the step of applying pulsed electromagnetic therapy to the region to be in a range from about 1 Hz to about 1 MHz.

In some embodiments of the present invention, each of the methods as defined above additionally comprises a step of selecting the power P applied during the step of applying pulsed electromagnetic therapy to the region to be in a range from about 1 W per pulse to about 150 W of RMS average power.

In some embodiments of the present invention, in each of the methods as defined above the step of applying heat lasts in a range from about 0.01 minutes to about 100 minutes.

In some embodiments of the present invention, in each of the methods as defined above, a pulsed electromagnetic field is applied for a time in a range from about 0.01 minutes to about 100 minutes.

In some embodiments of the present invention, in each of the methods as defined above, the steps of applying heat and applying the pulsed electromagnetic therapy are carried out in a manner selected from a group consisting of: simultaneously, sequentially (alternating applying heat and applying pulsed electromagnetic therapy) or separately (applying heat in one phase of a treatment and pulsed electromagnetic therapy in a separate phase of the treatment).

In some embodiments of the present invention, in each of the methods as defined above, the method is repeated 1 to 100 times in each treatment.

In some embodiments of the present invention, a typical protocol for the pulsed electromagnetic frequency generator (4) includes, for non-limiting example, a preset number of about 1 μs pulses with a duty cycle of about 50% and a pause of up to about 250 μs. In protocols of this type, power is supplied to the tissue during the period in which the preset number of pulses is applied.

In some embodiments of the present invention, a typical protocol for the pulsed electromagnetic frequency generator (4) includes, for non-limiting example, about 10 pulses of about 1 μs period with about 50% duty cycle and a preset pause of up to about 512 μs. In protocols of this type, power is supplied to the tissue during the period in which the preset number of pulses is applied.

In some embodiments of the present invention, a typical protocol for the pulsed electromagnetic frequency generator (4) includes, for non-limiting example, a variant of the previous protocol, wherein the number of pulses administered is a multiple of about 10.

In some embodiments of the present invention, in each of the methods as defined above, the treatment is repeated more than once.

In some embodiments of the present invention, each of the methods as defined above additionally comprises a step of selecting the shape of the electromagnetic pulse from a group consisting of: a square wave, a sine wave, a triangular wave, a sawtooth wave, a ramp wave, a spiked wave and any combination thereof.

In some embodiments of the system, the tissue to be treated is mucosal tissue, such as vaginal tissue. In such embodiments, the device is inserted into the vagina. The device of the present invention can be used for vaginal rejuvenation with the same processes that occur in facial rejuvenation, as disclosed above, namely production of new collagen, shortening of existing collagen fibers, production of growth factors, and dermal proliferation, with a typical outcome being thicker and more elastic vaginal tissue.

Unlike devices used to treat external skin, in which the device is moved during treatment so that different regions of the skin are treated at different times, in preferred embodiments of a device for treatment of vaginal tissues, the vaginal treatment device is configured so that it remains stationary within the vagina during treatment.

Figure 14:
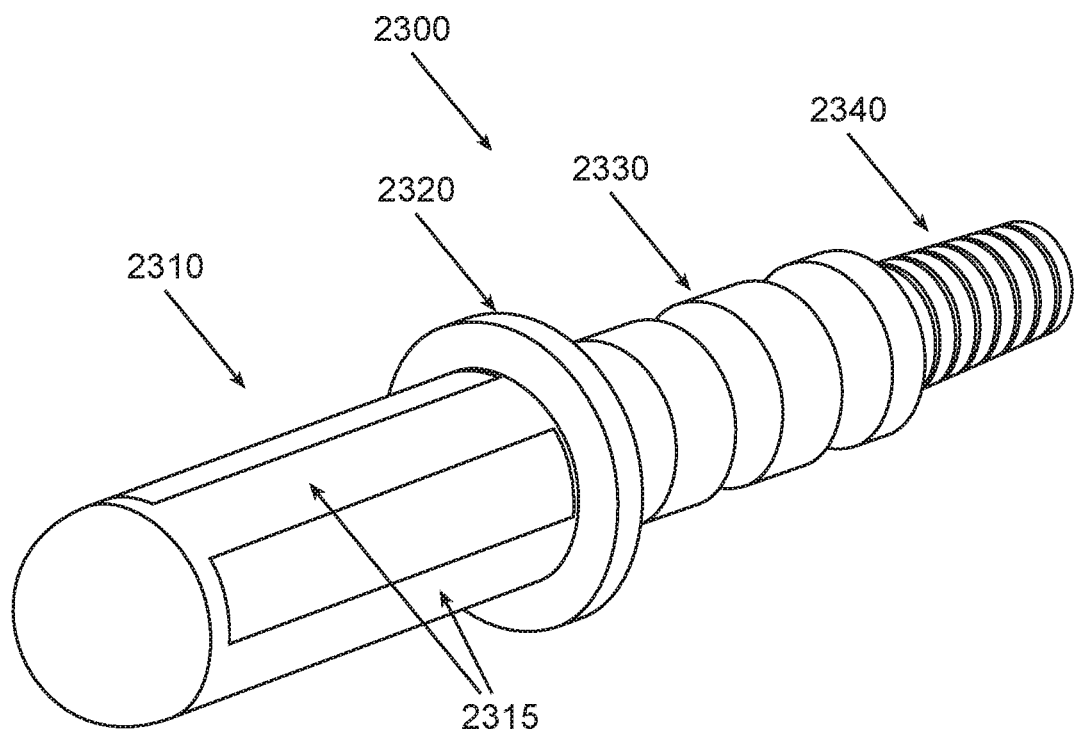
FIGS. 14 and 15 schematically illustrate embodiments of a device for treating the vagina.
Figure 15:
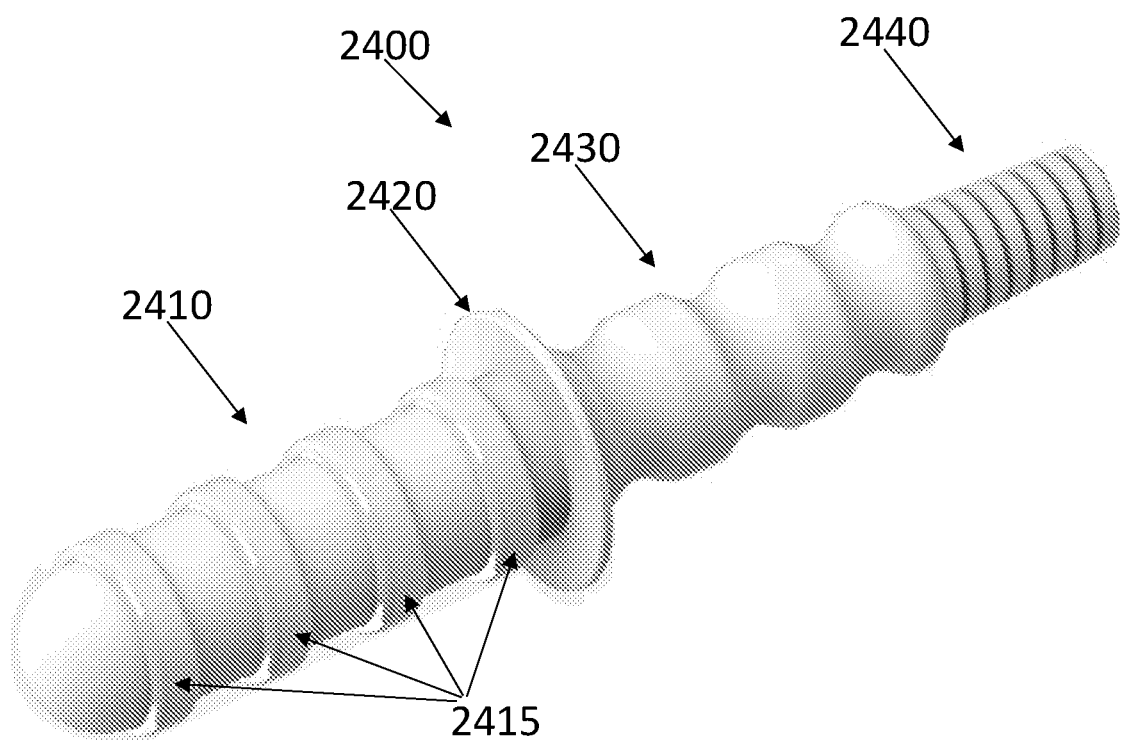
Figure 16:
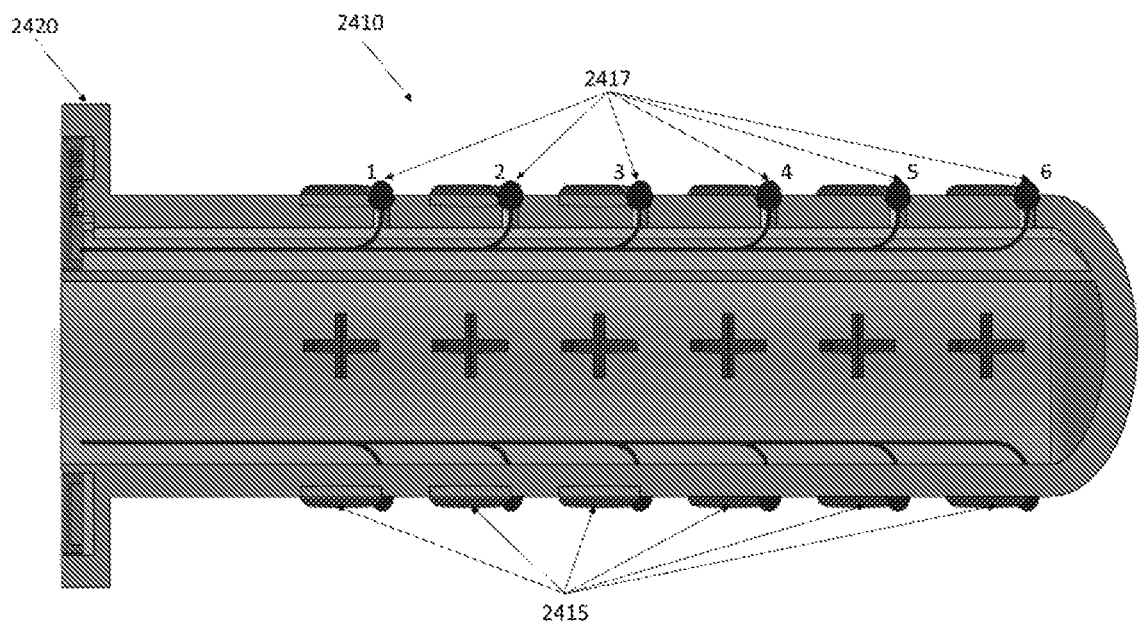
FIG. 16 schematically illustrates a cross-section of an embodiment of a device for treating the vagina.

Embodiments of a device configured to treat vaginal tissues are shown in FIGS. 14-16.

In reference to FIG. 14, an embodiment of a disposable portion (2300) of a device for vaginal use is shown. The disposable portion is the portion for insertion into the vagina; the reusable portion, which comprises a handle mechanism for holding the device during insertion and removal (and possibly during use), the control mechanism for controlling delivery of power to the disposable portion, and, in some embodiments, a mechanism for delivering heating or cooling fluids, is not shown.

It should be noted that, in some embodiments, the disposable portion (2300) is sterilizable and can be reused.

The device (2300) comprises a distal section (2310) for insertion into the vagina, a ring (2320) to limit the depth of penetration, a medial portion (2330), and a proximal portion (2340) configured to provide connection between the disposable portion (2300) and the re-usable portion. The connection provided by the proximal portion (2340) includes a mechanical connection and electrical communication; it can also include a fluid connection.

The embodiment of FIG. 14 has longitudinal electrodes (2315).

The embodiment of FIG. 14 has four longitudinal electrodes (2315); the number of longitudinal electrodes can be between 1 and about 20, preferably between about 4 and about 10.

In preferred variants, the device comprises sensors to monitor the temperature. This can be the temperature of at least a portion of an electrode, the temperature of the tissue adjacent to a portion of an electrode, and any combination thereof.

In preferred variants of these embodiments, the temperature of the tissue is measured.

In embodiments with at least one temperature sensor, preferably, a sensor will be adjacent to an electrode or inside an electrode so that a temperature measured by a temperature sensor can be associated with the at least a portion of an electrode primarily responsible for inducing the temperature. In preferred variants of embodiments with temperature sensors, there is at least one temperature sensor adjacent to each electrode and the temperature is individually and separately controlled for at least a portion of each electrode. The temperatures of any selected portions of a given pair of electrodes can be the same or they can be different. In preferred variants, the temperatures will be different, with higher temperatures for the distal portions of the electrodes and lower temperatures for the proximal portions of the electrodes.

A difference between a device for treating external skin tissue and treating vaginal tissue is that the labial and vulval tissues are much more sensitive to heat than the vaginal tissues.

The temperature sensor is preferably selected from a group consisting of a thermocouple, a thermistor, and any combination thereof.

A difference between a device for treating external skin tissue and treating vaginal tissue is that the labial and vulval tissues are much more sensitive to heat than the vaginal tissues. Therefore, it is preferable that the proximal end of the distal section (2410) of the device be heated less than the remainder of the distal section (2410).

FIG. 15 shows an embodiment of a vaginal treatment device (2400) in which the electrodes (2415) are ring-like, encircling the distal section (2410) of the device. The device of FIG. 14 has a ring (2420) to prevent excessive penetration of the device into the vagina, a medial portion (2430) and a proximal portion (2440), with the proximal portion (2440) configured to provide connection between the disposable portion (2400) and the re-usable portion (not shown). The connection provided by the proximal portion (2440) includes a mechanical connection and electrical communication; it can also include a fluid connection.

The embodiment of FIG. 15 has four ring electrodes (2415); the number of ring electrodes can be between 1 and about 20, preferably between about 4 and about 10.

In embodiments with at least one temperature sensor, preferably, a sensor will be adjacent to an electrode or inside an electrode so that a temperature measured by a temperature sensor can be associated with the electrode primarily responsible for inducing the temperature. Preferably, the temperature sensors are configured to measure the tissue temperature, not the electrode temperature.

In preferred variants of embodiments with temperature sensors, there is at least one temperature sensor adjacent to each electrode and the temperature is individually and separately controlled for each electrode. The temperatures of any given pair of electrodes can be the same or they can be different. In preferred variants, the temperatures will be different, with higher temperatures for central electrodes and lower temperatures for edge electrodes.

The at least one temperature sensor can be selected from a group consisting of: a thermistor, a thermocouple and any combination thereof. FIG. 16 shows a cross-section of a device with 6 ring electrodes (2415) encircling the distal section of the device (2410); the ring (2420) to prevent excessive penetration of the device into the vagina is also shown, A temperature sensor (2417) is shown adjacent to each ring electrode (2415).

In preferred embodiments of the device, a predefined temperature profile can be created within the vagina. Typically, at least one predefined temperature profile can be stored in a database in communication with a processor, with the processor in communication with at least one temperature sensor and at least one power supply; the power supply providing power to the electrodes.

In some embodiments of the device, the available temperature profiles can be displayed on a conventional display, such as, but not limited to, a GUI, and the user can select a profile. Selection can be via any conventional means of inputting data such as, but not limited to, a touchscreen, a keyboard, voice recognition and any combination thereof. Once selected, the temperature profile will be maintained in the device for the duration of the treatment, or until the user selects a different temperature profile. In preferred embodiments, the user can select or change a temperature profile while the distal end of the device is within the vagina so that there is no need to remove the device from the vagina in order to select or change a temperature profile.

In preferred embodiments, both PEMF and heating are supplied to the electrodes. In preferred embodiments, RF is used to heat the tissue. A heating mechanism can be selected from a group consisting of RF tissue diathermy, electric current, an inductive electromagnetic field and any combination thereof.

The temperature can vary longitudinally along the distal section (2410) of the device, radially around the distal section (2410) of the device and any combination thereof. Typically, the temperature profile is created via feedback, with a comparison between the temperature measured by each sensor and a predefined, stored temperature profile being used to adjust the power applied to each electrode.

Figure 17:
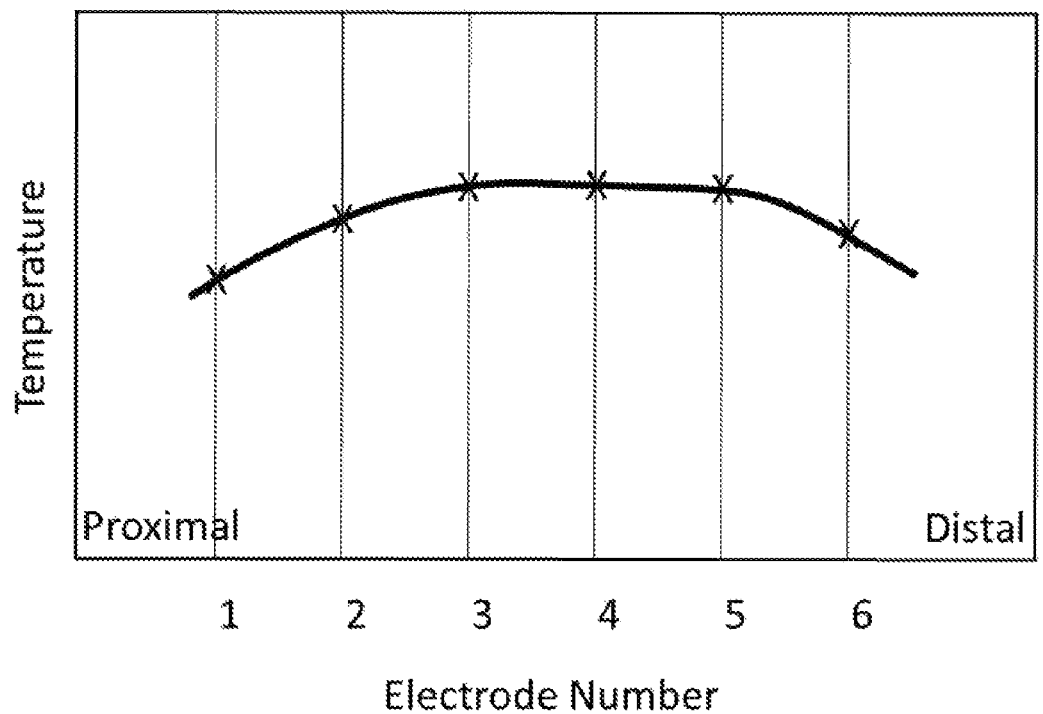
FIG. 17 schematically illustrates a temperature profile for an embodiment of a device for treating the vagina.

FIG. 17 shows an exemplary temperature profile, where the temperature varies longitudinally along the distal section (2410) of the device. The numbers 1 to 6 refer to the 6 electrodes shown in FIG. 16, with 1 being the most proximal electrodes and 6 the most distal electrode. The temperature is lowest at electrode 1, which is closest to the heat-sensitive vulva and labia. In this example, the temperature of the distal-most electrode, electrode 6, is also lower than that of the central electrodes, Under feedback control, more RF power will be supplied to electrodes 3, 4 and 5 and less RF power will be supplied to electrodes 1, 2 and 6 so as to maintain the desired temperature profile in the vagina.

In some embodiments, the temperature in the vagina will be between about 30 degrees C. and about 80 degrees C. during treatment, preferably between about 40 degrees C. and about 50 degrees C.

As can be seen from FIGS. 1B, 1D, 14, 15 and 16, the electrodes and sensors can be enclosed in a platform, to maintain them in a desired position. Similarly, the processor and regulating means can be enclosed in a platform. The processor/regulating mechanism platform can be the same as the electrode/sensor platform, reversibly connected to it, or permanently connected to it. Either platform can additionally comprise a power supply.

In some embodiments, the device can provide at least one of fractional PEMF and fractional tissue diathermy, with only a fraction of the electrodes activated at any one time. This can reduce discomfort to the patient during treatment.

Figure 18:
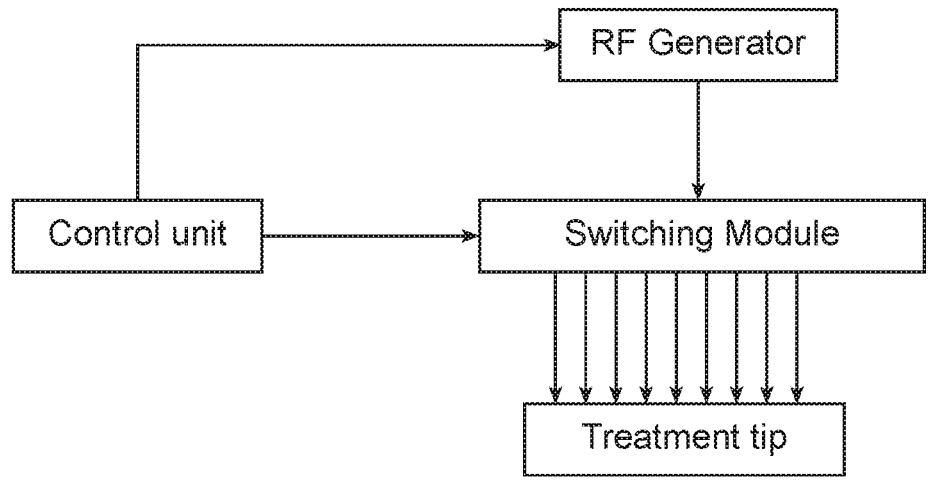
FIGS. 18-21 schematically illustrate embodiments of switching modules.

FIG. 18 shows the principal schematics of a device. The pulsed electromagnetic frequency generator (4) produces the electrical current, while a tissue diathermy device (6), preferably an RF device, provides a means of heating the tissue. The current and the means of heating are delivered to at least one switching module, so that at least one of the pulsed electromagnetic field and the heating means can be switched in a predefined sequence to different electrodes. The sequence of switching and duration of each switch can be controlled by a control unit, as disclosed above. The switching module and at least one of the pulsed electromagnetic frequency generator and the tissue diathermy device can be close to each other or be separated. For example, a generator can be in a console of the system and the switching module in the platform. The switching module can be hosted in the platform or in the console. In case of placing the switching module in the console, a cable with multiple wires will be used between the console and the platform.

Figure 19:
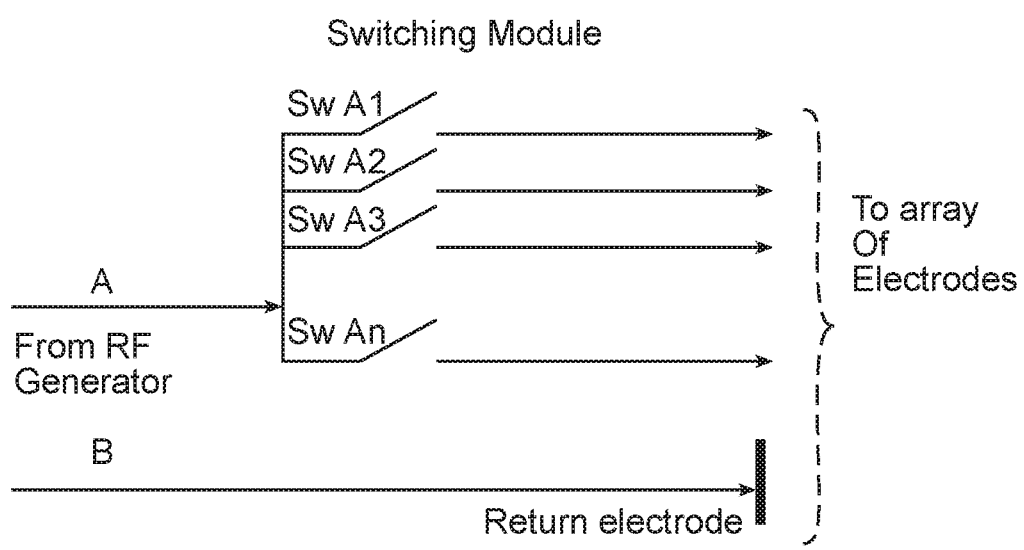

FIG. 19 shows one embodiment of a switching module with an RF generator for the heating means. The Line A from the RF generator is split in the switching module into N branches according to maximum number of electrodes in the treatment tip and each branch contains an On/Off switch. Some of the switches may be closed, with the rest open. The electrical current passes through a closed switch (or switches) into the treatment tip and returns back through the return electrode to line B of the generator. The Return electrode can be part of the treatment tip or can be a separate pad connected to a patient's body.

Figure 20:
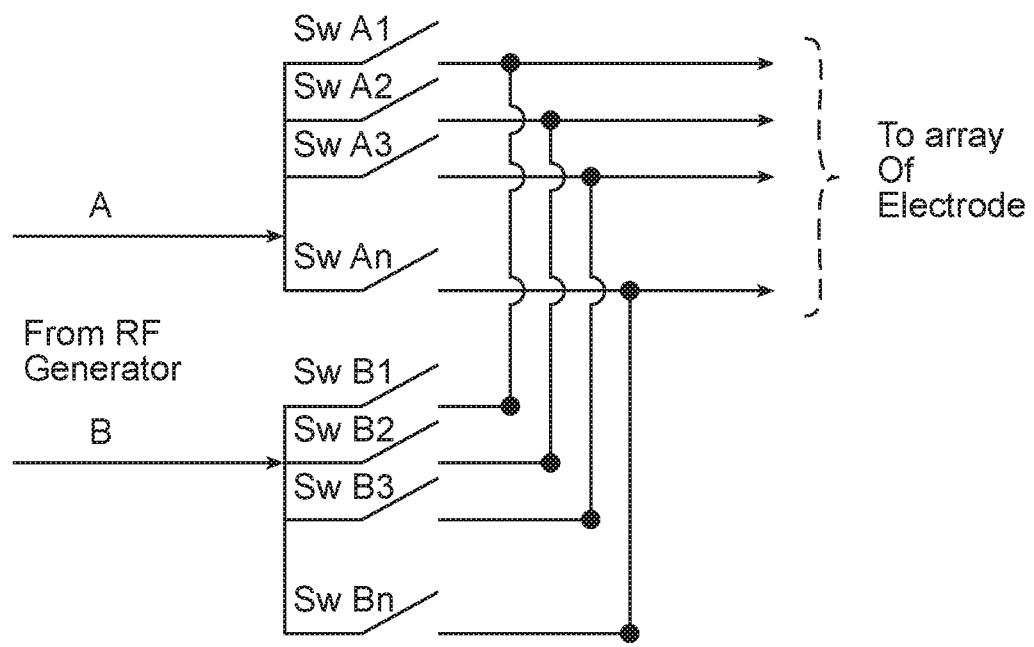

FIG. 20 shows another embodiment of a switching module. This schematic allows use of part of the electrodes (minority) as active and rest of the electrodes (majority) as a return path. The lines A and B come from the RF generator. Each wire splits to N parallel branches according to maximum number of electrodes in the treatment tip. Each branch includes an On/Off switch configured to connect between one of the inputs (A or B) to the output at the tip. Some of the switches in Line A can be closed, with the rest open. In line B, the opposite is true. Switches that were open in line A should be closed in Line B and vice versa. The electrical current will pass through the closed switches in Line A to the treatment tip and return back through the closed switches in line B. This configuration allows work without return electrodes but requires twice as many switches as the previous configuration.

Figure 21:
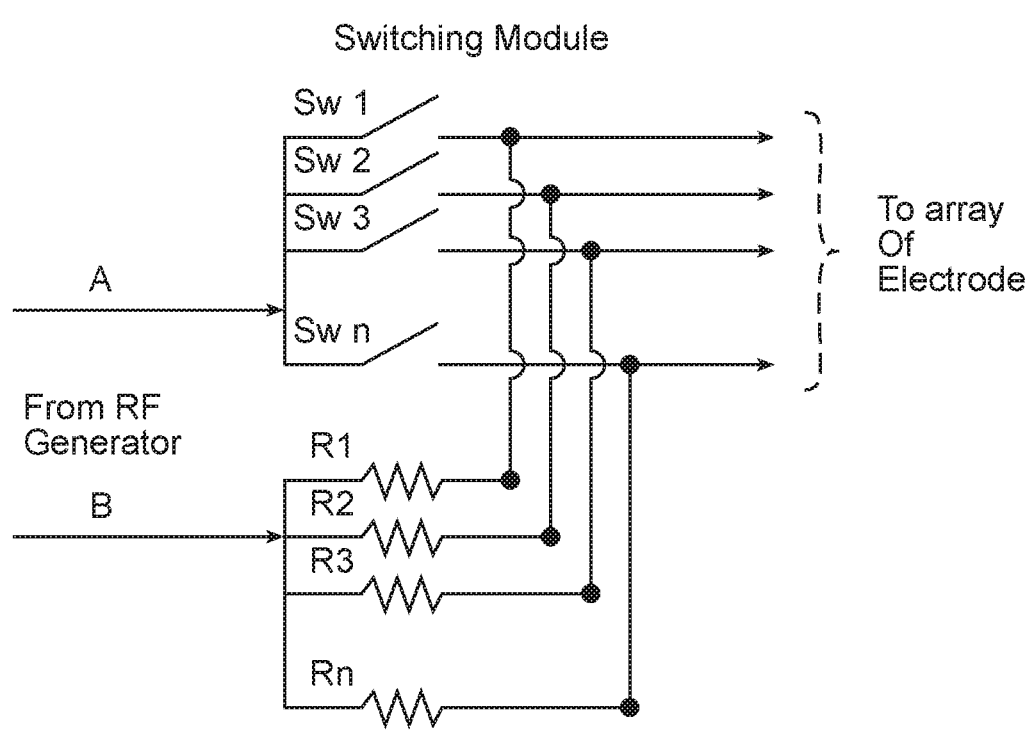

FIG. 21 shows yet another embodiment of a switching module. In this configuration, resistors instead of switches connect the electrodes to line B. The resistors should have a much higher impedance than the typical impedance of the skin under a single electrode. If in Line A one switch is closed, the electrical current will pass through this switch to tissue. The alternative path through the resistor will take only small portion of the current since the resistance of the resistor much higher than that of the tissue. The return path is through the rest of the electrodes. All the resistors in these electrodes are connected in parallel and therefore overall resistance will be low and the power losses in the resistors will be low. The additional advantage of such configuration is that resistors can function as current limiters, which helps to prevent a sensation of pain in the patient and homogenously distributes current between the electrodes.

In some embodiments, the device can additionally comprise a mechanism to induce suction, so as to induce at least a portion of the tissue to come into intimate contact with the device. In some embodiments, the device will comprise at least one port. When the device is in use, suction is applied to at least one of the ports, causing the tissue to be drawn into intimate contact with the device and, if a port opens into a recess in the device, causing the tissue to be drawn into the recess in the device. In preferred embodiments, the skin is drawn in to a sufficient extent that it makes physical contact with the ports and any electrodes or transducers disposed thereabout.

The suction unit is configured to operate either continuously or in pulses, delivering either a constant suction, or a pulsed suction to the tissue.

FIG. 22 provides schematic cross-sectional views of five exemplary embodiments of the device that provide non-limiting illustrations of possible geometries of the device. While these illustrations only show the elements that are disposed in the plane of the cross-section and a hidden view of a limited number of elements hidden by skin 500 that has been drawn into the housing, it is emphasized that the only limitations on the number of tissue diathermy devices and pulsed electromagnetic frequency generators that can be used are the physical size of the housing and the minimum distance necessary to permit wrapping with the coil and to prevent short-circuiting. In the embodiments shown, the tissue diathermy devices and pulsed electromagnetic frequency generators are shown as separate; in some embodiments, the same electrodes produce both tissue diathermy device and pulsed electromagnetic fields.

Figures 22A, 22B:
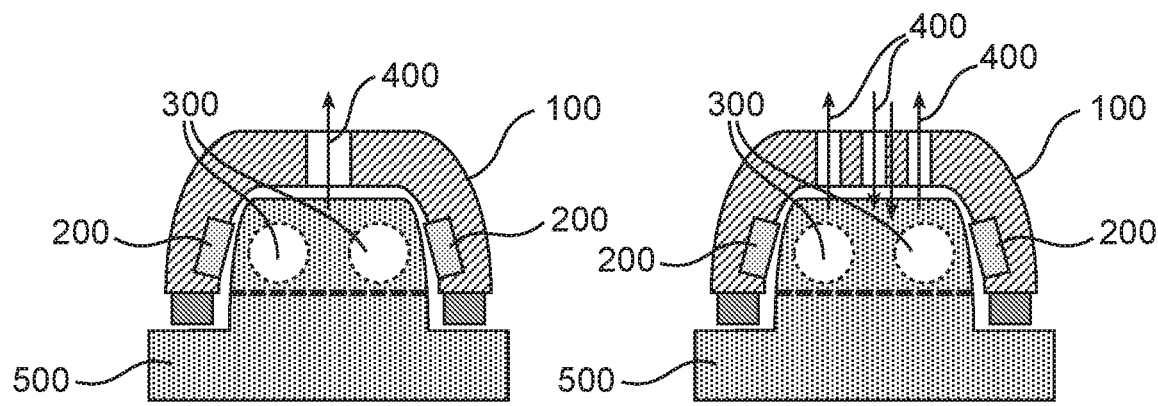
FIGS. 22A-22F schematically illustrate embodiments of ports configured to allow suction to draw tissue into contact with the device.

FIG. 22A shows an embodiment in which there is a single port 400; the arrow indicates the direction of air flow when the device is in fluid connection with a source of vacuum. Tissue diathermy devices 200 are disposed on the lip and interior surface of the housing, while pulsed electromagnetic frequency generators 300 are disposed on the interior surface of the housing. FIG. 22B illustrates an embodiment in which the tissue diathermy devices and transducers are disposed as shown in FIG. 22A, but in which a plurality of ports 400 are provided. The arrows indicate the direction of air flow when the device is in fluid connection with a source of vacuum and when the air is let back in after the treatment has concluded.

Figures 22C, 22D:
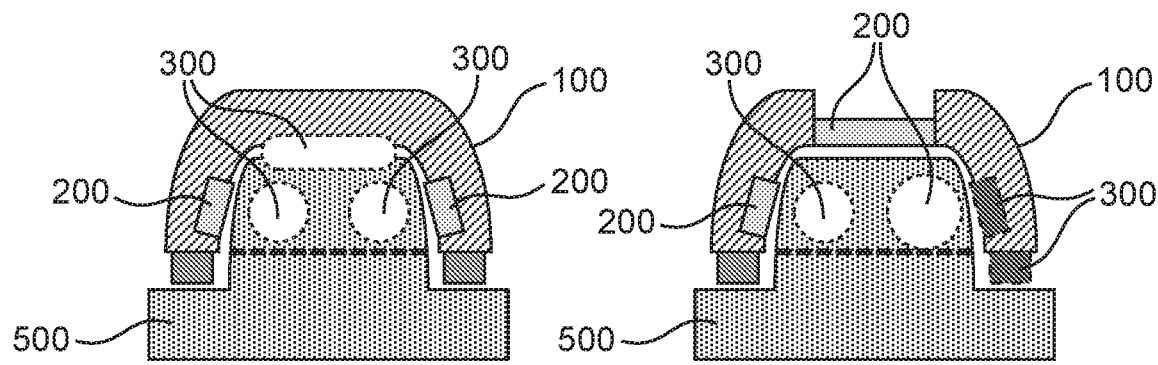

FIG. 22C shows an embodiment in which at least one transducer is disposed about the substantially closed end of the housing. FIG. 22D shows an embodiment in which both pulsed electromagnetic frequency generators and tissue diathermy devices are disposed about the lip of the housing and both pulsed electromagnetic frequency generators and tissue diathermy devices are disposed about its inner surface. In this embodiment, at least one tissue diathermy device is disposed about the substantially closed end of the housing. In the embodiments illustrated in FIGS. 22C and 22D, the ports displaced from the central axis of the housing, and hence are not shown in the figures.

Figure 22E:
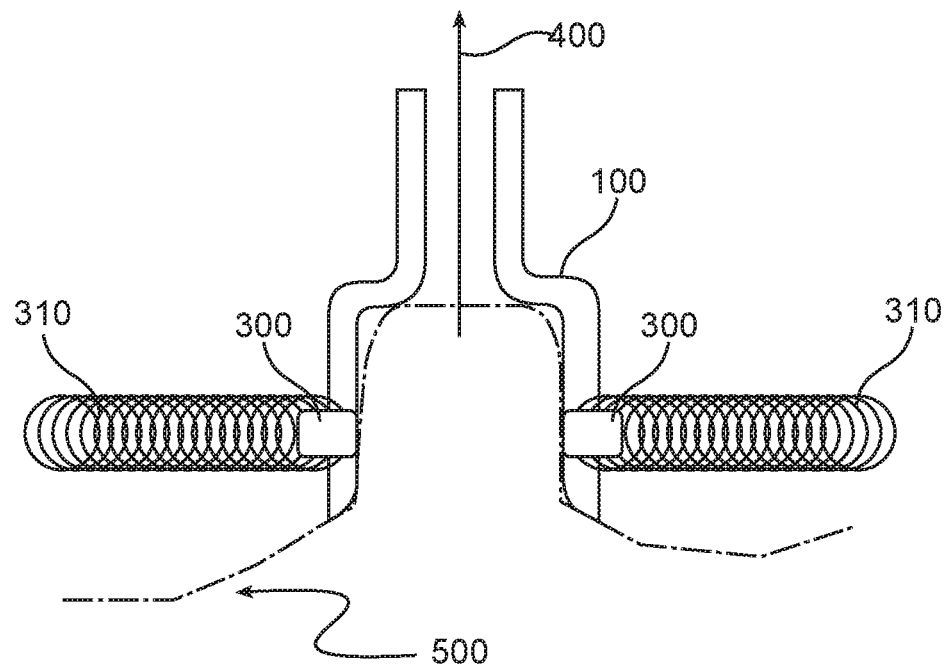

FIG. 22E presents schematic illustration of an additional embodiment of the invention. In this embodiment, the housing has a generally cylindrical rather than cup-shaped housing, and the pulsed electromagnetic frequency generators are disposed about the interior surfaces of the sides of the housing, as shown in the figure.

Figure 22F:
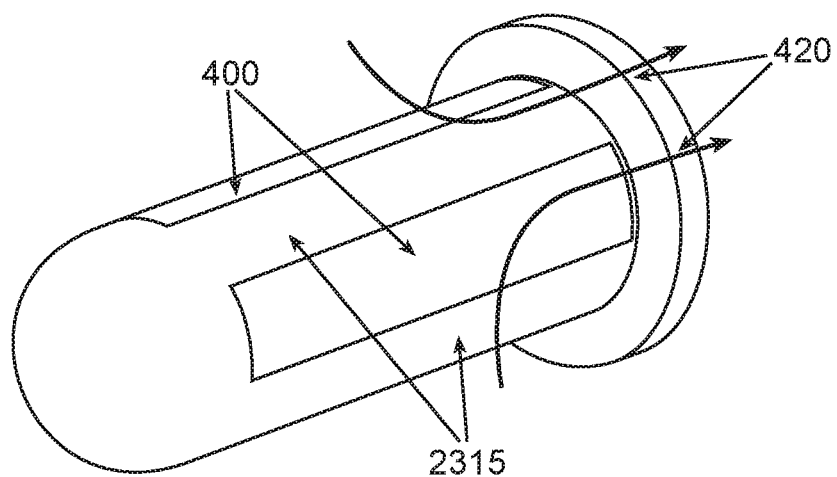

FIG. 22F presents a schematic illustration of the distal end of an embodiment of the invention with a cylindrical housing, with longitudinal electrodes (2315) on the exterior of the housing and ports (400) between the electrodes (2315). Airflow to cause suction is schematically illustrated by the arrows (420).

Figure 23:
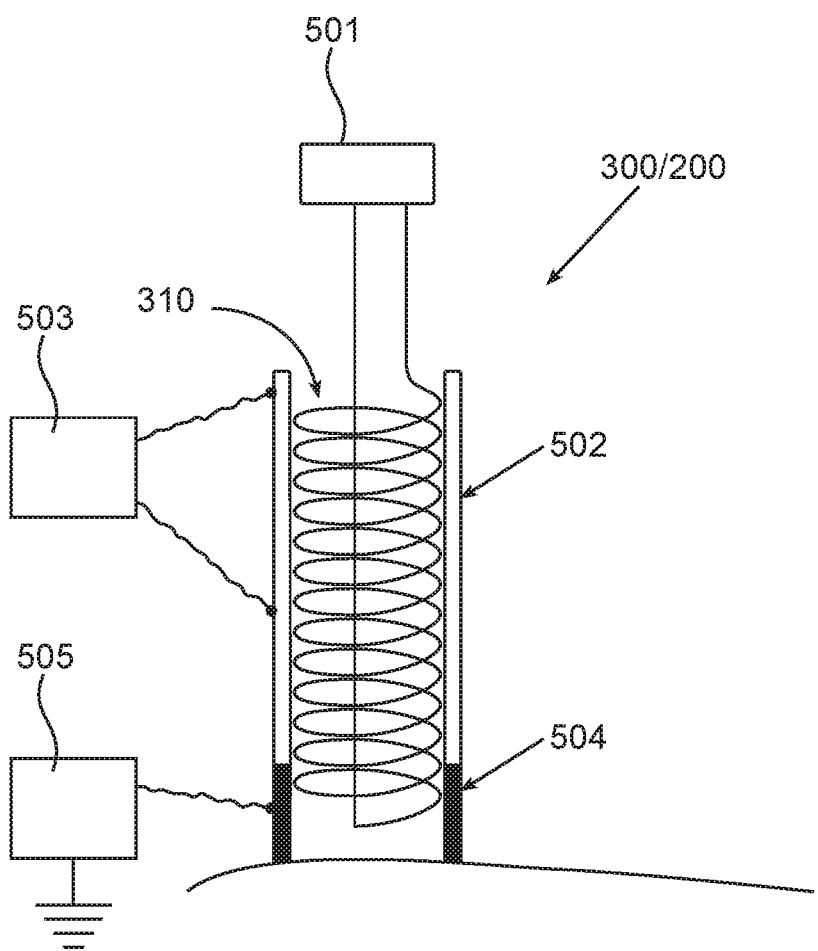
FIG. 23 schematically illustrates an embodiment of an electrode with an internal coil.
Figures 24A, 24C, 24E:
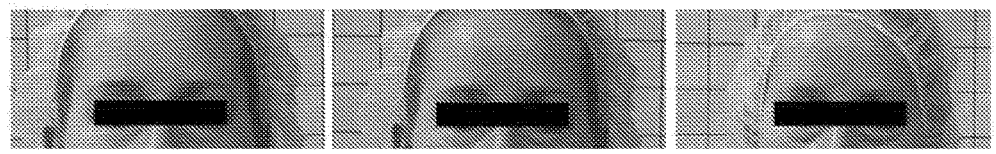
FIGS. 24A-F illustrate effects of treatment on a patient treated on both sides with a device of the present invention.
Figures 24B, 24D, 24F:
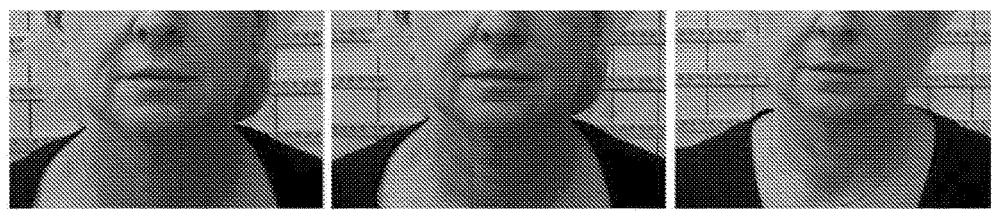
Figures 25A, 25C, 25E:
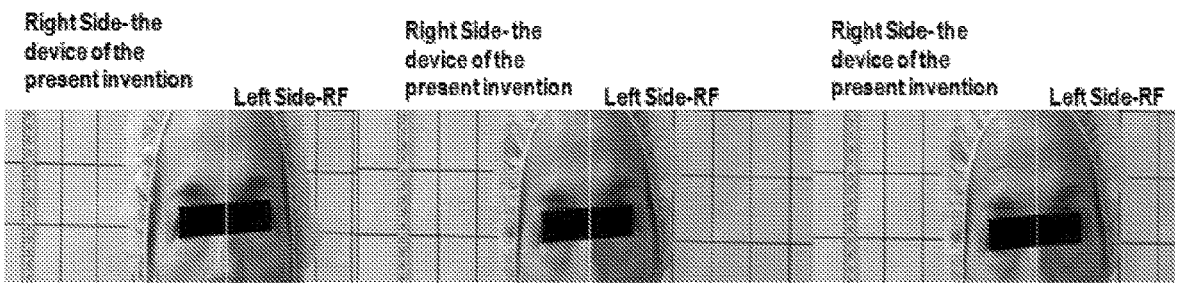
FIGS. 25A-25F illustrate effects of treatment on a patient from the first control group, treated with a device of the present invention on the right side and RF on the left side.
Figures 25B, 25D, 25F:
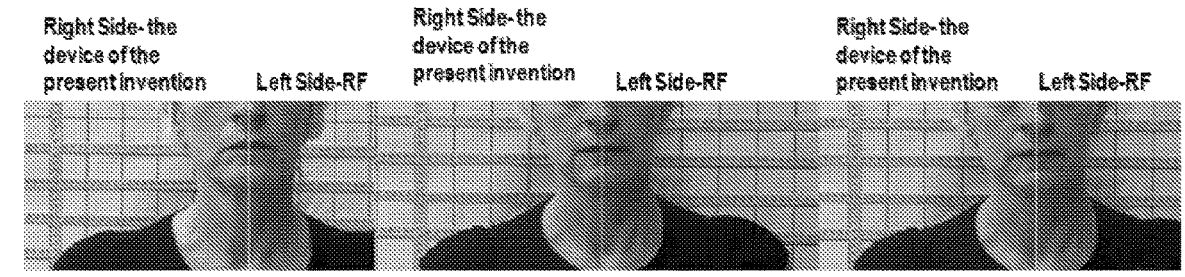
Figure 26A:
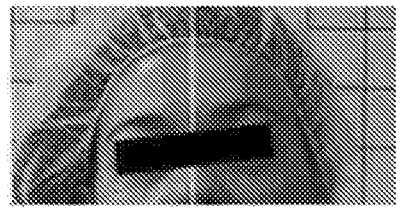
FIGS. 26A-F illustrate effects of treatment on a patient from the second control group, treated with a device of the present invention on the right side and PEMF on the left side.
Figure 26B:
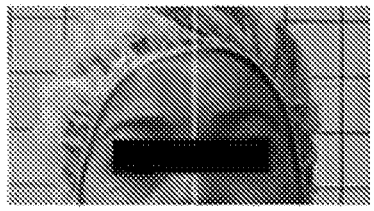
Figure 26C:
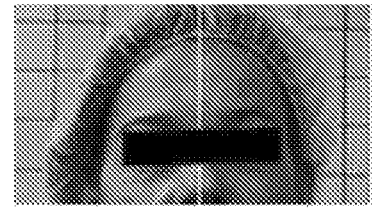
Figure 26D:
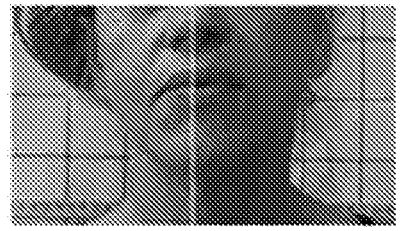
Figure 26E:
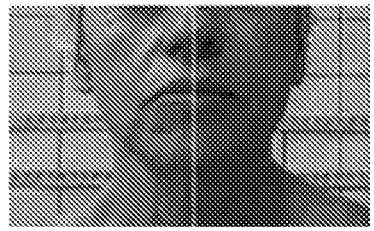
Figure 26F:
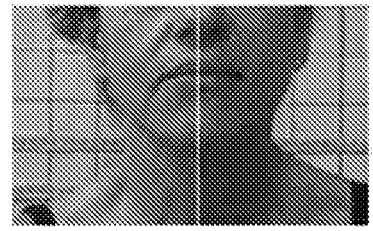
Figure 27A:
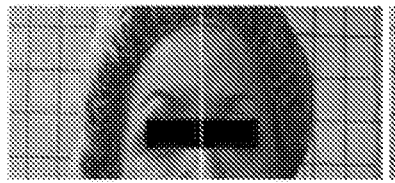
FIGS. 27A-F illustrate effects of treatment on a patient from the third control group, treated with a device of the present invention on the right side and, on the left side, with PEMF followed by RF.
Figure 27B:
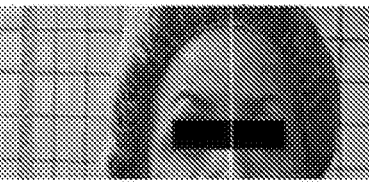
Figure 27C:
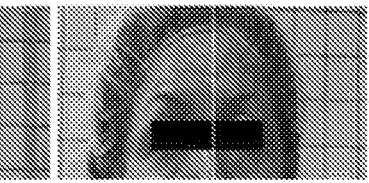
Figure 27D:
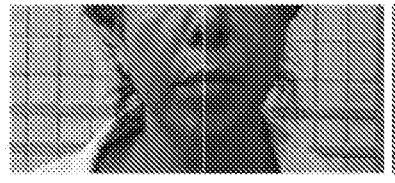
Figure 27E:
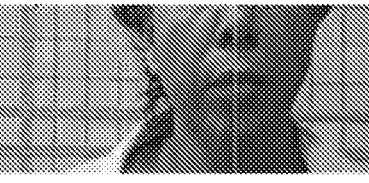
Figure 27F:
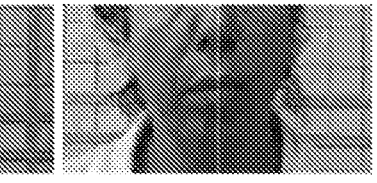

Reference is now made to FIG. 23 which illustrates either a tissue diathermy electrode (200) or a pulsed electromagnetic frequency electrode (300) which is at least partially hollow so that the coil (310) is embedded within the same.

In some embodiments, the coil (310) is coupled to a pulse generator (501).

In some embodiments, the acoustic transducer (300) is made of at least two sections: (i) a piezoelectric material, (502) (to which a pulse generator 503 is coupled); (b) a metallic part (504) which act as an electrode (to which a pulse generator 505 is coupled).

In some embodiments, the device additionally comprises a recess configured to be placed against or in proximity to the skin.

In the some embodiments, the skin is drawn into the recess to a depth sufficient that physical contact is made with any tissue diathermy applicators or pulsed electromagnetic frequency electrodes disposed about the inner surface of the recess, and with the ports themselves.

In the some embodiments, the skin is drawn into the recess without being in physical contact with any tissue diathermy applicators or pulsed electromagnetic frequency electrodes disposed about the inner surface of the housing.

It should also be appreciated that the above described description of methods and apparatus are to be interpreted as including apparatus for carrying out the methods, and methods of using the apparatus of any type as are known to a person or ordinary skill in the art, and which need not be described in detail herein for enabling a person of ordinary skill to practice the invention.

For the main embodiments of the invention, the particular selection of type and model is not critical, although, where specifically identified, this may be relevant. The present invention has been described using detailed descriptions of embodiments thereof that are provided by way of example and are not intended to limit the scope of the invention. No limitation, in general, or by way of words such as "may", "should", "preferably", "must", or other term denoting a degree of importance or motivation, should be considered as a limitation on the scope of the claims or their equivalents unless expressly present in such claim as a literal limitation on its scope. It should be understood that features and steps described with respect to one embodiment can be used with other embodiments and that not all embodiments of the invention have all of the features and/or steps shown in a particular figure or described with respect to one of the embodiments. That is, the disclosure should be considered complete from combinatorial point of view, with each embodiment of each element considered disclosed in conjunction with each other embodiment of each element (and indeed in various combinations of compatible implementations of variations in the same element). Variations of embodiments described will occur to persons of the art. Furthermore, the terms "comprise," "include," "have" and their conjugates, shall mean, when used in the claims, "including but not necessarily limited to." Each element present in the claims in the singular shall mean one or more element as claimed, and when an option is provided for one or more of a group, it shall be interpreted to mean that the claim requires only one member selected from the various options, and shall not require one of each option. The abstract shall not be interpreted as limiting on the scope of the application or claims.

It is noted that some of the above described embodiments describe the best mode contemplated by the inventors and therefore can include structure, acts or details of structures and acts that may not be essential to the invention and which are described as examples. Structure and acts described herein are replaceable by equivalents performing the same function, even if the structure or acts are different, as is known in the art. Therefore, the scope of the invention is limited only by the elements and limitations as used in the claims.

EXAMPLES

An example is given of use of an embodiment of the present invention. The example, which is a clinical test, describes the manner and process of the present invention and sets forth a best mode contemplated by the inventors for carrying out the invention, but is not to be construed as limiting the invention.

Example 1

A clinical test was performed to demonstrate the synergistic effect of the combined PEMF and tissue diathermy device.

The aim of the example is to evaluate the synergistic effect of the combined technology and to compare it to the effects of each technology individually.

A multipolar magnetic pulse generator was used which simultaneously emits RF and magnetic pulses in varying phases that homogeneously cause heating in the treated area that penetrate the dermis and hypodermis.

Method

The test included 40 women of ages ranging from 42-61 years.

They were divided to 4 groups; 1 study group and 3 control groups, with each group including 10 clients. The participants were selected according to predefined criteria which included loose skin in the forehead, eye and neck areas.

All groups were treated for skin tightening of the face (forehead and eyes) and neck. In all groups, the right side of the face and neck was treated only by use of the combined technology of the present invention and the left side of the face and neck was treated according the following:
Study group: the combined technology.
First control group: RF technology.
Second control group: PMF (Pulsed Magnetic Field) technology.
Third control group: PMF technology and, 2 hours later, RF technology.

Sessions were conducted once a week for a period of 8 weeks.

Each session lasted 40 minutes (20 minutes each side), except for the third control group, where each session lasted 60 minutes (right side 20 minutes and left side 40 minutes because 2 different technologies were used).

Clinical results were collected by two methods, one objective and one subjective.

Objective Method

The objective method comprised taking photographs in order to assess the changes in the tightness of the skin induced by the treatments.

The pictures were taken before and after treatment by the same operator under the same conditions. The pictures were taken while the participant sat in front of a chart with vertical and horizontal lines with the camera placed at the same height and the same distance from the subject and with the same lighting conditions.

Subjective Method

Subjective method comprised the clients' self-report.

The subjective method was conducted by questions that each client had to fill after every treatment, referring to the immediate results they had noticed on each treated side, the cumulative effect, the satisfaction of the patient with the results, sensations during the treatments, etc.

The patients received a satisfaction questionnaire which included yes/no questions and questions to be graded on a 1 to 5 satisfaction scale (1—represents "Not At All" and 5 represents "Very Much").

Additionally there were open questions configured to enable the patients to express their feelings following the treatments.

The following questionnaire was handed to the patients after each treatment:

| Question | | Score | Full Answer |
|---|---|---|---|
| | Do you see any visual changes on the right side that was treated? Please describe in the "Full Answer" column. | Not at all  Very much  1 \| 2 \| 3 \| 4 \| 5 | |
| | Are you satisfied from the visual changes on the right side that was treated? | Not at all  Very much  1 \| 2 \| 3 \| 4 \| 5 | |
| | Is there any specific feeling you feel on the right side that was treated (tightness, lifting, stretched, fullness, swelled, loosen, ache, scratching)? Please describe in the "Full Answer" column. | Yes/No | |
| | Are you satisfied from the feeling you feel on the right side that was treated? | Not at all  Very much  1 \| 2 \| 3 \| 4 \| 5 | |
| | Do you see any visual changes on the left side that was treated? Please describe in the "Full Answer" column. | Not at all  Very much  1 \| 2 \| 3 \| 4 \| 5 | |
| | Are you satisfied from the visual changes on the left side that was treated? | Not at all  Very much  1 \| 2 \| 3 \| 4 \| 5 | |
| | Is there any specific feeling you feel on the left side that was treated (tightness, lifting, stretched, fullness, swelled, loosen, ache, scratching)? Please describe in the "Full Answer" column. | Yes/No | |
| | Are you satisfied from the feeling you feel on the left side that was treated? | Not at all  Very much  1 \| 2 \| 3 \| 4 \| 5 | |
| Answer only from the second treatment | How long did the visual results last on the right side that was treated (Please describe in the "Full Answer" column)? | | |
| Answer only from the second treatment | How long did the visual results last on the left side that was treated (Please describe in the "Full Answer" column)? | | |
| Answer only after the 5$^{th}$ treatment | Do you feel that the results on the left side that was treated were cumulative from the first treatment? | Yes/No | |
| Answer only after the 5$^{th}$ treatment | Do you feel that the results on the right side that was treated were cumulative from the first treatment? | Yes/No | |
| Answer after the 8$^{th}$ treatment | Do you feel that the results on the left side that was treated were cumulative from the first treatment? | Yes/No | |
| Answer after the 8$^{th}$ treatment | Do you feel that the results on the right side that was treated were cumulative from the first treatment? | Yes/No | |
| General comments | | | |

Results

Study Group

All patients showed immediate and highly noticeable results on both sides after the first treatment; the skin tightness of the face and neck increased, it was smoother and with fewer wrinkles.

Further, after 5 treatments it was noticeable that the results were cumulative (based on comparison between pictures before the first treatment and pictures before the 5$^{th}$ treatment). After 8 treatments, the skin tightness increased significantly. All clients indicated great satisfaction from the immediate visual results (tightness and stretchiness) as well as the long term results.

The average score of visual results and satisfaction on the right treated side was 4.66 (on a scale of 1 to 5) and on the left treated side the average score was 4.8. 100% of the clients reported that the results on both sides remained all week during the sessions and were cumulative.

They reported a feeling of tightness, firmness and high comfort during the treatment in terms of the sensation ("Feels like hot stones massage") and expressed satisfaction at the short treatment time.

Reference is now made to FIGS. 23A-23F which are pictures of one patient from the study group treated on both sides with the device of the present invention. The pictures were taken before the treatment (see FIG. 23A for the forehead and FIG. 23B for the neck), after the first treatment (see FIG. 23C for the forehead and FIG. 23D for the neck) and after the 8$^{th}$ treatment (see FIG. 23E for the forehead and FIG. 23F for the neck).

First Control Group

All patients showed immediate results on both sides after the first treatment. However, the results were more significant in terms of tightening and wrinkle fading on the right side compared to the left side.

The average score of visual results and satisfaction on the right treated side was 4.93 compared to the left treated side, which was 4.8.

Following 5 treatments, it was noticeable that the results were significantly more cumulative on the right side in comparison to the results on the left side, which lasted only for a few days. 90% of the clients reported that the results on the right side remained all week during the first 5 treatments and were cumulative, compared to 40% of the clients who reported maintenance of the results on the left side.

After 8 treatments, the skin tightness increased even more on the right side and 100% of the clients reported cumulative results compared to the results of the left side, which remained almost the same with only 50% of the clients reporting maintenance of the results.

All clients indicated higher satisfaction with the immediate and long term results on the right side compared to the left side. No difference between both treated sides in terms of comfort was expressed.

Reference is now made to FIGS. 24A-24F which are pictures of one patient from the first control group, which was treated with the device of the present invention on the right side and RF on the left side. The pictures were taken before the treatment (see FIG. 24A for the forehead and FIG. 24B for the neck), after the first treatment (see FIG. 24C for the forehead and FIG. 24D for the neck) and after the 8$^{th}$ treatment (see FIG. 24E for the forehead and FIG. 24F for the neck).

Second Control Group

All patients showed immediate and very noticeable results (skin tightening and wrinkle fading) on the right side after the first treatment and the results improved after the 5$^{th}$ and the 8$^{th}$ treatment.

The average score of visual results and satisfaction on the right treated side was 5.00 compared to the left treated side, which was only 1.9.

It should be pointed out that, on the left side, they didn't show any results in terms of skin tightness during the treatments, although, after the 4$^{th}$ treatment, the skin showed some improvement (it looked more glowing and nourished).

All clients indicated high satisfaction from the immediate and long term results on the right side. 100% of the clients reported that the results on the right side remained all week during the first 5 treatments and were cumulative (and up to the 8$^{th}$ treatment) compared to 10% of the clients who reported maintenance of the results on the left side.

As for the left side, they reported after the 5$^{th}$ treatment satisfaction from the improved condition and look of the skin, although they expressed some disappointment from not having results in terms of skin tightening. They reported high comfort in terms of the treatment sensation during the treatment of both sides.

Reference is now made to FIGS. 25A-25F which are pictures of one patient from the second control group, treated with the device of the present invention on the right side and PEMF on the left side. The pictures were taken before the treatment (see FIG. 25A for the forehead and FIG. 25B for the neck), after the first treatment (see FIG. 25C for the forehead and FIG. 25D for the neck) and after the 8$^{th}$ treatment (see FIG. 25E for the forehead and FIG. 25F for the neck).

Third Control Group

All patients showed on the right side very noticeable immediate and cumulative results (skin tightening and wrinkle fading).

The satisfaction was very high.

On the left side visual results are seen; the immediate results were similar to the right side, however the cumulative results were less significant and less noticeable than those on the right side.

The average score of visual results and satisfaction on the right treated side was 4.83 compared to the left treated side, which was only 2.36. 90% of the clients reported that the results on the right side remained all week during the first 5 treatments (and up to the 8$^{th}$ treatment) and were cumulative.

Only 30% of the clients reported maintenance of the results on the left side. In terms of satisfaction, the clients expressed inconvenience due to the long duration of the treatment.

Reference is now made to FIGS. 26A-26F which are pictures of one patient out of the third control group treated with the device of the present invention on the right side. The left side was treated with PEMF followed by RF. The pictures were taken before the treatment (see FIG. 26A for the forehead and FIG. 26B for the neck), after the first treatment (see FIG. 26C for the forehead and FIG. 26D for the neck) and after the 8$^{th}$ treatment (see FIG. 26E for the forehead and FIG. 26F for the neck).

The following tables (tables 3 and 4) summaries the results:

TABLE 3 average score (1 to 5 scale) of all participant in each group following all the treatments:

| Question | Study group | Control 1 | Control 2 | Control 3 |
|---|---|---|---|---|
| Do you see any visual changes on the right side that was treated? | 4.7 | 4.9 | 5 | 4.9 |
| Are you satisfied with the visual changes on the right side that was treated? | 4.7 | 5 | 5 | 4.8 |
| Are you satisfied with the feeling you feel on the right side that was treated? | 4.6 | 4.9 | 5 | 4.8 |
| Do you see any visual changes on the left side that was treated? | 4.9 | 2.5 | 1.9 | 2.4 |
| Are you satisfied with the visual changes on the left side that was treated? | 4.8 | 2.6 | 2 | 2.3 |
| Are you satisfied with the feeling you feel on the left side that was treated? | 4.7 | 2.4 | 1.8 | 2.4 |

TABLE 4 results of "Yes/No" Questions of all the patients in each group following all the treatments

| Question | Study group | | Control 1 | | Control 2 | | Control 3 | |
|---|---|---|---|---|---|---|---|---|
| | Yes | No | Yes | No | Yes | No | Yes | No |
| Is there any specific feeling you feel on the right side that was treated? (tightness, lifting stretchiness, fullness, swelling, looseness, ache, itchiness)? | 80% | 20% | 90% | 10% | 100% | 0% | 80% | 20% |
| Is there any specific feeling you feel on the left side that was treated? (tightness, lifting stretchiness, fullness, swelling, looseness, ache, itchiness)? | 90% | 10% | 60% | 40% | 40% | 60% | 50% | 50% |
| Answer only after the 5th treatment: Do you feel that the results on the left side that was treated were cumulative from the first treatment? | 100% | 0% | 40% | 60% | 10% | 90% | 30% | 70% |
| Answer only after the 5th treatment: Do you feel that the results on the right side that was treated were cumulative from the first treatment? | 100% | 0% | 90% | 10% | 100% | 0% | 90% | 10% |
| Answer only after the 8th treatment: Do you feel that the results on the left side that was treated were cumulative from the first treatment? | 100% | 0% | 50% | 50% | 20% | 80% | 30% | 70% |
| Answer only after the 8th treatment: Do you feel that the results on the right side that was treated were cumulative from the first treatment? | 100% | 0% | 100% | 0% | 100% | 0% | 100% | 0% |

CONCLUSIONS

The synergistic effect of the device of the present invention clearly shows objectively and subjectively superior results compared to treatments in which only RF, or only PEMF were used.

It has been shown that clients who were treated on the left side with PEMF technology had a much clearer difference between both sides. This is probably since they did not see any tightening effect on the left side.

In addition, it was shown that clients that were treated with the device of the present invention on both sides felt significant changes during the treatment. Yet more, it was harder for them to see a difference between the two sides, since both sides were treated with the device of the present invention and both sides had improved in the same way. 80%-100% of the 40 participants answered "Yes" regarding questions concerning the tightness of the skin and the cumulative results on the right treated area. Of the 30 participants treated on the left side with other technologies, only 10%-50% answered "Yes" regarding questions concerning the tightness of the skin and the cumulative results.

The results with the combined technology (the device of by the present invention) were immediate and they maintained and improved from one treatment to the next. Immediate skin tightening has been seen due to the change of collagen fiber formation induced by thermal technique of the RF (they become shorter and thicker and, as a result, harder).

Long lasting results have been seen due to the increase of new collagen fiber synthesis by the use of both thermal (RF) and non-thermal (PEMF) technologies with the device of the present invention, which enables the formation of a greater number of collagen fibers and, as a result, created a physiological buttress that enables better structural support of the skin.

The assets of the device of the present invention to the medical field are:
Synergistic effect that stimulates dermal fibroblasts which produce new collagen, elastic and reticular fibers by using different mechanisms (heating and non-heating);
Changing the form of a greater number of collagen fiber by making them shorter and thicker; and,
Angiogenesis—increasing the formation of new small blood vessels.

The invention claimed is:
1. An integrated system for increasing rejuvenation of at least one region of mucosal tissue, said system comprising:
   at least two electrodes configured to be placed on said at least one region of mucosal tissue;
   an electromagnetic field generator configured to generate electromagnetic field pulses and to apply said electromagnetic field pulses to said at least one region of mucosal tissue; and,
   a control system;
   wherein:
   none of said electrodes is configured to penetrate said at least one region of mucosal tissue;
   each of said electrodes is configured to conduct radiofrequency (RF) energy pulses to said at least one region of mucosal tissue;

said electrodes are configured to heat said at least one region of mucosal tissue up to a temperature T in a range of 30 degrees Celsius to 80 degrees Celsius; and said control system is configured to control said electromagnetic field generator and application of said heat by said electrodes.

2. The integrated system of claim 1, wherein at least one of the following is held true:
a. at least one portion of said at least one region of mucosal tissue is at least temporarily maintainable at a predetermined temperature range $T_1$ while at least one other portion of said at least one region of mucosal tissue is at least temporarily maintainable at predetermined temperature range $T_2$, where $T_1$ is different from or the same as $T_2$; said predetermined temperature range $T_1$ is selected from a group consisting of: from 30 degrees Celsius to 80 degrees Celsius; and from 40 degrees Celsius to 50 degrees Celsius; and said predetermined temperature range $T_2$ is selected from a group consisting of: from 30 degrees Celsius to 80 degrees Celsius; and from 40 degrees Celsius to 50 degrees Celsius;
b. said at least one region of mucosal tissue is within a vagina; and
c. said system additionally comprises a database configured to store at least one temperature profile, said at least one temperature profile comprising at least one temperature and at least one predetermined portion of said at least one region of mucosal tissue.

3. The integrated system of claim 2, wherein at least one of the following is being held true:
a. said integrated system additionally comprises a processor in communication with said database and with at least one temperature sensor;
b. said control system monitors physical tissue parameters and changes a member of a group consisting of said applied heat, said electromagnetic field pulses and any combination thereof accordingly;
c. a duration of each of said electromagnetic field pulses is in a range between 3 ms and 1000 ms;
d. a frequency F applied by said electromagnetic field pulses ranges between 1 Hz and 50 Hz;
e. a frequency of said RF energy pulses ranges between 200 kHz and 10 MHz; and
f. a power P applied by said RF energy pulses ranges between 1 W and 100 W of RMS average power.

4. The integrated system of claim 3, wherein at least one of the following is being held true:
a. each said at least one temperature sensor is configured to measure at least one temperature in said at least one predetermined portion of said at least one region of mucosal tissue; and
b. said at least one temperature sensor is selected from a group consisting of: a thermistor, a thermocouple and any combination thereof.

5. A method of increasing mucosal tissue rejuvenation of at least one region of mucosal tissue, comprising steps of:
obtaining (i) a pulsed electromagnetic frequency generator; and (ii) a radiofrequency (RF) tissue diathermy device;
applying, either simultaneously or sequentially a member of a group consisting of: (a) heat to at least a portion of mucosal tissue within said at least one region of mucosal tissue up to temperature T, said temperature T in a range of 30 degrees Celsius to 80 degrees Celsius;
(b) pulses of electromagnetic field to at least a portion of said at least one region of mucosal tissue; and any combination thereof;
at least one of the following sets of steps:
a set of steps comprising: (a) providing a database comprising at least one temperature profile, said at least one temperature profile containing at least one temperature and at least one predetermined region of mucosal tissue; (b) measuring said at least one temperature at said at least one predetermined region of mucosal tissue; and (c) feedback controlling RF output to said pulsed electromagnetic frequency generator and said RF tissue diathermy device, thereby maintaining said at least one temperature profile in said at least one predetermined region of mucosal tissue; and,
a set of steps comprising: (a) providing a vaginal treatment device comprising a distal portion and a proximal portion, said distal portion and said proximal portion reversibly connectible; said proximal portion in communication with a member of a group consisting of said pulsed electromagnetic frequency generator, said RF tissue diathermy device and any combination thereof; said distal portion comprising at least two electrodes; (b) placing said distal portion at least partially within a vagina; (c) keeping at least a part of said distal portion substantially stationary within said vagina for a time period in a range between 1 minute and 20 minutes; (d) for at least a portion of said time period, activating a member of a group consisting of said pulsed electromagnetic frequency generator, said RF tissue diathermy device and any combination thereof, said activation applying a member of a group consisting of pulsed electromagnetic field, heat and any combination thereof to said at least a portion of said at least one region of tissue in said vagina; and (e) for at least a portion of said time period, measuring temperature of said at least a portion of said at least one region of tissue in said vagina;
wherein said increase in said rejuvenation of said at least one region of mucosal tissue is greater than a sum of increase in rejuvenation due to said applying heat to said at least a portion of mucosal tissue and increase due to said applying said pulses of electromagnetic field to said at least a portion of said at least one region of mucosal tissue.

6. The method of claim 5, additionally comprising at least one of the following steps:
a. at least temporarily maintaining said at least a portion of said at least one region of mucosal tissue at a predetermined temperature range $T_1$ while at least temporarily maintaining at least one other portion of said at least one region of mucosal tissue at predetermined temperature range $T_2$, where $T_1$ is the same as or different from $T_2$; said predetermined temperature range $T_1$ is selected from a group consisting of: from 30 degrees Celsius to 80 degrees Celsius; and from 40 degrees Celsius to 50 degrees Celsius; and said predetermined temperature range $T_2$ is selected from a group consisting of: from 30 degrees Celsius to 80 degrees Celsius; and from 40 degrees Celsius to 50 degrees Celsius;
b. selecting said at least one region of mucosal tissue to be within a vagina;
c. a step selected from a group consisting of: simultaneously applying said pulses of electromagnetic field and said heat, sequentially applying said pulses of electromagnetic field and said heat and any combination thereof;
d. selecting at least one parameter from a group consisting of (a) a duration of each pulse applied by said pulsed electromagnetic frequency generator is in a range between 3 ms and 1000 ms; (b) a magnetic field intensity B of each of said pulses of electromagnetic field is in a range from 0 to 15 Gauss; (c) a frequency F of each of said pulses of electromagnetic field is in a range between 1 Hz to 50 Hz; (d) a power P applied by said step of applying said pulses of electromagnetic field to said at least a portion of said at least one region of mucosal tissue is in a range between 1 W and 100 W of RMS average power and any combination thereof;
e. selecting a duration for application of said heat to be in a range from 0.01 minutes to 60 minutes;
f. selecting a manner of applying said heat and said pulses of electromagnetic field from a group consisting of: simultaneously, sequentially, separately and any combination thereof; and
g. said step of applying heat to a tissue comprises steps of:
  i. electrically coupling at least two electrodes to said RF tissue diathermy device;
  ii. placing said at least two electrodes on said at least one region of mucosal tissue; and,
  iii. applying a member of a group consisting of said pulses of electromagnetic field, power from said RF tissue diathermy device applied via at least one of said electrodes, and any combination thereof to said at least one region of mucosal tissue.

7. The method of claim 5, additionally comprising steps of (a) providing said distal portion with at least two pairs of electrodes; and (b) controlling each pair separately, thereby maintaining said at least one temperature profile within at least a portion of said at least one region of mucosal tissue.

8. An integrated system for increasing rejuvenation of at least one region of a patient, said at least one region selected from a group consisting of skin of said patient, mucosal tissue of said patient and any combination thereof, said integrated system comprising:
at least two electrodes configured to be placed on said at least one region;
an electromagnetic field generator configured to generate electromagnetic field pulses;
a generator configured to generate radiofrequency (RF) energy pulses; and
a control system;
wherein:
  none of said at least two electrodes is configured to penetrate said at least one region;
  each of said at least two electrodes is configured to provide said RF energy pulses to said at least one region, said RF energy pulses configured to apply heat up to a temperature T in a range from 30 degrees Celsius to 80 degrees Celsius;
  said control system is configured to control a member of a group consisting of: said electromagnetic field generator, application of said heat by said electrodes and any combination thereof; and,
  said electromagnetic field pulses are applyable to said at least one region and said heat is applyable to said at least one region in a manner selected from a group consisting of: simultaneously, sequentially, separately and any combination thereof.

9. The integrated system of claim 8, wherein at least one of the following is held true:
a. at least one portion of said at least one region is at least temporarily maintainable at a predetermined temperature range $T_1$ while at least one other portion of said at least one region is at least temporarily maintainable at predetermined temperature range $T_2$, where $T_1$ is different from or the same as $T_2$; said predetermined temperature range $T_1$ is selected from a group consisting of: from 30 degrees Celsius to 80 degrees Celsius and from 40 degrees Celsius to 50 degrees Celsius; and said predetermined temperature range $T_2$ is selected from a group consisting of: from 30 degrees Celsius to 80 degrees Celsius and from 40 degrees Celsius to 50 degrees Celsius;
b. said at least one region of said patient is within a vagina;
c. said integrated system additionally comprises a database configured to store at least one temperature profile, said at least one temperature profile comprising at least one temperature and at least one predetermined region of said patient;
d. said heat applied to said at least one region of said patient is obtainable by emitting RF radiation or via producing electrical current absorbed by tissue;
e. said integrated system is configured to provide a dynamic magnetic field such that a magnitude of said electromagnetic pulses is variable with time;
f. physical tissue parameters are monitorable by said control system and a member of a group consisting of: said applied heat, said electromagnetic field pulses and any combination thereof is changeable accordingly;
g. a duration of each electromagnetic field pulse is in a range between 3 ms and 1000 ms;
h. a frequency F applied by said RF energy pulses is in a range between 200 kHz and 10 MHz; and
i. a power P applied by said RF energy pulses is in a range between 1 W and 100 W of RMS average power.

10. The integrated system of claim 9, additionally comprising a processor in communication with said database and with at least one temperature sensor, said at least one temperature sensor configured to measure at least one temperature in at least one portion of said at least one region; said at least one temperature sensor is selected from a group consisting of: a thermistor, a thermocouple and any combination thereof.

11. An integrated system for increasing rejuvenation of at least one region of mucosal tissue, said system comprising:
at least two electrodes configured to be placed on said at least one region of mucosal tissue;
a control system;
wherein:
  none of said electrodes is configured to penetrate said at least one region of mucosal tissue;
  each of said electrodes is configured to conduct radiofrequency (RF) energy to said at least one region of mucosal tissue;
  said electrodes are configured to heat said at least one region of mucosal tissue up to a temperature T in a range of 30 degrees Celsius to 80 degrees Celsius; and
  said control system is configured to control an electromagnetic field generator and application of said heat by said electrodes.

12. The integrated system of claim 11, wherein at least one of the following is held true:
a. at least one portion of said at least one region of mucosal tissue is at least temporarily maintainable at a predetermined temperature range $T_1$ while at least one other portion of said at least one region of mucosal tissue is at least temporarily maintainable at predetermined temperature range $T_2$, where $T_1$ is different from or the same as $T_2$; said predetermined temperature range $T_1$ is selected from a group consisting of: from 30 degrees Celsius to 80 degrees Celsius; and from 40 degrees Celsius to 50 degrees Celsius; and said predetermined temperature range $T_2$ is selected from a group consisting of: from 30 degrees Celsius to 80 degrees Celsius; and from 40 degrees Celsius to 50 degrees Celsius;

b. said at least one region of mucosal tissue is within a vagina; and c. said system additionally comprises a database configured to store at least one temperature profile, said at least one temperature profile comprising at least one temperature and at least one predetermined portion of said at least one region of mucosal tissue.

13. The integrated system of claim 12, wherein at least one of the following is being held true:

a. said integrated system additionally comprises a processor in communication with a database configured to store at least one temperature profile and with at least one temperature sensor;

b. said control system monitors physical tissue parameters and changes a member of a group consisting of said applied heat, electromagnetic field pulses and any combination thereof accordingly;

c. a duration of each electromagnetic field pulse is in a range between 3 ms and 1000 ms;

d. a frequency F applied by an electromagnetic field pulse ranges between 1 Hz and 50 Hz;

e. a frequency of pulses of said RF energy ranges between 200 kHz and 10 MHz; and f. a power P applied by pulses of said RF energy ranges between 1 W and 100 W of RMS average power.

14. The integrated system of claim 13, wherein at least one of the following is being held true:

a. each said at least one temperature sensor is configured to measure at least one temperature in said at least one predetermined portion of said at least one region of mucosal tissue; and b. said at least one temperature sensor is selected from a group consisting of: a thermistor, a thermocouple and any combination thereof.

15. A method of increasing mucosal tissue rejuvenation of at least one region of mucosal tissue, comprising steps of:

obtaining a radiofrequency (RF) tissue diathermy device;

applying, either simultaneously or sequentially a member of a group consisting of: (a) heat to at least a portion of mucosal tissue within said at least one region of mucosal tissue up to temperature T, said temperature T in a range of 30 degrees Celsius to 80 degrees Celsius; (b) radiofrequency (RF) energy to at least a portion of said at least one region of mucosal tissue; and any combination thereof;

at least one of the following sets of steps:

a set of steps comprising: (a) providing a database comprising at least one temperature profile, said at least one temperature profile containing at least one temperature and at least one predetermined region of mucosal tissue; (b) measuring said at least one temperature at said at least one predetermined region of mucosal tissue; and (c) feedback controlling RF output to said RF tissue diathermy device, thereby maintaining said at least one temperature profile in said at least one predetermined region of mucosal tissue; and, a set of steps comprising: (a) providing a vaginal treatment device comprising a distal portion and a proximal portion, said distal portion and said proximal portion reversibly connectible; said proximal portion in communication with a member of a group consisting of said RF tissue diathermy device and any combination thereof; said distal portion comprising at least two electrodes; (b) placing said distal portion at least partially within a vagina; (c) keeping at least a part of said distal portion substantially stationary within said vagina for a time period in a range between 1 minute and 20 minutes; (d) for at least a portion of said time period, activating a member of a group consisting of said RF tissue diathermy device and any combination thereof, said activation applying a member of a group consisting of pulsed electromagnetic field, heat and any combination thereof to said at least a portion of said at least one region of tissue in said vagina; and (e) for at least a portion of said time period, measuring temperature of said at least a portion of said at least one region of tissue in said vagina.

16. The method of claim 15, additionally comprising at least one of the following steps:

a. at least temporarily maintaining said at least a portion of said at least one region of mucosal tissue at a predetermined temperature range $T_1$ while at least temporarily maintaining at least one other portion of said at least one region of mucosal tissue at predetermined temperature range $T_2$, where $T_1$ is the same as or different from $T_2$; said predetermined temperature range $T_1$ is selected from a group consisting of: from 30 degrees Celsius to 80 degrees Celsius; and from 40 degrees Celsius to 50 degrees Celsius; and said predetermined temperature range $T_2$ is selected from a group consisting of: from 30 degrees Celsius to 80 degrees Celsius; and from 40 degrees Celsius to 50 degrees Celsius;

b. selecting said at least one region of mucosal tissue to be within a vagina;

c. a step selected from a group consisting of: simultaneously applying pulses of electromagnetic field and said heat, sequentially applying pulses of electromagnetic field and said heat, and any combination thereof;

d. selecting at least one parameter from a group consisting of (a) a duration of each pulse applied by a pulsed electromagnetic field generator is in a range between 3 ms and 1000 ms; (b) a magnetic field intensity B of each of said pulses of electromagnetic field is in a range from 0 to 15 Gauss; (c) a frequency F of each of said pulses of electromagnetic field is in a range between 1 Hz to 50 Hz; (d) a power P applied by said step of applying said pulses of electromagnetic field to said at least a portion of said at least one region of mucosal tissue is in a range between 1 W and 100 W of RMS average power and any combination thereof;

e. selecting a duration for application of said heat to be in a range from 0.01 minutes to 60 minutes;

f. selecting a manner of applying said heat and said pulses of electromagnetic field from a group consisting of: simultaneously, sequentially, separately and any combination thereof; and g. said step of applying heat to a tissue comprises steps of:
   i. electrically coupling at least two electrodes to said RF tissue diathermy device;
   ii. placing said at least two electrodes on said at least one region of mucosal tissue; and,
   iii. applying a member of a group consisting of said pulses of electromagnetic field, power from said RF tissue diathermy device applied via at least one of said electrodes, and any combination thereof to said at least one region of mucosal tissue.

17. The method of claim 15, additionally comprising steps of (a) providing said distal portion with at least two pairs of electrodes; and (b) controlling each pair separately, thereby maintaining said at least one temperature profile within at least a portion of said at least one region of mucosal tissue.

18. An integrated system for increasing rejuvenation of at least one region of a patient, said at least one region selected from a group consisting of skin of said patient, mucosal tissue of said patient and any combination thereof, said integrated system comprising:
   at least two electrodes configured to be placed on said at least one region;
   a generator configured to generate radiofrequency (RF) energy; and
   a control system;
   wherein:
      none of said at least two electrodes is configured to penetrate said at least one region;
      each of said at least two electrodes is configured to provide said RF energy to said at least one region, said RF energy configured to apply heat up to a temperature T in a range from 30 degrees Celsius to 80 degrees Celsius;
      said control system is configured to control a member of a group consisting of: an electromagnetic field generator, application of said heat by said electrodes and any combination thereof; and,
      an electromagnetic field is applyable to said at least one region and said heat is applyable to said at least one region in a manner selected from a group consisting of: simultaneously, sequentially, separately and any combination thereof.

19. The integrated system of claim 18, wherein at least one of the following is held true:

a. at least one portion of said at least one region is at least temporarily maintainable at a predetermined temperature range $T_1$ while at least one other portion of said at least one region is at least temporarily maintainable at predetermined temperature range $T_2$, where $T_1$ is different from or the same as $T_2$; said predetermined temperature range $T_1$ is selected from a group consisting of: from 30 degrees Celsius to 80 degrees Celsius and from 40 degrees Celsius to 50 degrees Celsius; and said predetermined temperature range $T_2$ is selected from a group consisting of: from 30 degrees Celsius to 80 degrees Celsius and from 40 degrees Celsius to 50 degrees Celsius;
b. said at least one region of said patient is within a vagina;
c. said integrated system additionally comprises a database configured to store at least one temperature profile, said at least one temperature profile comprising at least one temperature and at least one predetermined region of said patient;
d. said heat applied to said at least one region of said patient is obtainable by emitting RF radiation or via producing electrical current absorbed by tissue;
e. said integrated system is configured to provide a dynamic magnetic field such that a magnitude of said magnetic field is variable with time;
f. physical tissue parameters are monitorable by said control system and a member of a group consisting of: said applied heat, electromagnetic field pulses and any combination thereof is changeable accordingly;
g. a duration of each electromagnetic field pulse is in a range between 3 ms and 1000 ms;
h. a frequency F applied by said RF energy is in a range between 200 kHz and 10 MHz; and
i. a power P applied by said RF energy is in a range between 1 W and 100 W of RMS average power.

20. The integrated system of claim 19, additionally comprising a processor in communication with said database and with at least one temperature sensor, said at least one temperature sensor configured to measure at least one temperature in at least one portion of said at least one region; said at least one temperature sensor is selected from a group consisting of: a thermistor, a thermocouple and any combination thereof.

* * * * *